US007438919B2

(12) United States Patent
Dowling et al.

(10) Patent No.: US 7,438,919 B2
(45) Date of Patent: Oct. 21, 2008

(54) COLD-ADAPTED EQUINE INFLUENZA VIRUSES

(75) Inventors: Patricia W. Dowling, Pittsburgh, PA (US); Julius S. Youngner, Pittsburgh, PA (US)

(73) Assignee: The University of Pittsburgh -- of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 11/682,443

(22) Filed: Mar. 6, 2007

(65) Prior Publication Data

US 2007/0196388 A1  Aug. 23, 2007

Related U.S. Application Data

(60) Division of application No. 10/872,014, filed on Jun. 18, 2004, now Pat. No. 7,201,909, which is a division of application No. 10/434,811, filed on May 8, 2003, now Pat. No. 6,824,784, which is a division of application No. 09/762,861, filed as application No. PCT/US99/18583 on Aug. 12, 1999, now Pat. No. 6,579,528, which is a continuation-in-part of application No. 09/133,921, filed on Aug. 13, 1998, now Pat. No. 6,177,082.

(51) Int. Cl.
  *A61K 39/145* (2006.01)
(52) U.S. Cl. ............... 424/209.1; 435/91.1; 536/23.72
(58) Field of Classification Search .............. 424/209.1; 435/91.1; 536/23.72
  See application file for complete search history.

(56) References Cited

U.S. PATENT DOCUMENTS

| 3,518,347 | A | 6/1970 | Pavilanis et al. ............... 424/89 |
| 4,631,191 | A | 12/1986 | Dale et al. ..................... 424/88 |
| 4,683,137 | A | 7/1987 | Coggins et al. ............... 424/89 |
| 4,693,893 | A | 9/1987 | Campbell et al. ............. 424/89 |
| 4,920,213 | A | 4/1990 | Dale et al. ..................... 536/27 |
| 5,149,531 | A | 9/1992 | Youngner et al. ............. 424/89 |
| 5,690,937 | A | 11/1997 | Parkin et al. ............. 424/199.1 |

FOREIGN PATENT DOCUMENTS

| WO | WO83/03546 | 10/1983 |
| WO | WO 93/21310 | 10/1993 |

OTHER PUBLICATIONS

Livesay et al, The Veterinary Record, Nov. 20, 1993, vol. 133, No. 21, pp. 515-519.*
Brundage-Anguish, et al., 1982, *Am J Vet Res*, 43(5), pp. 869-874.
Enami, et al., 1990, *PNAS*, vol. 87, pp. 3802-3805.
Estola, et al., 1976, *Nord Vet med* vol. 28(7-8), pp. 353-356.
Hannant, et al., Feb. 6, 1988, *Vet Rec*, pp. 125-128.
Holmes, et al., 1992, *Equine Infectious Diseases VI: Proceedings of the Sixth International Conference*, Jul. 7-11, 1991, pp. 253-258.
Ilobi, et al., 1998, *Arch Virol*, vol. 143, pp. 891-901.
Kucera, et al., 1977, *Can J Comp Med*, 41(3), pp. 326-331.
Mumford, et al., 1983, *J Hyg (Lond)*, vol. 90(3), pp. 385-395.
Noble, et al., 1994, *J Gen Virol* vol. 75, pp. 3485-3491.
Reed, et al., 1938, *The American Journal of Hygiene*, vol. 27, pp. 493-497.
Timoney, P.J., 1996, *Comp Immunol Microbiol Infect Dis*, vol. 19(3), pp. 205-211.
USDA, 9 CFR 113.2XX, Oct. 28, 1994, Supplemental Assay Method for Conducting the Hemagglutination Inhibition Assay for Equine Influenza Antibody.
Van Maanen, et al., 1992, *Vet Q*, vol. 14(1), pp. 13-17.
Van Oirschot, et al., 1991, *Zentralbl Veterinarmed [B]*, vol. 38(5), pp. 391-396.
Wood, et al., 1983, *J Hyg (Lond)* vol. 90(3), pp. 371-384.
Wilson, et al., 1993, *Vet Clin North Am Equine Practi*, vol. 9(2), pp. 257-282.
Youngner, et al., 1994, *J. of Clinical of Microbiology*, vol. 32(3), pp. 750-754.
Lunn et al., 1999, *Vaccine*, vol. 17, pp. 2245-2258.
Romanova et al., 1997, *Vaccine*, vol. 15, No. 6/7, pp. 653-658.
Adeyefa et al., *Epidemiol. Infect.*, Oct. 1996, vol. 117, No. 2, pp. 367-374.

* cited by examiner

*Primary Examiner*—Ali R. Salimi
(74) *Attorney, Agent, or Firm*—Heska Corporation

(57) ABSTRACT

The present invention provides experimentally-generated cold-adapted equine influenza viruses, and reassortant influenza A viruses comprising at least one genome segment of such an equine influenza virus, wherein the equine influenza virus genome segment confers at least one identifying phenotype of the cold-adapted equine influenza virus, such as cold-adaptation, temperature sensitivity, dominant interference, or attenuation. Such viruses are formulated into therapeutic compositions to protect animals from diseases caused by influenza A viruses, and in particular, to protect horses from disease caused by equine influenza virus. The present invention also includes methods to protect animals from diseases caused by influenza A virus utilizing the claimed therapeutic compositions. Such methods include using a therapeutic composition as a vaccine to generate a protective immune response in an animal prior to exposure to a virulent virus, and using a therapeutic composition as a treatment for an animal that has been recently infected with a virulent virus, or is likely to be subsequently exposed to virulent virus in a few days whereby the therapeutic composition interferes with the growth of the virulent virus, even in the absence of immunity. The present invention also provides methods to produce cold-adapted equine influenza viruses, and reassortant influenza A viruses having at least one genome segment of an equine influenza virus generated by cold-adaption.

8 Claims, No Drawings

COLD-ADAPTED EQUINE INFLUENZA VIRUSES

This application is a divisional of U.S. Ser. No. 10/872,014, filed Jun. 18, 2004 now U.S. Pat. No. 7,201,909; which is a divisional of U.S. Ser. No. 10/434,811, filed May 8, 2003, now U.S. Patent No. 6,824,784; which is a divisional of U.S. Ser. No. 09/762,861, filed Aug. 24, 2001, now U.S. Pat. No. 6,579,528; which is a U.S. national phase filing under 35 U.S.C. 371 of international application PCT/US99/18583, filed Aug. 12, 1999; which is a continuation-in-part of U.S. Ser. No. 09/133,921, filed Aug. 13, 1998, now U.S. Pat. No. 6,177,082 on Jan. 23, 2001; all of foregoing entitled "COLD-ADAPTED EQUINE INFLUENZA VIRUSES" and incorporated by reference herein.

FIELD OF THE INVENTION

The present invention relates to experimentally-generated cold-adapted equine influenza viruses, and particularly to cold-adapted equine influenza viruses having additional phenotypes, such as attenuation, dominant interference, or temperature sensitivity. The invention also includes reassortant influenza A viruses which contain at least one genome segment from such an equine influenza virus, such that the reassortant virus includes certain phenotypes of the donor equine influenza virus. The invention further includes genetically-engineered equine influenza viruses, produced through reverse genetics, which comprise certain identifying phenotypes of a cold-adapted equine influenza virus of the present invention. The present invention also relates to the use of these viruses in therapeutic compositions to protect animals from diseases caused by influenza viruses.

BACKGROUND OF THE INVENTION

Equine influenza virus has been recognized as a major respiratory pathogen in horses since about 1956. Disease symptoms caused by equine influenza virus can be severe, and are often followed by secondary bacterial infections. Two subtypes of equine influenza virus are recognized, namely subtype-1, the prototype being A/Equine/Prague/1/56 (H7N7), and subtype-2, the prototype being A/Equine/Miami/1/63 (H3N8). Presently, the predominant virus subtype is subtype-2, which has further diverged among Eurasian and North American isolates in recent years.

The currently licensed vaccine for equine influenza is an inactivated (killed) virus vaccine. This vaccine provides minimal, if any, protection for horses, and can produce undesirable side effects, for example, inflammatory reactions at the site of injection. See, e.g., Mumford, 1987, *Equine Infectious Disease IV*, 207-217, and Mumford, et al., 1993, *Vaccine* 11, 1172-1174. Furthermore, current modalities cannot be used in young foals, because they cannot overcome maternal immunity, and can induce tolerance in a younger animal. Based on the severity of disease, there remains a need for safe, effective therapeutic compositions to protect horses against equine influenza disease.

Production of therapeutic compositions comprising cold-adapted human influenza viruses is described, for example, in Maassab, et al., 1960, *Nature* 7, 612-614, and Maassab, et al., 1969, *J. Immunol.* 102, 728-732. Furthermore, these researchers noted that cold-adapted human influenza viruses, i.e., viruses that have been adapted to grow at lower than normal temperatures, tend to have a phenotype wherein the virus is temperature sensitive; that is, the virus does not grow well at certain higher, non-permissive temperatures at which the wild-type virus will grow and replicate. Various cold-adapted human influenza A viruses, produced by reassortment with existing cold-adapted human influenza A viruses, have been shown to elicit good immune responses in vaccinated individuals, and certain live attenuated cold-adapted reassortant human influenza A viruses have proven to protect humans against challenge with wild-type virus. See, e.g., Clements, et al., 1986, *J. Clin. Microbiol.* 23, 73-76. In U.S. Pat. No. 5,149,531, by Youngner, et al., issued Sep. 22, 1992, the inventors of the present invention further demonstrated that certain reassortant cold-adapted human influenza A viruses also possess a dominant interference phenotype, i.e., they inhibit the growth of their corresponding parental wild-type strain, as well as heterologous influenza A viruses. U.S. Pat. No. 4,683,137, by Coggins et al., issued Jul. 28, 1987, and U.S. Pat. No. 4,693,893, by Campbell, issued Sep. 15, 1987, disclose attenuated therapeutic compositions produced by reassortment of wild-type equine influenza viruses with attenuated, cold-adapted human influenza A viruses. Although these therapeutic compositions appear to be generally safe and effective in horses, they pose a significant danger of introducing into the environment a virus containing both human and equine influenza genes.

SUMMARY OF THE INVENTION

The present invention provides experimentally-generated cold-adapted equine influenza viruses, reassortant influenza A viruses that comprise at least one genome segment of an equine influenza virus generated by cold-adaptation such that the equine influenza virus genome segment confers at least one identifying phenotype of a cold-adapted equine influenza virus on the reassortant virus, and genetically-engineered equine influenza viruses, produced through reverse genetics, which comprise at least one identifying phenotype of a cold-adapted equine influenza virus. Identifying phenotypes include cold-adaptation, temperature sensitivity, dominant interference, and attenuation. The invention further provides a therapeutic composition to protect an animal against disease caused by an influenza A virus, where the therapeutic composition includes a cold-adapted equine influenza virus a reassortant influenza A virus, or a genetically-engineered equine influenza virus of the present invention. Also provided is a method to protect an animal from diseases caused by an influenza A virus which includes the administration of such a therapeutic composition. Also provided are methods to produce a cold-adapted equine influenza virus, and methods to produce a reassortant influenza A virus which comprises at least one genome segment of a cold-adapted equine influenza virus, where the equine influenza genome segment confers on the reassortant virus at least one identifying phenotype of the cold-adapted equine influenza virus.

A cold-adapted equine influenza virus is one that replicates in embryonated chicken eggs at a temperature ranging from about 26° C. to about 30° C. Preferably, a cold-adapted equine influenza virus, reassortant influenza A virus, or genetically-engineered equine influenza virus of the present invention is attenuated, such that it will not cause disease in a healthy animal.

In one embodiment, a cold-adapted equine influenza virus, reassortant influenza A virus, or genetically-engineered equine influenza virus of the present invention is also temperature sensitive, such that the virus replicates in embryonated chicken eggs at a temperature ranging from about 26° C. to about 30° C., forms plaques in tissue culture cells at a permissive temperature of about 34° C., but does not form plaques in tissue culture cells at a non-permissive temperature of about 39° C.

In one embodiment, such a temperature sensitive virus comprises two mutations: a first mutation that inhibits plaque formation at a temperature of about 39° C., that mutation co-segregating with the genome segment that encodes the viral nucleoprotein gene; and a second mutation that inhibits all viral protein synthesis at a temperature of about 39° C.

In another embodiment, a cold-adapted, temperature sensitive equine influenza virus of the present invention replicates in embryonated chicken eggs at a temperature ranging from about 26° C. to about 30° C., forms plaques in tissue culture cells at a permissive temperature of about 34° C., but does not form plaques in tissue culture cells or express late viral proteins at a non-permissive temperature of about 37° C.

Typically, a cold-adapted equine influenza virus of the present invention is produced by passaging a wild-type equine influenza virus one or more times, and then selecting viruses that stably grow and replicate at a reduced temperature. A cold-adapted equine influenza virus produced thereby includes, in certain embodiments, a dominant interference phenotype, that is, the virus, when co-infected with a parental equine influenza virus or heterologous wild-type influenza A virus, will inhibit the growth of that virus.

Examples of cold-adapted equine influenza viruses of the present invention include EIV-P821, identified by accession No. ATCC VR 2625; EIV-P824, identified by accession No. ATCC VR 2624; EIV-MSV+5, identified by accession No. ATCC VR 2627; and progeny of such viruses.

Therapeutic compositions of the present invention include from about $10^5$ TCID$_{50}$ units to about $10^8$ TCID$_{50}$ units, and preferably about $2 \times 10^6$ TCID$_{50}$ units, of a cold-adapted equine influenza virus, reassortant influenza A virus, or genetically-engineered equine influenza virus of the present invention.

The present invention also includes a method to protect an animal from disease caused by an influenza A virus, which includes the step of administering to the animal a therapeutic composition including a cold-adapted equine influenza virus, a reassortant influenza A virus, or a genetically-engineered equine influenza virus of the present invention. Preferred animals to protect include equids, with horses and ponies being particularly preferred.

Yet another embodiment of the present invention is a method to generate a cold-adapted equine influenza virus. The method includes the steps of passaging a wild-type equine influenza virus; and selecting viruses that grow at a reduced temperature. In one embodiment, the method includes repeating the passaging and selection steps one or more times, while progressively reducing the temperature. Passaging of equine influenza virus preferably takes place in embryonated chicken eggs.

Another embodiment is an method to produce a reassortant influenza A virus through genetic reassortment of the genome segments of a donor cold-adapted equine influenza virus of the present invention with the genome segments of a recipient influenza A virus. Reassortant influenza A viruses of the present invention are produced by a method that includes the steps of: (a) mixing the genome segments of a donor cold-adapted equine influenza virus with the genome segments of a recipient influenza A virus, and (b) selecting viruses which include at least one identifying phenotype of the donor equine influenza virus. Identifying phenotypes include cold-adaptation, temperature sensitivity, dominant interference, and attenuation. Preferably, such reassortant viruses at least include the attenuation phenotype of the donor virus. A typical reassortant virus will have the antigenicity of the recipient virus, that is, it will retain the hemagglutinin (HA) and neuraminidase (NA) phenotypes of the recipient virus.

The present invention further provides methods to propagate cold-adapted equine influenza viruses or reassortant influenza A viruses of the present invention. These methods include propagation in embryonated chicken eggs or in tissue culture cells.

DETAILED DESCRIPTION OF THE INVENTION

The present invention provides experimentally-generated cold-adapted equine influenza viruses comprising certain defined phenotypes, which are disclosed herein. It is to be noted that the term "a" or "an" entity, refers to one or more of that entity; for example, "a cold-adapted equine influenza virus" can include one or more cold-adapted equine influenza viruses. As such, the terms "a" (or "an"), "one or more," and "at least one" can be used interchangeably herein. It is also to be noted that the terms "comprising," "including," and "having" can be used interchangeably. Furthermore, an item "selected from the group consisting of" refers to one or more of the items in that group, including combinations thereof.

A cold-adapted equine influenza virus of the present invention is a virus that has been generated in the laboratory, and as such, is not a virus as occurs in nature. Since the present invention also includes those viruses having the identifying phenotypes of such a cold-adapted equine influenza virus, an equine influenza virus isolated from a mixture of naturally-occurring viruses, i.e., removed from its natural milieu, but having the claimed phenotypes, is included in the present invention. A cold-adapted equine influenza virus of the present invention does not require any specific level of purity. For example, a cold-adapted equine influenza virus grown in embryonated chicken eggs may be in a mixture with the allantoic fluid (AF), and a cold-adapted equine influenza virus grown in tissue culture cells may be in a mixture with disrupted cells and tissue culture medium.

As used herein, an "equine influenza virus" is an influenza virus that infects and grows in equids, e.g., horses or ponies. As used herein, "growth" of a virus denotes the ability of the virus to reproduce or "replicate" itself in a permissive host cell. As such, the terms, "growth of a virus" and "replication of a virus" are used interchangeably herein. Growth or replication of a virus in a particular host cell can be demonstrated and measured by standard methods well-known to those skilled in the art of virology. For example, samples containing infectious virus, e.g., as contained in nasopharyngeal secretions from an infected horse, are tested for their ability to cause cytopathic effect (CPE), e.g., virus plaques, in tissue culture cells. Infectious virus may also be detected by inoculation of a sample into the allantoic cavity of embryonated chicken eggs, and then testing the AF of eggs thus inoculated for its ability to agglutinate red blood cells, i.e., cause hemagglutination, due to the presence of the influenza virus hemagglutinin (HA) protein in the AF.

Naturally-occurring, i.e., wild-type, equine influenza viruses replicate well at a temperature from about 34° C. to about 39° C. For example, wild-type equine influenza virus replicates in embryonated chicken eggs at a temperature of about 34° C., and replicates in tissue culture cells at a temperature from about 34° C. to about 39° C. As used herein, a "cold-adapted" equine influenza virus is an equine influenza virus that has been adapted to grow at a temperature lower than the optimal growth temperature for equine influenza virus. One example of a cold-adapted equine influenza virus of the present invention is a virus that replicates in embryonated chicken eggs at a temperature of about 30° C. A preferred cold-adapted equine influenza virus of the present invention replicates in embryonated chicken eggs at a temperature of about 28° C. Another preferred cold-adapted equine influenza virus of the present invention replicates in embryonated chicken eggs at a temperature of about 26° C. In general, preferred cold-adapted equine influenza viruses of the present invention replicate in embryonated chicken eggs at a temperature ranging from about 26° C. to about 30° C., i.e., at a range of temperatures at which a wild-type virus will grow poorly or not at all. It should be noted that the ability of such viruses to replicate within that temperature range does not preclude their ability to also replicate at higher or lower temperatures. For example, one embodiment is a cold-adapted equine influenza virus that replicates in embryonated chicken eggs at a temperature of about 26° C., but also replicates in tissue culture cells at a temperature of about 34° C. As with wild-type equine influenza viruses, cold-adapted equine influenza viruses of the present invention generally form plaques in tissue culture cells, for example Madin Darby Canine Kidney Cells (MDCK) at a temperature of about 34° C. Examples of suitable and preferred cold-adapted equine influenza viruses of the present invention are disclosed herein.

One embodiment of the present invention is a cold-adapted equine influenza virus that is produced by a method which includes passaging a wild-type equine influenza virus, and then selecting viruses that grow at a reduced temperature. Cold-adapted equine influenza viruses of the present invention can be produced, for example, by sequentially passaging a wild-type equine influenza virus in embryonated chicken eggs at progressively lower temperatures, thereby selecting for certain members of the virus mixture which stably replicate at the reduced temperature. An example of a passaging procedure is disclosed in detail in the Examples section. During the passaging procedure, one or more mutations appear in certain of the single-stranded RNA segments comprising the influenza virus genome, which alter the genotype, i.e., the primary nucleotide sequence of those RNA segments. As used herein, a "mutation" is an alteration of the primary nucleotide sequence of any given RNA segment making up an influenza virus genome. Examples of mutations include substitution of one or more nucleotides, deletion of one or more nucleotides, insertion of one or more nucleotides, or inversion of a stretch of two or more nucleotides. By selecting for those members of the virus mixture that stably replicate at a reduced temperature, a virus with a cold-adaptation phenotype is selected. As used herein, a "phenotype" is an observable or measurable characteristic of a biological entity such as a cell or a virus, where the observed characteristic is attributable to a specific genetic configuration of that biological entity, i.e., a certain genotype. As such, a cold-adaptation phenotype is the result of one or more mutations in the virus genome. As used herein, the terms "a mutation," "a genome," "a genotype," or "a phenotype" refer to one or more, or at least one mutation, genome, genotype, or phenotype, respectively.

Additional, observable phenotypes in a cold-adapted equine influenza virus may occur, and will generally be the result of one or more additional mutations in the genome of such a virus. For example, a cold-adapted equine influenza virus of the present invention may, in addition, be attenuated, exhibit dominant interference, and/or be temperature sensitive.

In one embodiment, a cold-adapted equine influenza virus of the present invention has a phenotype characterized by attenuation. A cold-adapted equine influenza virus is "attenuated," when administration of the virus to an equine influenza virus-susceptible animal results in reduced or absent clinical signs in that animal, compared to clinical signs observed in animals that are infected with wild-type equine influenza virus. For example, an animal infected with wild-type equine influenza virus will display fever, sneezing, coughing, depression, and nasal discharges. In contrast, an animal administered an attenuated, cold-adapted equine influenza virus of the present invention will display minimal or no, i.e., undetectable, clinical disease signs.

In another embodiment, a cold-adapted equine influenza virus of the present invention comprises a temperature sensitive phenotype. As used herein, a temperature sensitive cold-adapted equine influenza virus replicates at reduced temperatures, but no longer replicates or forms plaques in tissue culture cells at certain higher growth temperatures at which the wild-type virus will replicate and form plaques. While not being bound by theory, it is believed that replication of equine influenza viruses with a temperature sensitive phenotype is largely restricted to the cool passages of the upper respiratory tract, and does not replicate efficiently in the lower respiratory tract, where the virus is more prone to cause disease symptoms. A temperature at which a temperature sensitive virus will grow is referred to herein as a "permissive" temperature for that temperature sensitive virus, and a higher temperature at which the temperature sensitive virus will not grow, but at which a corresponding wild-type virus will grow, is referred to herein as a "non-permissive" temperature for that temperature sensitive virus. For example, certain temperature sensitive cold-adapted equine influenza viruses of the present invention replicate in embryonated chicken eggs at a temperature at or below about 30° C., preferably at about 28° C. or about 26° C., and will form plaques in tissue culture cells at a permissive temperature of about 34° C., but will not form plaques in tissue culture cells at a non-permissive temperature of about 39° C. Other temperature sensitive cold-adapted equine influenza viruses of the present invention replicate in embryonated chicken eggs at a temperature at or below about 30° C., preferably at about 28° C. or about 26° C., and will form plaques in tissue culture cells at a permissive temperature of about 34° C., but will not form plaques in tissue culture cells at a non-permissive temperature of about 37° C.

Certain cold-adapted equine influenza viruses of the present invention have a dominant interference phenotype; that is, they dominate an infection when co-infected into cells with another influenza A virus, thereby impairing the growth of that other virus. For example, when a cold-adapted equine influenza virus of the present invention, having a dominant interference phenotype, is co-infected into MDCK cells with the wild-type parental equine influenza virus, A/equine/Kentucky/1/91 (H3N8), growth of the parental virus is impaired. Thus, in an animal that has recently been exposed to, or may be soon exposed to, a virulent influenza virus, i.e., an influenza virus that causes disease symptoms, administration of a therapeutic composition comprising a cold-adapted equine influenza virus having a dominant interference phenotype into the upper respiratory tract of that animal will impair the growth of the virulent virus, thereby ameliorating or reducing disease in that animal, even in the absence of an immune response to the virulent virus.

Dominant interference of a cold-adapted equine influenza virus having a temperature sensitive phenotype can be measured by standard virological methods. For example, separate monolayers of MDCK cells can be infected with (a) a virulent wild-type influenza A virus, (b) a temperature sensitive, cold-adapted equine influenza virus, and (c) both viruses in a co-infection, with all infections done at multiplicities of infection (MOI) of about 2 plaque forming units (pfu) per cell. After infection, the virus yields from the various infected cells are measured by duplicate plaque assays performed at the permissive temperature for the cold-adapted equine influenza virus and at the non-permissive temperature of that virus. A cold adapted equine influenza virus having a temperature sensitive phenotype is unable to form plaques at its non-permissive temperature, while the wild-type virus is able to form plaques at both the permissive and non-permissive temperatures. Thus it is possible to measure the growth of the wild-type virus in the presence of the cold adapted virus by comparing the virus yield at the non-permissive temperature of the cells singly infected with wild-type virus to the yield at the non-permissive temperature of the wild-type virus in doubly infected cells.

Cold-adapted equine influenza viruses of the present invention are characterized primarily by one or more of the following identifying phenotypes: cold-adaptation, temperature sensitivity, dominant interference, and/or attenuation. As used herein, the phrase "an equine influenza virus comprises the identifying phenotype(s) of cold-adaptation, temperature sensitivity, dominant interference, and/or attenuation" refers to a virus having such a phenotype(s). Examples of such viruses include, but are not limited to, EIV-P821, identified by accession No. ATCC VR 2625, EIV-P824, identified by accession No. ATCC VR 2624, and EIV-MSV+5, identified by accession No. ATCC VR 2627, as well as EIV-MSV0, EIV, MSV+1, EIV-MSV+2, EIV-MSV+3, and EIV-MSV+4. Production of such viruses is described in the examples. For example, cold-adapted equine influenza virus EIV-P821 is characterized by, i.e., has the identifying phenotypes of, (a) cold-adaptation, e.g., its ability to replicate in embryonated chicken eggs at a temperature of about 26° C.; (b) temperature sensitivity, e.g., its inability to form plaques in tissue culture cells and to express late gene products at a non-permissive temperature of about 37° C., and its inability to form plaques in tissue culture cells and to synthesize any viral proteins at a non-permissive temperature of about 39° C.; (c) its attenuation upon administration to an equine influenza virus-susceptible animal; and (d) dominant interference, e.g., its ability, when co-infected into a cell with a wild-type influenza A virus, to interfere with the growth of that wild-type virus. Similarly, cold-adapted equine influenza virus EIV-P824 is characterized by (a) cold adaptation, e.g., its ability to replicate in embryonated chicken eggs at a temperature of about 28° C.; (b) temperature sensitivity, e.g., its inability to form plaques in tissue culture cells at a non-permissive temperature of about 39° C.; and (c) dominant interference, e.g., its ability, when co-infected into a cell with a wild-type influenza A virus, to interfere with the growth of that wild-type virus. In another example, cold-adapted equine influenza virus EIV-MSV+5 is characterized by (a) cold-adaptation, e.g., its ability to replicate in embryonated chicken eggs at a temperature of about 26° C.; (b) temperature sensitivity, e.g., its inability to form plaques in tissue culture cells at a non-permissive temperature of about 39° C.; and (c) its attenuation upon administration to an equine influenza virus-susceptible animal.

In certain cases, the RNA segment upon which one or more mutations associated with a certain phenotype occur may be determined through reassortment analysis by standard methods, as disclosed herein. In one embodiment, a cold-adapted equine influenza virus of the present invention comprises a temperature sensitive phenotype that correlates with at least two mutations in the genome of that virus. In this embodiment, one of the two mutations, localized by reassortment analysis as disclosed herein, inhibits, i.e., blocks or prevents, the ability of the virus to form plaques in tissue culture cells at a non-permissive temperature of about 39° C. This mutation co-segregates with the segment of the equine influenza virus genome that encodes the nucleoprotein (NP) gene of the virus, i.e., the mutation is located on the same RNA segment as the NP gene. In this embodiment, the second mutation inhibits all protein synthesis at a non-permissive temperature of about 39° C. As such, at the non-permissive temperature, the virus genome is incapable of expressing any viral proteins. Examples of cold-adapted equine influenza viruses possessing these characteristics are EIV-P821 and EIV MSV+5. EIV-P821 was generated by serial passaging of a wild-type equine influenza virus in embryonated chicken eggs by methods described in Example 1A. EIV-MSV+5 was derived by further serial passaging of EIV-P821, as described in Example 1E.

Furthermore, a cold-adapted, temperature sensitive equine influenza virus comprising the two mutations which inhibit plaque formation and viral protein synthesis at a non-permissive temperature of about 39° C. can comprise one or more additional mutations, which inhibit the virus' ability to synthesize late gene products and to form plaques in tissue culture cells at a non-permissive temperature of about 37° C. An example of a cold-adapted equine influenza virus possessing these characteristics is EIV-P821. This virus isolate replicates in embryonated chicken eggs at a temperature of about 26° C., and does not form plaques or express any viral proteins at a temperature of about 39° C. Furthermore, EIV-P821 does not form plaques on MDCK cells at a non-permissive temperature of about 37° C., and at this temperature, late gene expression is inhibited in such a way that late proteins are not produced, i.e., normal levels of NP protein are synthesized, reduced or undetectable levels of M1 or HA proteins are synthesized, and enhanced levels of the polymerase proteins are synthesized. Since this phenotype is typified by differential viral protein synthesis, it is distinct from the protein synthesis phenotype seen at a non-permissive temperature of about 39° C., which is typified by the inhibition of synthesis of all viral proteins.

Pursuant to 37 CFR § 1.802 (a-c), cold-adapted equine influenza viruses, designated herein as EIV-P821, an EIV-P824 were deposited with the American Type Culture Collection (ATCC, 10801 University Boulevard, Manassas, Va. 20110-2209) under the Budapest Treaty as ATCC Accession Nos. ATCC VR-2625, and ATCC VR-2624, respectively, on Jul. 11, 1998. Cold-adapted equine influenza virus EIV-MSV+5 was deposited with the ATCC as ATCC Accession No. ATCC VR-2627 on Aug. 3, 1998. Pursuant to 37 CFR§ 1.806, the deposits are made for a term of at least thirty (30) years and at least Five (5) years after the most recent request for the furnishing of a sample of the deposit was received by the depository. Pursuant to 37 CFR § 1.808 (a)(2), all restrictions imposed by the depositor on the availability to the public will be irrevocably removed upon the granting of the patent.

Preferred cold-adapted equine influenza viruses of the present invention have the identifying phenotypes of EIV-P821, EIV-P824, and EIV-MSV+5. Particularly preferred cold-adapted equine influenza viruses include EIV-P821, EIV-P824, EIV-MSV+5, and progeny of these viruses. As used herein, "progeny" are "offspring," and as such can slightly altered phenotypes compared to the parent virus, but retain identifying phenotypes of the parent virus, for example, cold-adaptation, temperature sensitivity, dominant interference, or attenuation. For example, cold-adapted equine influenza virus EIV-MSV+5 is a "progeny" of cold-adapted equine influenza virus EIV-P821. "Progeny" also include reassortant influenza A viruses that comprise one or more identifying phenotypes of the donor parent virus.

Reassortant influenza A viruses of the present invention are produced by genetic reassortment of the genome segments of a donor cold-adapted equine influenza virus of the present invention with the genome segments of a recipient influenza A virus, and then selecting a reassortant virus that derives at least one of its eight RNA genome segments from the donor virus, such that the reassortant virus acquires at least one identifying phenotype of the donor cold-adapted equine influenza virus. Identifying phenotypes include cold-adaptation, temperature sensitivity, attenuation, and dominant interference. Preferably, reassortant influenza A viruses of the present invention derive at least the attenuation phenotype of the donor virus. Methods to isolate reassortant influenza viruses are well known to those skilled in the art of virology and are disclosed, for example, in Fields, et al., 1996, *Fields Virology*, 3d ed., Lippincott-Raven; and Palese, et al., 1976, *J. Virol.*, 17, 876-884. Fields, et al., ibid. and Palese, et al., ibid.

A suitable donor equine influenza virus is a cold-adapted equine influenza virus of the present invention, for example, EIV-P821, identified by accession No. ATCC VR 2625, EIV-P824, identified by accession No. ATCC VR 2624, or EIV-MSV+5, identified by accession No. ATCC VR 2627. A suitable recipient influenza A virus can be another equine influenza virus, for example a Eurasian subtype 2 equine influenza virus such as A/equine/Suffolk/89 (H3N8) or a subtype 1 equine influenza virus such as A/Prague/1/56 (H7N7). A recipient influenza A virus can also be any influenza A virus capable of forming a reassortant virus with a donor cold-adapted equine influenza virus. Examples of such influenza A viruses include, but are not limited to, human influenza viruses such as A/Puerto Rico/8/34 (H1N1), A/Hong Kong/156/97 (H5N1), A/Singapore/1/57 (H2N2), and A/Hong Kong/1/68 (H3N2); swine viruses such as A/Swine/Iowa/15/30 (H1N1); and avian viruses such as A/mallard/New York/6750/78 (H2N2) and A/chicken/Hong Kong/258/97 (H5N1). A reassortant virus of the present invention can include any combination of donor and recipient gene segments, as long as the resulting reassortant virus possesses at least one identifying phenotype of the donor virus.

One example of a reassortant virus of the present invention is a "6+2" reassortant virus, in which the six "internal gene segments," i.e., those comprising the NP, PB2, PB1, PA, M, and NS genes, are derived from the donor cold-adapted equine influenza virus genome, and the two "external gene segments," i.e., those comprising the HA and NA genes, are derived from the recipient influenza A virus. A resultant virus thus produced has the attenuated, cold-adapted, temperature sensitive, and/or dominant interference phenotypes of the donor cold-adapted equine influenza virus, but the antigenicity of the recipient strain.

In yet another embodiment, a cold-adapted equine influenza virus of the present invention can be produced through recombinant means. In this approach, one or more specific mutations, associated with identified cold-adaptation, attenuation, temperature sensitivity, or dominant interference phenotypes, are identified and are introduced back into a wild-type equine influenza virus strain using a reverse genetics approach. Reverse genetics entails using RNA polymerase complexes isolated from influenza virus-infected cells to transcribe artificial influenza virus genome segments containing the mutation(s), incorporating the synthesized RNA segment(s) into virus particles using a helper virus, and then selecting for viruses containing the desired changes. Reverse genetics methods for influenza viruses are described, for example, in Enami, et al., 1990, *Proc. Natl. Acad. Sci.* 87, 3802-3805; and in U.S. Pat. No. 5,578,473, by Palese, et al., issued Nov. 26, 1996. This approach allows one skilled in the art to produce additional cold-adapted equine influenza viruses of the present invention without the need to go through the lengthy cold-adaptation process, and the process of selecting mutants both in vitro and in vivo with the desired virus phenotype.

A cold-adapted equine influenza virus of the present invention may be propagated by standard virological methods well-known to those skilled in the art, examples of which are disclosed herein. For example, a cold-adapted equine influenza virus can be grown in embryonated chicken eggs or in eukaryotic tissue culture cells. Suitable continuous eukaryotic cell lines upon which to grow a cold-adapted equine influenza virus of the present invention include those that support growth of influenza viruses, for example, MDCK cells. Other suitable cells upon which to grow a cold-adapted equine influenza virus of the present invention include, but are not limited to, primary kidney cell cultures of monkey, calf, hamster or chicken.

In one embodiment, the present invention provides a therapeutic composition to protect an animal against disease caused by an influenza A virus, where the therapeutic composition includes either a cold-adapted equine influenza virus or a reassortant influenza A virus comprising at least one genome segment of an equine influenza virus generated by cold-adaptation, wherein the equine influenza virus genome segment confers at least one identifying phenotype of the cold-adapted equine influenza virus. In addition, a therapeutic composition of the present invention can include an equine influenza virus that has been genetically engineered to comprise one or more mutations, where those mutations have been identified to confer a certain identifying phenotype on a cold-adapted equine influenza virus of the present invention. As used herein, the phrase "disease caused by an influenza A virus" refers to the clinical manifestations observed in an animal which has been infected with a virulent influenza A virus. Examples of such clinical manifestations include, but are not limited to, fever, sneezing, coughing, nasal discharge, rales, anorexia and depression. In addition, the phrase "disease caused by an influenza A virus" is defined herein to include shedding of virulent virus by the infected animal. Verification that clinical manifestations observed in an animal correlate with infection by virulent equine influenza virus may be made by several methods, including the detection of a specific antibody and/or T-cell responses to equine influenza virus in the animal. Preferably, verification that clinical manifestations observed in an animal correlate with infection by a virulent influenza A virus is made by the isolation of the virus from the afflicted animal, for example, by swabbing the nasopharyngeal cavity of that animal for virus-containing secretions. Verification of virus isolation may be made by the detection of CPE in tissue culture cells inoculated with the isolated secretions, by inoculation of the isolated secretions into embryonated chicken eggs, where virus replication is detected by the ability of AF from the inoculated eggs to agglutinate erythrocytes, suggesting the presence of the influenza virus hemagglutinin protein, or by use of a commercially available diagnostic test, for example, the Directigen® FLU A test.

As used herein, the term "to protect" includes, for example, to prevent or to treat influenza A virus infection in the subject animal. As such, a therapeutic composition of the present invention can be used, for example, as a prophylactic vaccine to protect a subject animal from influenza disease by administering the therapeutic composition to that animal at some time prior to that animal's exposure to the virulent virus.

A therapeutic composition of the present invention, comprising a cold-adapted equine influenza virus having a dominant interference phenotype, can also be used to treat an animal that has been recently infected with virulent influenza A virus or is likely to be subsequently exposed in a few days, such that the therapeutic composition immediately interferes with the growth of the virulent virus, prior to the animal's production of antibodies to the virulent virus. A therapeutic composition comprising a cold-adapted equine influenza virus having a dominant interference phenotype may be effectively administered prior to subsequent exposure for a length of time corresponding to the approximate length of time that a cold-adapted equine influenza virus of the present invention will replicate in the upper respiratory tract of a treated animal, for example, up to about seven days. A therapeutic composition comprising a cold-adapted equine influenza virus having a dominant interference phenotype may be effectively administered following exposure to virulent equine influenza virus for a length of time corresponding to the time required for an infected animal to show disease symptoms, for example, up to about two days.

Therapeutic compositions of the present invention can be administered to any animal susceptible to influenza virus disease, for example, humans, swine, horses and other equids, aquatic birds, domestic and game fowl, seals, mink, and whales. Preferably, a therapeutic composition of the present invention is administered equids. Even more preferably, a therapeutic composition of the present invention is administered to a horse, to protect against equine influenza disease.

Current vaccines available to protect horses against equine influenza virus disease are not effective in protecting young foals, most likely because they cannot overcome the maternal antibody present in these young animals, and often, vaccination at an early age, for example 3 months of age, can lead to tolerance rather than immunity. In one embodiment, and in contrast to existing equine influenza virus vaccines, a therapeutic composition comprising a cold-adapted equine influenza virus of the present invention apparently can produce immunity in young animals. As such, a therapeutic composition of the present invention can be safely and effectively administered to young foals, as young as about 3 months of age, to protect against equine influenza disease without the induction of tolerance.

In one embodiment, a therapeutic composition of the present invention can be multivalent. For example, it can protect an animal from more than one strain of influenza A virus by providing a combination of one or more cold-adapted equine influenza viruses of the present invention, one or more reassortant influenza A viruses, and/or one or more genetically-engineered equine influenza viruses of the present invention. Multivalent therapeutic compositions can include at least two cold-adapted equine influenza viruses, e.g., against North American subtype-2 virus isolates such as A/equine/Kentucky/1/91 (H1N8), and Eurasian subtype-2 virus isolates such as A/equine/Suffolk/89 (H3N8); or one or more subtype-2 virus isolates and a subtype-1 virus isolate such as A/equine/Prague/1/56 (H7N7). Similarly, a multivalent therapeutic composition of the present invention can include a cold-adapted equine influenza virus and a reassortant influenza A virus of the present invention, or two reassortant influenza A viruses of the present invention. A multivalent therapeutic composition of the present invention can also contain one or more formulations to protect against one or more other infectious agents in addition to influenza A virus. Such other infectious agents include, but not limited to: viruses; bacteria; fungi and fungal-related microorganisms; and parasites. Preferable multivalent therapeutic compositions include, but are not limited to, a cold-adapted equine influenza virus, reassortant influenza A virus, or genetically-engineered equine influenza virus of the present invention plus one or more compositions protective against one or more other infectious agents that afflict horses. Suitable infectious agents to protect against include, but are not limited to, equine infectious anemia virus, equine herpes virus, eastern, western, or Venezuelan equine encephalitis virus, tetanus, *Streptococcus equi*, and *Ehrlichia resticii*.

A therapeutic composition of the present invention can be formulated in an excipient that the animal to be treated can tolerate. Examples of such excipients include water, saline, Ringer's solution, dextrose solution, Hank's solution, and other aqueous physiologically balanced salt solutions. Excipients can also contain minor amounts of additives, such as substances that enhance isotonicity and chemical or biological stability. Examples of buffers include phosphate buffer, bicarbonate buffer, and Tris buffer, while examples of stabilizers include A1/A2 stabilizer, available from Diamond Animal Health, Des Moines, Iowa. Standard formulations can either be liquids or solids which can be taken up in a suitable liquid as a suspension or solution for administration to an animal. In one embodiment, a non-liquid formulation may comprise the excipient salts, buffers, stabilizers, etc., to which sterile water or saline can be added prior to administration.

A therapeutic composition of the present invention may also include one or more adjuvants or carriers. Adjuvants are typically substances that enhance the immune response of an animal to a specific antigen, and carriers include those compounds that increase the half-life of a therapeutic composition in the treated animal. One advantage of a therapeutic composition comprising a cold-adapted equine influenza virus or a reassortant influenza A virus of the present invention is that adjuvants and carriers are not required to produce an efficacious vaccine. Furthermore, in many cases known to those skilled in the art, the advantages of a therapeutic composition of the present invention would be hindered by the use of some adjuvants or carriers. However, it should be noted that use of adjuvants or carriers is not precluded by the present invention.

Therapeutic compositions of the present invention include an amount of a cold-adapted equine influenza virus that is sufficient to protect an animal from challenge with virulent equine influenza virus. In one embodiment, a therapeutic composition of the present invention can include an amount of a cold-adapted equine influenza virus ranging from about $10^5$ tissue culture infectious dose-50 ($TCID_{50}$) units of virus to about $10^8$ $TCTD_{50}$ units of virus. As used herein, a "$TCID_{50}$ unit" is amount of a virus which results in cytopathic effect in 50% of those cell cultures infected. Methods to measure and calculate $TCID_{50}$ are known to those skilled in the art and are available, for example, in Reed and Muench, 1938, *Am. J. of Hyg.* 27, 493-497. A preferred therapeutic composition of the present invention comprises from about $10^6$ $TCID_{50}$ units to about $10^7$ $TCID_{50}$ units of a cold-adapted equine influenza virus or reassortant influenza A virus of the present invention. Even more preferred is a therapeutic composition comprising about $2 \times 10^6$ $TCID_{50}$ units of a cold-adapted equine influenza virus or reassortant influenza A virus of the present invention.

The present invention also includes methods to protect an animal against disease caused by an influenza A virus comprising administering to the animal a therapeutic composition of the present invention. Preferred are those methods which protect an equid against disease caused by equine influenza virus, where those methods comprise administering to the equid a cold-adapted equine influenza virus. Acceptable protocols to administer therapeutic compositions in an effective manner include individual dose size, number of doses, frequency of dose administration, and mode of administration. Determination of such protocols can be accomplished by those skilled in the art, and examples are disclosed herein.

A preferable method to protect an animal against disease caused by an influenza A virus includes administering to that animal a single dose of a therapeutic composition comprising a cold-adapted equine influenza virus, a reassortant influenza A virus, or genetically-engineered equine influenza virus of the present invention. A suitable single dose is a dose that is capable of protecting an animal from disease when administered one or more times over a suitable time period. The method of the present invention may also include administering subsequent, or booster doses of a therapeutic composition. Booster administrations can be given from about 2 weeks to several years after the original administration. Booster administrations preferably are administered when the immune response of the animal becomes insufficient to protect the animal from disease. Examples of suitable and preferred dosage schedules are disclosed in the Examples section.

A therapeutic composition of the present invention can be administered to an animal by a variety of means, such that the virus will enter and replicate in the mucosal cells in the upper respiratory tract of the treated animal. Such means include, but are not limited to, intranasal administration, oral administration, and intraocular administration. Since influenza viruses naturally infect the mucosa of the upper respiratory tract, a preferred method to administer a therapeutic composition of the present invention is by intranasal administration. Such administration may be accomplished by use of a syringe fitted with cannula, or by use of a nebulizer fitted over the nose and mouth of the animal to be vaccinated.

The efficacy of a therapeutic composition of the present invention to protect an animal against disease caused by influenza A virus can be tested in a variety of ways including, but not limited to, detection of antibodies by, for example, hemagglutination inhibition (HAI) tests, detection of cellular immunity within the treated animal, or challenge of the treated animal with virulent equine influenza virus to determine whether the treated animal is resistant to the development of disease. In addition, efficacy of a therapeutic composition of the present invention comprising a cold-adapted equine influenza virus having a dominant interference phenotype to ameliorate or reduce disease symptoms in an animal previously inoculated or susceptible to inoculation with a virulent, wild-type equine influenza virus can be tested by screening for the reduction or absence of disease symptoms in the treated animal.

The present invention also includes methods to produce a therapeutic composition of the present invention. Suitable and preferred methods for making a therapeutic composition of the present invention are disclosed herein. Pertinent steps involved in producing one type of therapeutic composition of the present invention, i.e., a cold-adapted equine influenza virus, include (a) passaging a wild-type equine influenza virus in vitro, for example, in embryonated chicken eggs; (b) selecting viruses that grow at a reduced temperature; (c) repeating the passaging and selection steps one or more times, at progressively lower temperatures, until virus populations are selected which stably grow at the desired lower temperature; and (d) mixing the resulting virus preparation with suitable excipients.

The pertinent steps involved in producing another type of therapeutic composition of the present invention, i.e., a reassortant influenza A virus having at least one genome segment of an equine influenza virus generated by adaptation, includes the steps of (a) mixing the genome segments of a donor cold-adapted equine influenza virus, which preferably also has the phenotypes of attenuation, temperature sensitivity, or dominant interference, with the genome segments of a recipient influenza A virus, and (b) selecting reassortant viruses that have at least one identifying phenotype of the donor equine influenza virus. Identifying phenotypes to select for include attenuation, cold-adaptation, temperature sensitivity, and dominant interference. Methods to screen for these phenotypes are well known to those skilled in the art, and are disclosed herein. It is preferable to screen for viruses that at least have the phenotype of attenuation.

Using this method to generate a reassortant influenza A virus having at least one genome segment of a equine influenza virus generated by cold-adaptation, one type of reassortant virus to select for is a "6+2" reassortant, where the six "internal gene segments," i.e., those coding for the NP, PB2, PB1, PA, M, and NS genes, are derived from the donor cold-adapted equine influenza virus genome, and the two "external gene segments," i.e., those coding for the HA and NA genes, are derived from the recipient influenza A virus. A resultant virus thus produced can have the cold-adapted, attenuated, temperature sensitive, and/or interference phenotypes of the donor cold-adapted equine influenza virus, but the antigenicity of the recipient strain.

The present invention includes nucleic acid molecules isolated from equine influenza virus wild type strain A/equine/Kentucky/1/91 (H3N8), and cold-adapted equine influenza virus EIV-P821.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified.

The present invention includes nucleic acid molecules encoding wild-type and cold-adapted equine influenza virus proteins. Nucleic acid molecules of the present invention can be prepared by methods known to one skilled in the art. Proteins of the present invention can be prepared by methods known to one skilled in the art, i.e., recombinant DNA technology. Preferred nucleic acid molecules have coding strands comprising nucleic acid sequences SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:21, SEQ ID NO:22, SEQ ID NO:23, SEQ ID NO:25, and/or a complement thereof. Complements are defined as two single strands of nucleic acid in which the nucleotide sequence is such that they will hybridize as a result of base pairing throughout their full length. Given a nucleotide sequence, one of ordinary skill in the art can deduce the complement.

Preferred nucleic acid molecules encoding equine influenza M proteins are $nei_{wt}M_{1023}$, $nei_{wt1}M_{1023}$, $nei_{wt2}M_{1023}$, $nei_{wt}M_{756}$, $nei_{wt1}M_{756}$, $nei_{wt2}M_{756}$, $nei_{ca1}M_{1023}$, $nei_{ca2}M_{1023}$, $nei_{ca1}M_{756}$ and/or $ne_{ca2}M_{756}$, the coding strands of which are represented by SEQ ID NO:1, SEQ ID NO:3, SEQ ID NO:4, and/or SEQ ID NO:6.

Preferred nucleic acid molecules encoding equine influenza HA proteins are $nei_{wt}HA_{1762}$, $nei_{wt}HA_{1695}$, $nei_{ca1}HA_{1762}$, $nei_{ca2}HA_{1762}$, $nei_{ca1}HA_{1695}$, and/or $nei_{ca2}HA_{1695}$, the coding strands of which are represented by SEQ ID NO:7, SEQ ID NO:9, SEQ ID NO:10, and/or SEQ ID NO:12.

Preferred nucleic acid molecules encoding equine influenza PB2-N proteins are $nei_{wt}PB2-N_{1241}$, $nei_{wt}PB2-N_{1214}$, nei$_{ca1}$PB2-N$_{1241}$ nei$_{ca2}$PB2-N$_{1241}$, nei$_{ca1}$PB2-N$_{1214}$ nei$_{ca2}$, and/or PB2-N$_{1214}$, the coding strands of which are represented by SEQ ID NO:13, SEQ ID NO:15, SEQ ID NO:16, and/or SEQ ID NO:18.

Preferred nucleic acid molecules encoding equine influenza PB2-C proteins are nei$_{wt1}$PB2-C$_{1233}$, nei$_{wt2}$PB2-C$_{1232}$, nei$_{wt}$PB2-C$_{1194}$, nei$_{ca1}$PB2-C$_{1232}$, nei$_{ca2}$PB2-C$_{1231}$, and/or nei$_{ca1}$PB2-C$_{1194}$, the coding strands of which are represented by SEQ ID NO:19, SEQ ID NO:22, SEQ ID NO:21, SEQ ID NO:23, and/or SEQ ID NO:25.

The present invention includes proteins comprising SEQ ID NO:2, SEQ ID NO:5, SEQ ID NO:8, SEQ ID NO:11, SEQ ID NO:14, SEQ ID NO:17, SEQ ID NO:20 and/or SEQ ID NO:24 as well as nucleic acid molecules encoding such proteins.

Preferred equine influenza M proteins of the present invention include proteins encoded by a nucleic acid molecule comprising nei$_{wt}$M$_{1023}$, nei$_{wt1}$M$_{1023}$, nei$_{wt2}$M$_{1023}$, nei$_{wt}$M$_{756}$, nei$_{wt1}$M$_{756}$, nei$_{wt2}$M$_{756}$, nei$_{ca1}$M$_{1023}$, nei$_{ca2}$M$_{1023}$, nei$_{ca1}$M$_{756}$, and/or nei$_{ca2}$M$_{756}$. Preferred equine influenza M proteins are Pei$_{wt}$M$_{252}$, Pei$_{ca1}$M$_{252}$, and/or Pei$_{ca2}$M$_{252}$. In one embodiment, a preferred equine influenza M protein of the present invention is encoded by SEQ ID NO:1, SEQ ID NO:3, SEQ ID NO:4, and/or SEQ ID NO:6, and, as such, has an amino acid sequence that includes SEQ ID NO:2 and/or SEQ ID NO:5.

Preferred equine influenza HA proteins of the present invention include proteins encoded by a nucleic acid molecule comprising nei$_{wt}$HA$_{1762}$ nei$_{wt}$HA$_{1695}$, nei$_{ca1}$HA$_{1762}$, nei$_{ca2}$HA$_{1762}$, nei$_{ca1}$HA$_{1695}$, and/or nei$_{ca2}$HA$_{1695}$. Preferred equine influenza HA proteins are P Pei$_{wt}$HA$_{565}$, Pei$_{ca1}$HA$_{565}$, and/or Pei$_{ca2}$HA$_{565}$. In one embodiment, a preferred equine influenza HA protein of the present invention is encoded by SEQ ID NO:7, SEQ ID NO:9, SEQ ID NO:10, and/or SEQ ID NO:12, and, as such, has an amino acid sequence that includes SEQ ID NO: 8 and/or SEQ ID NO:11.

Preferred equine influenza PB2-N proteins of the present invention include proteins encoded by a nucleic acid molecule comprising nei$_{wt}$PB2-N$_{1241}$, nei$_{wt}$PB2-N$_{1214}$, nei$_{ca1}$PB2-N$_{1241}$, nei$_{ca2}$PB2-N$_{1241}$, nei$_{ca1}$PB2-N$_{1214}$ nei$_{ca2}$, and/or PB2-N$_{1214}$. Preferred equine influenza PB2-N proteins are P$_{wt}$PB2-N$_{404}$, P$_{ca1}$PB2-N$_{404}$, and/or P$_{ca2}$PB2-N$_{404}$. In one embodiment, a preferred equine influenza PB2-N protein of the present invention is encoded by SEQ ID NO:13, SEQ ID NO:15, SEQ ID NO:16, and/or SEQ ID NO:18, and, as such, has an amino acid sequence that includes SEQ ID NO:14 and/or SEQ ID NO:17.

Preferred equine influenza PB2-C proteins of the present invention include proteins encoded by a nucleic acid molecule comprising nei$_{wt1}$PB2-C$_{1233}$, nei$_{wt2}$PB2-C$_{1232}$, nei$_{wt}$PB2-C$_{1194}$, nei$_{ca1}$PB2-C$_{1232}$, nei$_{ca2}$PB2-C$_{1231}$, and/or nei$_{ca1}$PB2-C$_{1194}$. Preferred equine influenza PB2-N proteins are P$_{wt}$PB2-C$_{398}$, P$_{ca1}$PB2-C$_{398}$, and/or P$_{ca2}$PB2-C$_{398}$. In one embodiment, a preferred equine influenza PB2-C protein of the present invention is encoded by SEQ ID NO:19, SEQ ID NO:22, SEQ ID NO:21, SEQ ID NO:23, and/or SEQ ID NO:25, and, as such, has an amino acid sequence that includes SEQ ID NO:20 and/or SEQ ID NO:24.

Nucleic acid sequence SEQ ID NO:1 represents the consensus sequence deduced from the coding strand of PCR amplified nucleic acid molecules denoted herein as nei$_{wt}$M$_{1023}$ and nei$_{wt2}$M$_{1023}$, the production of which is disclosed in the Examples. Nucleic acid sequence SEQ ID NO:4 represents the deduced sequence of the coding strand of PCR amplified nucleic acid molecules denoted herein as nei$_{ca1}$M$_{1023}$ and nei$_{ca2}$M$_{1023}$, the production of which is disclosed in the Examples. Nucleic acid sequence SEQ ID NO:7 represents the deduced sequence of the coding strand of a PCR amplified nucleic acid molecule denoted herein as nei$_{wt}$HA$_{1762}$, the production of which is disclosed in the Examples. Nucleic acid sequence SEQ ID NO:10 represents the deduced sequence of the coding strand of PCR amplified nucleic acid molecules denoted herein as nei$_{ca1}$HA$_{1762}$ and nei$_{ca2}$HA$_{1762}$, the production of which is disclosed in the Examples. Nucleic acid sequence SEQ ID NO:13 represents the deduced sequence of the coding strand of a PCR amplified nucleic acid molecule denoted herein as nei$_{wt}$PB2-N$_{1241}$, the production of which is disclosed in the Examples. Nucleic acid sequence SEQ ID NO:16 represents the deduced sequence of the coding strand of PCR amplified nucleic acid molecules denoted herein as nei$_{ca1}$PB2-N$_{1241}$ and nei$_{ca2}$PB2-N$_{1241}$, the production of which is disclosed in the Examples. Nucleic acid sequence SEQ ID NO:19 represents the deduced sequence of the coding strand of a PCR amplified nucleic acid molecule denoted herein as nei$_{wt1}$PB2-C$_{1233}$, the production of which is disclosed in the examples.

Nucleic acid sequence SEQ ID NO:22 represents the deduced sequence of the coding strand of a PCR amplified nucleic acid molecule denoted herein as nei$_{wt2}$PB2-C$_{1232}$, the production of which is disclosed in the examples. Nucleic acid sequence SEQ ID NO:23 represents the deduced sequence of the coding strand of a PCR amplified nucleic acid molecule denoted herein as nei$_{ca1}$PB2-C$_{1232}$, the production of which is disclosed in the examples. Additional nucleic acid molecules, nucleic acid sequences, proteins and amino acid sequences are described in the Examples.

The present invention includes nucleic acid molecule comprising a cold-adapted equine influenza virus encoding an M protein having an amino acid sequence comprising SEQ ID NO:5. Another embodiment of the present invention includes a nucleic acid molecule comprising a cold-adapted equine influenza virus encoding an HA protein having an amino acid sequence comprising SEQ ID NO:11. Another embodiment of the present invention includes a nucleic acid molecule comprising a cold-adapted equine influenza virus encoding a PB2-N protein having an amino acid sequence comprising SEQ ID NO:17. Another embodiment of the present invention includes a nucleic acid molecule comprising a cold-adapted equine influenza virus encoding a PB2-C protein having an amino acid sequence comprising SEQ ID NO:24.

It should be noted that since nucleic acid sequencing technology is not entirely error-free, the nucleic acid sequences and amino acid sequences presented herein represent, respectively, apparent nucleic acid sequences of nucleic acid molecules of the present invention and apparent amino acid sequences of M, HA, and PB2-N, and PB2-C proteins of the present invention.

Another embodiment of the present invention is an antibody that selectively binds to an wild-type virus M, HA, PB2-N, PB2-C, PB2, protein of the present invention. Another embodiment of the present invention is an antibody that selectively binds to a cold-adapted virus M, HA, PB2-N, PB2-C, PB2, protein of the present invention. Preferred antibodies selectively bind to SEQ ID NO:2, SEQ ID NO:5, SEQ ID NO:8, SEQ ID NO:11, SEQ ID NO:14, SEQ ID NO:17, SEQ ID NO:20 and/or SEQ ID NO:24.

The following examples are provided for the purposes of illustration and are not intended to limit the scope of the present invention.

EXAMPLE 1

This example discloses the production and phenotypic characterization of several cold-adapted equine influenza viruses of the present invention.

A. Parental equine influenza virus, A/equine/Kentucky/1/91 (H3N8) (obtained from Tom Chambers, the University of Kentucky, Lexington, Ky.) was subjected to cold-adaptation in a foreign host species, i.e., embryonated chicken eggs, in the following manner. Embryonated, 10 or 11-day old chicken eggs, available, for example, from Truslow Farms, Chestertown, Md. or from HyVac, Adel, Iowa, were inoculated with the parental equine influenza virus by injecting about 0.1 milliliter (ml) undiluted AF containing approximately $10^6$ plaque forming units (pfu) of virus into the allantoic cavity through a small hole punched in the shell of the egg. The holes in the eggs were sealed with nail polish and the eggs were incubated in a humidified incubator set at the appropriate temperature for three days. Following incubation, the eggs were candled and any non-viable eggs were discarded. AF was harvested from viable embryos by aseptically removing a portion of the egg shell, pulling aside the chorioallantoic membrane (CAM) with sterile forceps and removing the AF with a sterile pipette. The harvested AF was frozen between passages. The AF was then used, either undiluted or diluted 1:1000 in phosphate-buffered saline (PBS) as noted in Table 1, to inoculate a new set of eggs for a second passage, and so on. A total of 69 passages were completed. Earlier passages were done at either about 34° C. (passages 1-2) or about 30° C. and on subsequent passages, the incubation temperature was shifted down either to about 28° C., or to about 26° C. In order to increase the possibility of the selection of the desired phenotype of a stable, attenuated virus, the initial serial passage was expanded to included Five different limbs of the serial passage tree, A through E, as shown in Table 1.

TABLE 1

Passage history of the limbs A through E.

| Temperature | Passage # | | | | |
|---|---|---|---|---|---|
| | Limb A | Limb B | Limb C | Limb D | Limb E |
| 34° C. | 1-2 | 1-2 | 1-2 | 1-2 | 1-2 |
| 30° C. | 3-8 | 3-29 | 3-29 | 3-29 | 3-29 |
| 28° C. | | 30-33* | 30-68* | 30-33 | 30-69 |
| 26° C. | 9-65 | 34-69* | | 34-65 | |

*= the infectious allantoic fluid was diluted 1:1000 in these passages

B. Virus isolates carried through the cold-adaptation procedure described in section A were tested for temperature sensitivity, i.e., a phenotype in which the cold-adapted virus grows at the lower, or permissive temperature (e.g., about 34° C.), but no longer forms plaques at a higher, or non-permissive temperature (e.g., about 37° C. or about 39° C.), as follows. At each cold-adaptation passage, the AF was titered by plaque assay at about 34° C. Periodically, individual plaques from the assay were clonally isolated by excision of the plaque area and placement of the excised agar plug in a 96-well tray containing a monolayer of MDCK cells. The 96-well trays were incubated overnight and the yield assayed for temperature sensitivity by CPE assay in duplicate 96-well trays incubated at about 34° C. and at about 39° C. The percent of the clones that scored as temperature sensitive mutants by this assay, i.e., the number of viral plaques that grew at 34° C. but did not grow at 39° C., divided by the total number of plaques, was calculated, and is shown in Table 2.

Temperature sensitive isolates were then evaluated for protein synthesis at the non-permissive temperature by visualization of radiolabeled virus-synthesized proteins by SDS polyacrylamide gel electrophoresis (SDS-PAGE).

TABLE 2

Percent of isolated Clones that were temperature sensitive.

| | Percent Temperature Sensitive | | | | |
|---|---|---|---|---|---|
| Passage# | Limb A | Limb B | Limb C | Limb D | Limb E |
| p36 | 56% | 66% | 0% | 66% | 54% |
| p46 | | 80% | 60% | | 75% |
| p47 | | | 80% | | |
| p48 | | | 100% | | |
| p49 | | 100% | | 100% | 50% |
| p50 | | | 90% | | |
| p51 | | 100% | | | |
| p52 | | | | | 57% |
| p62 | 100% | | | 100% | |
| p65 | | | 100% | | |
| p66 | | 100% | | | 88% |

From the clonal isolates tested for temperature sensitivity, two were selected for further study. Clone EIV-P821 was selected from the 49th passage of limb B and clone EIV-P824 was selected from the 48th passage of limb C as defined in Table 1. Both of these virus isolates were temperature sensitive, with plaque formation of both isolates inhibited at a temperature of about 39° C. At this temperature, protein synthesis was completely inhibited by EIV-P821, but EIV-P824 exhibited normal levels of protein synthesis. In addition, plaque formation by EIV-P821 was inhibited at a temperature of about 37° C., and at this temperature, late gene expression was inhibited, i.e., normal levels of NP protein were synthesized, reduced or no M1 or HA proteins were synthesized, and enhanced levels of the polymerase proteins were synthesized. The phenotype observed at 37° C., being typified by differential viral protein synthesis, was distinct from the protein synthesis phenotype seen at about 39° C., which was typified by the inhibition of synthesis of all viral proteins. Virus EIV-P821 has been deposited with the American Type Culture Collection (ATCC) under Accession No. ATCC VR-2625, and virus EIV-P824 has been deposited with the ATCC under Accession No. ATCC VR-2624.

C. Further characterization of the mutations in isolate EIV-P821 were carried out by reassortment analysis, as follows. Reassortment analysis in influenza viruses allows one skilled in the art, under certain circumstances, to correlate phenotypes of a given virus with putative mutations occurring on certain of the eight RNA segments that comprise an influenza A virus genome. This technique is described, for example, in Palese, et al., ibid. A mixed infection of EIV-P821 and an avian influenza virus, A/mallard/New York/6750/78 was performed as follows. MDCK cells were co-infected with EIV-P821 at a multiplicity of infection (MOI) of 2 pfu/cell and A/mallard/New York/6750/78 at an MOI of either 2, 5, or 10 pfu/cell. The infected cells were incubated at a temperature of about 34° C. The yields of the various co-infections were titered and individual plaques were isolated at about 34° C., and the resultant clonal isolates were characterized as to whether they were able to grow at about 39° C. and about 37° C., and express their genes, i.e., synthesize viral proteins, at about 39° C., about 37° C., and about 34° C. Protein synthesis was evaluated by SDS-PAGE analysis of radiolabeled infected-cell lysates. The HA, NP and NS-1 proteins of the two parent viruses, each of which is encoded by a separate genome segment, were distinguishable by SDS-PAGE analysis, since these particular viral proteins, as derived from either the equine or the avian influenza virus, migrate at different apparent molecular weights. In this way it was possible, at least for the HA, NP, and NS-1 genes, to evaluate whether certain phenotypes of the parent virus, e.g., the temperature sensitive and the protein synthesis phenotypes, co-segregate with the genome segments carrying these genes. The results of the reassortment analyses investigating co-segregation of a) the mutation inhibiting plaque formation, i.e., the induction of CPE, at a non-permissive temperature of about 39° C. or b) the mutation inhibiting protein synthesis at a non-permissive temperature of about 39° C. with each of the EIV-P821 HA, NP and NS-1 proteins are shown in Tables 3 and 4, respectively.

TABLE 3

Reassortment analysis of the EIV-P821 39° C. plaque formation phenotype with avian influenza virus, A/mallard/New York/6750/78

| Gene | Virus | ts+[1] | ts−[2] |
|---|---|---|---|
| HA | avian | 26 | 13 |
|  | equine | 11 | 44 |
| NP | avian | 37 | 8 |
|  | equine | 0 | 49 |
| NS-1 | avian | 9 | 8 |
|  | equine | 12 | 20 |

[1] number of clonal isolates able to induce CPE in tissue culture cells at a temperature of about 39° C.
[2] number of clonal isolates inhibited in the ability to induce CPE in tissue culture cells at a temperature of about 39° C.

TABLE 4

Reassortment analysis of the EIV-P821 39° C. protein synthesis phenotype with avian influenza virus, A/mallard/New York/6750/78

| Gene | Virus | ts+[1] | ts−[2] |
|---|---|---|---|
| HA | avian | 18 | 1 |
|  | equine | 11 | 7 |
| NP | avian | 34 | 5 |
|  | equine | 7 | 8 |
| NS-1 | avian | 10 | 4 |
|  | equine | 14 | 5 |

[1] number of clonal isolates which synthesize all viral proteins at a temperature of about 39° C.
[2] number of clonal isolates inhibited in the ability to synthesize all viral proteins at a temperature of about 39° C.

The results demonstrated an association of the equine NP gene with a mutation causing the inability of EIV-P821 to form plaques at a non-permissive temperature of about 39° C., but the results did not suggest an association of any of the HA, NP, or NS-1 genes with a mutation causing the inability of EIV-P821 to express viral proteins at a non-permissive temperature of about 39° C. Thus, these data also demonstrated that the plaque formation phenotype and the protein synthesis phenotype observed in virus EIV-P821 were the result of separate mutations.

D. Studies were also conducted to determine if cold-adapted equine influenza viruses of the present invention have a dominant interference phenotype, that is, whether they dominate in mixed infection with the wild type parental virus A/Kentucky/1/91 (H3N8). The dominant interference phenotype of viruses EIV-P821 and EIV-P824 were evaluated in the following manner. Separate monolayers of MDCK cells were singly infected with the parental virus A/Kentucky/1/91 (H3N8) at an MOI of 2, singly infected with either cold-adapted virus EIV-P821 or EIV-P824 at an MOI of 2, or simultaneously doubly infected with both the parental virus and one of the cold adapted viruses at an MOT of 2+2, all at a temperature of about 34° C. At 24 hours after infection, the media from the cultures were harvested and the virus yields from the various infected cells were measured by duplicate plaque assays performed at temperatures of about 34° C. and about 39° C. This assay took advantage of the fact that cold adapted equine influenza viruses EIV-P821 or EIV-P824 are temperature sensitive and are thus unable to form plaques at a non-permissive temperature of about 39° C., while the parental virus is able to form plaques at both temperatures, thus making it possible to measure the growth of the parental virus in the presence of the cold adapted virus. Specifically, the dominant interference effect of the cold adapted virus on the growth of the parental virus was quantitated by comparing the virus yield at about 39° C. of the cells singly infected with parental virus to the yield of the parental virus in doubly infected cells. EIV-P821, in mixed infection, was able to reduce the yield of the parental virus by approximately 200 fold, while EIV-P824, in mixed infection, reduced the yield of the parental virus by approximately 3200 fold. This assay therefore showed that cold-adapted equine influenza viruses EIV-P821 and EIV-P824 both exhibit the dominant interference phenotype.

E. Virus isolate EIV-MSV+5 was derived from EIV-P821, as follows. EIV-P821 was passaged once in eggs, as described above, to produce a Master Seed Virus isolate, denoted herein as EIV-MSV0. EIV-MSV0 was then subjected to passage three additional times in eggs, the virus isolates at the end of each passage being designated EIV-MSV+1, EIV-MSV+2, and EIV-MSV+3, respectively. EIV-MSV+3 was then subjected to two additional passages in MDCK cells, as follows. MDCK cells were grown in 150 cm$^2$ tissue culture flasks in MEM tissue culture medium with Hanks Salts, containing 10% calf serum. The cells were then washed with sterile PBS and the growth medium was replaced with about 8 ml per flask of infection medium (tissue culture medium comprising MEM with Hanks Salts, 1 μg/ml TPCK trypsin solution, 0.125% bovine serum albumin (BSA), and 10 mM HEPES buffer). MDCK cells were inoculated with AF containing virus EIV-MSV+3 (for the first passage in MDCK cells) or virus stock harvested from EIV-MSV+4 (for the second passage in MDCK cells), and the viruses were allowed to adsorb for 1 hour at about 34° C. The inoculum was removed from the cell monolayers, the cells were washed again with PBS, and about 100 ml of infection medium was added per flask. The infected cells were incubated at about 34° C. for 24 hours. The virus-infected MDCK cells were harvested by shaking the flasks vigorously to disrupt the cell monolayer, resulting in virus isolates EIV-MSV+4 (the first passage in MDCK cells), and EIV-MSV+5 (the second passage in MDCK cells).

Viruses EIV-MSV0 and EIV-MSV+5 were subjected to phenotypic analysis, as described in section B above, to determine their ability to form plaques and synthesize viral proteins at temperatures of about 34° C., about 37° C., and about 39° C. Both EIV-MSV0 and EIV-MSV+5 formed plaques in tissue culture cells at a temperature of about 34° C., and neither virus isolate formed plaques or exhibited detectable viral protein synthesis at a temperature of about 39° C. Virus EIV-MSV0 had a similar temperature sensitive phenotype as EIV-P821 at a temperature of about 37° C., i.e., it was inhibited in plaque formation, and late gene expression was inhibited. However, EIV-MSV+5, unlike its parent virus, EIV-P821, did form plaques in tissue culture at a temperature of about 37° C., and at this temperature, the virus synthesized normal amounts of all proteins. Virus EIV-MSV+5 has been deposited with the ATCC under Accession No. ATCC VR-2627.

EXAMPLE 2

Therapeutic compositions of the present invention were produced as follows.

A. A large stock of ETV-P821 was propagated in eggs as follows. About 60 specific pathogen-free embryonated chicken eggs were candled and non-viable eggs were discarded. Stock virus was diluted to about $1.0 \times 10^5$ pfu/ml in sterile PBS. Virus was inoculated into the allantoic cavity of the eggs as described in Example 1A. After a 3-day incubation in a humidified chamber at a temperature of about 34° C., AF was harvested from the eggs according to the method described in Example 1A. The harvested AF was mixed with a stabilizer solution, for example A1/A2 stabilizer, available from Diamond Animal Health, Des Moines, Iowa, at 25% V/V (stabilizer/AF). The harvested AU was batched in a centrifuge tube and was clarified by centrifugation for 10 minutes at 1000 rpm in an IEC Centra-7R refrigerated table top centrifuge fitted with a swinging bucket rotor. The clarified fluid was distributed into 1-ml cryovials and was frozen at about −70° C. Virus stocks were titrated on MDCK cells by CPE and plaque assay at about 34° C.

B. A large stock of EIV-P821 was propagated in MDCK cells as follows. MDCK cells were grown in 150 $cm^2$ tissue culture flasks in MEM tissue culture medium with Hanks Salts, containing 10% calf serum. The cells were then washed with sterile PBS and the growth medium was replaced with about 8 ml per flask of infection medium. The MDCK cells were inoculated with virus stock at an MOI ranging from about 0.5 pfu per cell to about 0.005 pfu per cell, and the viruses were allowed to adsorb for 1 hour at about 34° C. The inoculum was removed from the cell monolayers, the cells were washed again with PBS, and about 100 ml of infection medium was added per flask. The infected cells were incubated at about 34° C. for 24 hours. The virus-infected MDCK cells were harvested by shaking the flasks vigorously to disrupt the cell monolayer and stabilizer solution was added to the flasks at 25% V/V (stabilizer/virus solution). The supernatants were distributed aseptically into cryovials and frozen at −70° C.

C. Therapeutic compositions comprising certain cold-adapted temperature sensitive equine influenza viruses of the present invention were formulated as follows. Just prior to vaccination procedures, such as those described in Examples 3-7 below, stock vials of EIV-P821 or EIV-MSV+5 were thawed and were diluted in an excipient comprising either water, PBS, or in MEM tissue culture medium with Hanks Salts, containing 0.125% bovine serum albumin (BSA-MEM solution) to the desired dilution for administration to animals. The vaccine compositions were held on ice prior to vaccinations. All therapeutic compositions were titered on MDCK cells by standard methods just prior to vaccinations and wherever possible, an amount of the composition, treated identically to those administered to the animals, was titered after the vaccinations to ensure that the virus remained viable during the procedures.

EXAMPLE 3

A therapeutic composition comprising cold-adapted equine influenza virus EIV-P821 was tested for safety and its ability to replicate in three horses showing detectable prior immunity to equine influenza virus as follows. EIV-P821, produced as described in Example 1A, was grown in eggs as described in Example 2A and was formulated into a therapeutic composition comprising $10^7$ pfu EIV-P821/2 ml BSA-MEM solution as described in Example 2C.

Three ponies having prior detectable hemagglutination inhibition (HAI) titers to equine influenza virus were inoculated with a therapeutic composition comprising EIV-P821 by the following method. Each pony was given a 2-ml dose of EIV-P821, administered intranasally using a syringe fitted with a blunt cannula long enough to reach past the false nostril, 1 ml per nostril.

The ponies were observed for approximately 30 minutes immediately following and at approximately four hours after vaccination for immediate type allergic reactions such as sneezing, salivation, labored or irregular breathing, shaking, anaphylaxis, or fever. The animals were further monitored on days 1-11 post-vaccination for delayed type allergic reactions, such as lethargy or anorexia. None of the three ponies in this study exhibited any allergic reactions from the vaccination.

The ponies were observed daily, at approximately the same time each day, starting two days before vaccination and continuing through day 11 following vaccination for clinical signs consistent with equine influenza. The ponies were observed for nasal discharge, ocular discharge, anorexia, disposition, heart rate, capillary refill time, respiratory rate, dyspnea, coughing, lung sounds, presence of toxic line on upper gum, and body temperature. In addition submandibular and parietal lymph nodes were palpated and any abnormalities were described. None of the three ponies in this study exhibited any abnormal reactions or overt clinical signs during the observation period.

To test for viral shedding in the animals, on days 0 through 11 following vaccination, nasopharyngeal swabs were collected from the ponies as described in Chambers, et al., 1995, *Equine Practice,* 17, 19-23. Chambers, et al., ibid. Briefly, two sterile Dacron polyester tipped applicators (available, e.g., from Hardwood Products Co., Guilford, Me.) were inserted, together, into each nostril of the ponies. The swabs (four total, two for each nostril) were broken off into a 15-ml conical centrifuge tube containing 2.5 ml of chilled transport medium comprising 5% glycerol, penicillin, streptomycin, neomycin, and gentamycin in PBS at physiological pH. Keeping the samples on wet ice, the swabs were aseptically wrung out into the medium and the nasopharyngeal samples were divided into two aliquots. One aliquot was used to attempt isolation of EIV by inoculation of embryonated eggs, using the method described in Example 1. The AF of the inoculated eggs was then tested for its ability to cause hemagglutination, by standard methods, indicating the presence of equine influenza virus in the AF. On days 2 and 3 post-vaccination, the other aliquots were tested for virus by the Directigen® Flu A test, available from Becton-Dickinson (Cockeysville, Md.).

Attempts to isolate EIV from the nasopharyngeal secretions of the three animals by egg inoculation were unsuccessful. However on days 2 and 3, all animals tested positive for the presence of virus shedding using the Directigen Flu A test, consistent with the hypothesis that EIV-P821 was replicating in the seropositive ponies.

To test the antibody titers to EIV in the inoculated animals described in this example, as well as in the animals described in Examples 4-7, blood was collected from the animals prior to vaccination and on designated days post-vaccination. Serum was isolated and was treated either with trypsin/periodate or kaolin to block the nonspecific inhibitors of hemagglutination present in normal sera. Serum samples were tested for hemagglutination inhibition (HAI) titers against a recent EIV isolate by standard methods, described, for example in the "Supplemental assay method for conducting the hemagglutination inhibition assay for equine influenza virus antibody" (SAM 124), provided by the U.S.D.A. National Veterinary Services Laboratory under 9 CFR 113.2.

The HAI titers of the three ponies are shown in Table 5. As can be seen, regardless of the initial titer, the serum HAI titers increased at least four-fold in all three animals after vaccination with EIV-P821.

These data demonstrate that cold-adapted equine influenza virus EIV-P821 is safe and non-reactogenic in sero-positive ponies, and that these animals exhibited an increase in antibody titer to equine influenza virus, even though they had prior demonstrable titers.

TABLE 5

HAI titers of vaccinated animals*

| Animal | HAI Titer (days after vaccination) | | | |
|---|---|---|---|---|
| ID | 0 | 7 | 14 | 21 |
| 18 | 40 | 80 | 160 | 160 |
| 19 | 10 | 20 | 40 | 80 |
| 25 | 20 | 40 | 320 | 80 |

*HAI titers are expressed as the reciprocal of the highest dilution of serum which inhibited hemagglutination of erythrocytes by a recent isolate of equine influenza virus.

EXAMPLE 4

This Example discloses an animal study to evaluate the safety and efficacy of a therapeutic composition comprising cold-adapted equine influenza virus EIV-P821.

A therapeutic composition comprising cold-adapted equine influenza virus EIV-P821 was tested for attenuation, as well as its ability to protect horses from challenge with virulent equine influenza virus, as follows. EIV-P821, produced as described in Example 1, was grown in eggs as described in Example 2A and was formulated into a therapeutic composition comprising $10^7$ pfu of virus/2 ml water, as described in Example 2C. Eight EIV-seronegative ponies were used in this study. Three of the eight ponies were vaccinated with a 2-ml dose comprising $10^7$ pfu of the EIV-P821 therapeutic composition, administered intranasally, using methods similar to those described in Example 3. One pony was given $10^7$ pfu of the EIV-P821 therapeutic composition, administered orally, by injecting 6 ml of virus into the pharynx, using a 10-ml syringe which was adapted to create a fine spray by the following method. The protruding "seat" for the attachment of needles was sealed off using modeling clay and its cap was left in place. About 10 holes were punched through the bottom of the syringe, i.e., surrounding the "seat," using a 25-gauge needle. The syringe was placed into the interdental space and the virus was forcefully injected into the back of the mouth. The remaining four ponies were held as non-vaccinated controls.

The vaccinated ponies were observed for approximately 30 minutes immediately following and at approximately four hours after vaccination for immediate type allergic reactions, and the animals were further monitored on days 1-11 post-vaccination for delayed type allergic reactions, both as described in Example 3. None of the four vaccinated ponies in this study exhibited any abnormal reactions from the vaccination.

The ponies were observed daily, at approximately the same time each day, starting two days before virus vaccination and continuing through day 11 following vaccination for clinical signs, such as those described in Example 3. None of the four vaccinated ponies in this study exhibited any clinical signs during the observation period. This result demonstrated that cold-adapted equine influenza virus EIV-P821 exhibits the phenotype of attenuation.

To test for viral shedding in the vaccinated animals, on days 0 through 11 following vaccination, nasopharyngeal swabs were collected from the ponies as described in Example 3. The nasopharyngeal samples were tested for virus in embryonated chicken eggs according to the method described in Example 3.

As shown in Table 6, virus was isolated from only one vaccinated animal using the egg method. However, as noted in Example 3, the lack of isolation by this method does not preclude the fact that virus replication is taking place, since replication may be detected by more sensitive methods, e.g., the Directigen Flu A test.

TABLE 6

Virus isolation in eggs after vaccination.

| Animal | | Virus Isolation (days after vaccination) | | | | | | | | | | |
|---|---|---|---|---|---|---|---|---|---|---|---|---|
| ID | Route | 0 | 1 | 2 | 3 | 4 | 5 | 6 | 7 | 8 | 9 | 10 | 11 |
| 91 | IN | − | − | + | + | + | + | + | + | + | + | + | − |
| 666 | IN | − | − | − | − | − | − | − | − | − | − | − | − |
| 673 | IN | − | − | − | − | − | − | − | − | − | − | − | − |
| 674 | Oral | − | − | − | − | − | − | − | − | − | − | − | − |

To test the antibody titers to equine influenza virus in the vaccinated animals, blood was collected from the animals prior to vaccination and on days 7, 14, 21, and 28 post-vaccination. Serum samples were isolated and were tested for hemagglutination inhibition (HAI) titers against a recent EIV isolate according to the methods described in Example 3.

The HAI titers of the four vaccinated ponies are shown in Table 7.

TABLE 7

HAI titers after vaccination.

| Animal | | HAI Titer (days after vaccination) | | | | |
|---|---|---|---|---|---|---|
| ID | Route | 0 | 7 | 14 | 21 | 28 |
| 91 | IN | <10 | <10 | <10 | <10 | <10 |
| 666 | IN | 10 | 10 | 10 | 20 | 20 |
| 673 | IN | 10 | 10 | 10 | 20 | 20 |
| 674 | Oral | 20 | 40 | 40 | 40 | 40 |

Unlike the increase in HAI titer observed with the three animals described in the study in Example 3, the animals in this study did not exhibit a significant increase, i.e., greater than four-fold, in HAI titer following vaccination with EIV-P821.

Approximately four and one-half months after vaccine virus administration, all 8 ponies, i.e., the four that were vaccinated and the four non-vaccinated controls, were challenged by the following method. For each animal, $10^7$ pfu of the virulent equine influenza virus strain A/equine/Kentucky/1/91 (H3N8) was suspended in 5 ml of water. A mask was connected to a nebulizer, and the mask was placed over the animal's muzzle, including the nostrils. Five (5) ml was nebulized for each animal, using settings such that it took 5-10 minutes to deliver the full 5 ml. Clinical observations, as described in Example 3, were performed on all animals three days before challenge and daily for 11 days after challenge.

Despite the fact that the vaccinated animals did not exhibit marked increases in their HAI titers to equine influenza virus, all four vaccinated animals were protected against equine influenza virus challenge. None of the vaccinated animals showed overt clinical signs or fever, although one of the animals had a minor wheeze for two days. On the other hand, all four non-vaccinated ponies shed virus and developed clinical signs and fever typical of equine influenza virus infection. Thus, this example demonstrates that a therapeutic composition of the present invention can protect horses from equine influenza disease.

EXAMPLE 5

This Example discloses an additional animal study to evaluate attenuation of a therapeutic composition comprising cold-adapted equine influenza virus EIV-P821, and its ability to protect vaccinated horses from subsequent challenge with virulent equine influenza virus. Furthermore, this study evaluated the effect of exercise stress on the safety and efficacy of the therapeutic composition.

A therapeutic composition comprising cold-adapted equine influenza virus EIV-P821 was tested for safety and efficacy in horses, as follows. EIV-P821, produced as described in Example 1, was grown in eggs as described in Example 2A and was formulated into a therapeutic composition comprising $10^7$ pfu virus/5 ml water, as described in Example 2C. Fifteen ponies were used in this study. The ponies were randomly assigned to three groups of Five animals each, as shown in Table 8, there being two vaccinated groups and one unvaccinated control group. The ponies in group 2 were exercise stressed before vaccination, while the ponies in vaccinate group 1 were held in a stall.

TABLE 8

Vaccination/challenge protocol.

| Group | No. Ponies | Exercise | Vaccine | Challenge |
|---|---|---|---|---|
| 1 | 5 | — | Day 0 | Day 90 |
| 2 | 5 | Days −4 to 0 | Day 0 | Day 90 |
| 3 | 5 | — | — | Day 90 |

The ponies in group 2 were subjected to exercise stress on a treadmill prior to vaccination, as follows. The ponies were acclimated to the use of the treadmill by 6 hours of treadmill use at a walk only. The actual exercise stress involved a daily exercise regimen starting 4 days before and ending on the day of vaccination (immediately prior to vaccination). The treadmill exercise regimen is shown in Table 9.

TABLE 9

Exercise regimen for the ponies in Group 2.

| Speed (m/sec) | Time (min.) | Incline (°) |
|---|---|---|
| 1.5 | 2 | 0 |
| 3.5 | 2 | 0 |
| 3.5 | 2 | 7 |
| 4.5 † | 2 | 7 |
| 5.5 † | 2 | 7 |
| 6.5 † | 2 | 7 |
| 7.5 † | 2 | 7 |
| 8.5 † | 2 | 7 |
| 3.5 | 2 | 7 |
| 1.5 | 10 | 0 † |

†Speed, in meters per second (m/sec) was increased for each animal every 2 minutes until the heart rate reached and maintained ≧200 beats per minute Groups 1 and 2 were given a therapeutic composition comprising $10^7$ pfu of EIV-P821, by the nebulization method described for the challenge described in Example 4. None of the vaccinated ponies in this study exhibited any immediate or delayed allergic reactions from the vaccination.

The ponies were observed daily, at approximately the same time each day, starting two days before vaccination and continuing through day 11 following vaccination for clinical signs, such as those described in Example 3. None of the vaccinated ponies in this study exhibited any overt clinical signs during the observation period.

To test for viral shedding in the vaccinated animals, before vaccination and on days 1 through 11 following vaccination, nasopharyngeal swabs were collected from the ponies as described in Example 3. The nasopharyngeal samples were tested for virus in embryonated chicken eggs according to the method described in Example 3. Virus was isolated from the vaccinated animals, i.e., Groups 1 and 2, as shown in Table 10.

TABLE 10

Virus isolation after vaccination.

| Group | Animal ID | Exercise | Virus Isolation (days after vaccination) | | | | | | | | | | | |
|---|---|---|---|---|---|---|---|---|---|---|---|---|---|---|
| | | | 0 | 1 | 2 | 3 | 4 | 5 | 6 | 7 | 8 | 9 | 10 | 11 |
| 1 | 12 | No | − | − | + | + | + | + | + | − | + | + | − | − |
| | 16 | | − | − | + | + | + | + | + | − | − | − | − | − |
| | 17 | | − | − | + | + | + | + | + | + | − | − | + | − |
| | 165 | | − | − | − | − | − | − | − | − | − | − | − | − |
| | 688 | | − | − | − | − | + | − | + | − | − | − | − | − |
| 2 | 7 | Yes | − | − | − | + | + | + | + | − | − | − | − | − |
| | 44 | | − | − | − | − | − | − | − | − | − | − | − | − |
| | 435 | | − | − | + | + | + | + | − | − | − | − | − | − |
| | 907 | | − | − | − | + | − | + | + | − | − | − | − | − |
| | 968 | | − | − | − | − | − | + | − | + | − | − | − | − |

To test the antibody titers to equine influenza virus in the vaccinated animals, blood was collected prior to vaccination and on days 7, 14, 21, and 28 post-vaccination. Serum samples were isolated and were tested for HAI titers against a recent EIV isolate according to the methods described in Example 3. These titers are shown in Table 11.

TABLE 11

HAI titers after vaccination and after challenge on day 90.

| Group | Animal ID | Day Post-vaccination | | | | | | | | | |
|---|---|---|---|---|---|---|---|---|---|---|---|
| | | −1 | 7 | 14 | 21 | 28 | 91 | 105 | 112 | 119 | 126 |
| 1 | 12 | <10 | <10 | <10 | <10 | <10 | <10 | 80 | 320 | 320 | 640 |
| 1 | 16 | <10 | <10 | 20 | 20 | <10 | <10 | 20 | 160 | 320 | 320 |
| 1 | 17 | <10 | <10 | 10 | 10 | 10 | 10 | 80 | 160 | 160 | 160 |
| 1 | 165 | <10 | <10 | 10 | 10 | 10 | 10 | 80 | 80 | 80 | 80 |
| 1 | 688 | <10 | <10 | 20 | 20 | 20 | 20 | 20 | 20 | 20 | 40 |
| 2 | 7 | <10 | <10 | 10 | 10 | <10 | <10 | 20 | 80 | 80 | 40 |
| 2 | 44 | <10 | <10 | 20 | 20 | 20 | 10 | 80 | 320 | 320 | 320 |
| 2 | 435 | <10 | <10 | 20 | 20 | 10 | <10 | 20 | 80 | 80 | 80 |
| 2 | 907 | <10 | <10 | 10 | 10 | 20 | 10 | 10 | 40 | 80 | 80 |
| 2 | 968 | <10 | <10 | <10 | <10 | <10 | <10 | 40 | 160 | 160 | 160 |
| 3 | 2 | | | | | | <10 | 80 | 640 | 640 | 320 |
| 3 | 56 | | | | | | <10 | 80 | 320 | 320 | 320 |
| 3 | 196 | | | | | | <10 | 20 | 160 | 80 | 80 |
| 3 | 198 | | | | | | 10 | 40 | 160 | 320 | 320 |
| 3 | 200 | | | | | | <10 | 20 | 80 | 80 | 40 |

| Group | Description |
|---|---|
| 1 | Vaccination only |
| 2 | Vaccination and Exercise |
| 3 | Control |

On day 90 post vaccination, all 15 ponies were challenged with $10^7$ pfu of equine influenza virus strain A/equine/Kentucky/1/91 (H3N8) by the nebulizer method as described in Example 4. Clinical observations, as described in Example 3, were performed on all animals three days before challenge and daily for 11 days after challenge. There were no overt clinical signs observed in any of the vaccinated ponies. Four of the Five non-vaccinated ponies developed fever and clinical signs typical of equine influenza virus infection.

Thus, this example demonstrates that a therapeutic composition of the present invention protects horses against equine influenza disease, even if the animals are stressed prior to vaccination.

EXAMPLE 6

This Example compared the infectivities of therapeutic compositions of the present invention grown in eggs and grown in tissue culture cells. From a production standpoint, there is an advantage to growing therapeutic compositions of the present invention in tissue culture rather than in embryonated chicken eggs. Equine influenza virus, however, does not grow to as high a titer in cells as in eggs. In addition, the hemagglutinin of the virus requires an extracellular proteolytic cleavage by trypsin-like proteases for infectivity. Since serum contains trypsin inhibitors, virus grown in cell culture must be propagated in serum-free medium that contains trypsin in order to be infectious. It is well known by those skilled in the art that such conditions are less than optimal for the viability of tissue culture cells. In addition, these growth conditions may select for virus with altered binding affinity for equine cells, which may affect viral infectivity since the virus needs to bind efficiently to the animal's nasal mucosa to replicate and to stimulate immunity. Thus, the objective of the study disclosed in this example was to evaluate whether the infectivity of therapeutic compositions of the present invention was adversely affected by growth for multiple passages in vitro tissue culture.

EIV-P821, produced as described in Example 1, was grown in eggs as described in Example 2A or in MDCK cells as described in Example 2B. In each instance, the virus was passaged Five times. EIV-P821 was tested for its cold-adaptation and temperature sensitive phenotypes after each passage. The egg and cell-passaged virus preparations were formulated into therapeutic compositions comprising $10^7$ pfu virus/2 ml BSA-MEM solution, as described in Example 2C, resulting in an egg-grown EIV-P821 therapeutic composition and an MDCK cell-grown EIV-P821 therapeutic composition, respectively.

Eight ponies were used in this study. Serum from each of the animals was tested for HAI titers to equine influenza virus prior to the study. The animals were randomly assigned into one of two groups of four ponies each. Group A received the egg-grown EIV-P821 therapeutic composition, and Group B received the MDCK-grown EIV-P821 therapeutic composition, prepared as described in Example 2B. The therapeutic compositions were administered intranasally by the method described in Example 3.

The ponies were observed daily, at approximately the same time each day, starting two days before vaccination and continuing through day 11 following vaccination for allergic reactions or clinical signs as described in Example 3. No allergic reactions or overt clinical signs were observed in any of the animals.

Nasopharyngeal swabs were collected before vaccination and daily for 11 days after vaccination. The presence of virus material in the nasal swabs was determined by the detection of CPE on MDCK cells infected as described in Example 1, or by inoculation into eggs and examination of the ability of the infected AF to cause hemagglutination, as described in Example 3. The material was tested for the presence of virus only, and not for titer of virus in the sample. Virus isolation results are listed in Table 12. Blood was collected and serum samples from days 0, 7, 14, 21 and 28 after vaccination were tested for hemagglutination inhibition antibody titer against a recent isolate. HAI titers are also listed in Table 12.

TABLE 12

HAI titers and virus isolation after vaccination.

| | | HAI Titer (DPV[3]) | | | | Virus Isolation [1] (DPV[3]) | | | | | | | | | | | |
|---|---|---|---|---|---|---|---|---|---|---|---|---|---|---|---|---|---|
| Group[2] | ID | 0 | 7 | 14 | 21 | 28 | 0 | 1 | 2 | 3 | 4 | 5 | 6 | 7 | 8 | 9 | 10 | 11 |
| 1 | 31 | <10 | 20 | 160 | 160 | 160 | — | EC | — | C | EC | EC | C | C | EC | — | — | — |
|   | 37 | <10 | 40 | 160 | 160 | 160 | — | EC | C | C | EC | C | C | C | — | — | — | — |
|   | 40 | <10 | 20 | 80 | 160 | 80 | — | EC | EC | C | — | C | EC | C | — | EC | EC | — |
|   | 41 | <10 | 40 | 160 | 160 | 80 | — | EC | EC | C | EC | C | EC | EC | — | — | — | — |
| 2 | 32 | <10 | <10 | 80 | 80 | 40 | — | EC | — | C | — | C | — | C | — | EC | — | — |
|   | 34 | <10 | 20 | 160 | 160 | 160 | — | EC | — | C | EC | C | EC | C | — | — | — | — |
|   | 35 | <10 | <10 | 80 | 80 | 40 | — | EC | — | C | — | C | — | C | — | EC | — | — |
|   | 42 | <10 | <10 | 80 | 80 | 40 | — | — | — | C | — | C | EC | EC | — | — | — | — |

[1] E = Egg isolation positive; C = CPE isolation positive; - = virus not detected by either of the methods
[2] Group 1: Virus passaged 5× in MDCK cells; Group 2: Virus passaged 5× in Eggs
[3] Days Post-vaccination The results in Table 12 show that there were no significant differences in infectivity or immunogenicity between the egg-grown and MDCK-grown EIV-P821 therapeutic compositions.

EXAMPLE 7

This example evaluated the minimum dose of a therapeutic composition comprising a cold-adapted equine influenza virus required to protect a horse from equine influenza virus infection.

The animal studies disclosed in Examples 3-6 indicated that a therapeutic composition of the present invention was efficacious and safe. In those studies, a dose of $10^7$ pfu, which correlates to approximately $10^8$ $TCID_{50}$units, was used. However, from the standpoints of cost and safety, it is advantageous to use the minimum virus titer that will protect a horse from disease caused by equine influenza virus. In this study, ponies were vaccinated with four different doses of a therapeutic composition comprising a cold-adapted equine influenza virus to determine the minimum dose which protects a horse against virulent equine influenza virus challenge.

EYV-P821, produced as described in Example 1A, was passaged and grown in MDCK cells as described in Example 2B and was formulated into a therapeutic composition comprising either $2\times10^4$, $2\times10^5$, $2\times10^6$, or $2\times10^7$ $TCID_{50}$, units/1 ml BSA-MEM solution as described in Example 2C. Nineteen horses of various ages and breeds were used for this study. The horses were assigned to four vaccine groups, one group of three horses and three groups of four horses, and one control group of four horses (see Table 13). Each of the ponies in the vaccine groups were given a 1-ml dose of the indicated therapeutic composition, administered intranasally by methods similar to those described in Example 3.

TABLE 13

Vaccination protocol.

| Group No. | No. Animals | Vaccine Dose, $TCID_{50}$ Units |
|---|---|---|
| 1 | 3 | $2\times10^7$ |
| 2 | 4 | $2\times10^6$ |
| 3 | 4 | $2\times10^5$ |
| 4 | 4 | $2\times10^4$ |
| 5 | 4 | control |

The ponies were observed for approximately 30 minutes immediately following and at approximately four hours after vaccination for immediate type reactions, and the animals were further monitored on days 1-11 post-vaccination for delayed type reactions, both as described in Example 3. None of the vaccinated ponies in this study exhibited any abnormal reactions or overt clinical signs from the vaccination.

Blood for serum analysis was collected 3 days before vaccination, on days 7, 14, 21, and 28 after vaccination, and after challenge on Days 35 and 42. Serum samples were tested for HAI titers against a recent EIV isolate according to the methods described in Example 3. These titers are shown in Table 14. Prior to challenge on day 29, 2 of the 3 animals in group 1, 4 of the 4 animals in group 2, 3 of the 4 animals in group 3, and 2 of the 4 animals in group 4 showed at least 4-fold increases in HAI titers after vaccination. In addition, 2 of the 4 control horses also exhibited increases in HAI titers. One interpretation for this result is that the control horses were exposed to vaccine virus transmitted from the vaccinated horses, since all the horses in this study were housed in the same barn.

TABLE 14

HAI titers post-vaccination and post-challenge, and challenge results.

| No. | Dose in TCID$_{50}$ units | Animal ID | Vaccination on Day 0, Challenge on Day 29 |  |  |  |  |  |  | Chall. Sick +/− |
|---|---|---|---|---|---|---|---|---|---|---|
|  |  |  | −1 | 7 | 14 | 21 | 28 | 35 | 42 |  |
| 1 | $2 \times 10^7$ | 41 | <10 | <10 | 10 | 40 | 10 | 20 | 80 | − |
|  |  | 42 | 40 | 40 | 40 | 40 | 40 | <10 | 80 | − |
|  |  | 200 | <10 | <10 | 80 | 40 | 160 | 40 | 40 | − |
| 2 | $2 \times 10^6$ | 679 | <10 | 10 | 40 | 40 | 40 | 20 | 20 | − |
|  |  | 682 | <10 | <10 | 40 | 40 | 40 | 40 | 40 | − |
|  |  | 795 | 20 | 80 | 160 | 160 | 320 | 320 | 640 | − |
|  |  | R | <10 | 10 | 40 | 20 | 160 | 40 | 40 | − |
| 3 | $2 \times 10^5$ | 73 | <10 | <10 | 160 | 40 | 80 | 160 | 160 | − |
|  |  | 712 | <10 | <10 | 20 | 20 | 40 | 40 | 20 | − |
|  |  | 720 | <10 | 20 | 80 | 40 | 80 | 80 | 160 | − |
|  |  | 796 | <10 | <10 | <10 | <10 | <10 | 10 | 80 | + |
| 4 | $2 \times 10^4$ | 75 | <10 | <10 | <10 | <10 | <10 | <10 | 160 | + |
|  |  | 724 | <10 | >10 | <10 | <10 | <10 | 20 | 320 | + |
|  |  | 789 | <10 | 10 | 320 | 160 | 320 | 320 | 320 | − |
|  |  | 790 | <10 | <10 | 80 | 40 | 160 | 80 | 40 | − |
| 5 | Control | 12 | <10 | <10 | <10 | 20 | 20 | 40 | 40 | − |
|  |  | 22 | 10 | 20 | 40 | 10 | 160 | 40 | 640 | − |
|  |  | 71 | <10 | <10 | <10 | <10 | 10 | 20 | 160 | + |
|  |  | 74 | <10 | <10 | <10 | <10 | <10 | <10 | 20 | + |

On day 29 post vaccination, all 19 ponies were challenged with equine influenza virus strain a/equine/Kentucky/1/91 (H3N8) by the nebulizer method as described in Example 4. The challenge dose was prospectively calculated to contain about $10^8$ TCID$_{50}$ units of challenge virus in a volume of 5 ml for each animal. Clinical observations, as described in Example 3, were monitored beginning two days before challenge, the day of challenge, and for 11 days following challenge. As shown in Table 14, no animals in groups 1 or 2 exhibited clinical signs indicative of equine influenza disease, and only one out of four animals in group 3 became sick. Two out of four animals in group 4 became sick, and only two of the four control animals became sick. The results in Table 14 suggest a correlation between seroconversion and protection from disease, since, for example, the two control animals showing increased HAI titers during the vaccination period did not show clinical signs of equine influenza disease following challenge. Another interpretation, however, was that the actual titer of the challenge virus may have been less than the calculated amount of $10^8$ TCID$_{50}$ units, since, based on prior results, this level of challenge should have caused disease in all the control animals.

Nonetheless, the levels of seroconversion and the lack of clinical signs in the groups that received a therapeutic composition comprising at least $2 \times 10^6$ TCID$_{50}$ units of a cold-adapted equine influenza virus suggests that this amount was sufficient to protect a horse against equine influenza disease. Furthermore, a dose of $2 \times 10^5$ TCID$_{50}$ units induced seroconversion and gave clinical protection from challenge in 3 out of 4 horses, and thus even this amount may be sufficient to confer significant protection in horses against equine influenza disease.

EXAMPLE 8

This example discloses an animal study to evaluate the duration of immunity of a therapeutic composition comprising cold-adapted equine influenza virus EIV-P821.

A therapeutic composition comprising cold-adapted equine influenza virus EIV-P821, produced as described in Example 1, was grown in eggs similarly to the procedure described in Example 2A, was expanded by passage in MDCK cells similarly to the procedure described in Example 2B, and was formulated into a therapeutic composition as described in Example 2C. Thirty horses approximately 11 to 12 months of age were used for this study. Nineteen of the horses were each vaccinated intranasally into one nostril using a syringe with a delivery device tip attached to the end, with a 1.0 ml dose comprising 6 logs of TCID$_{50}$ units of the EIV-P821 therapeutic composition. Vaccinations were performed on Day 0.

The horses were observed on Day 0 (before vaccination and up to 4 hours post-vaccination) and on Study Days 1, 2, 3, 7, 15, and 169 post-vaccination. On these days, a distant examination for a period of at least 15 minutes was performed. This distant examination included observation for demeanor, behavior, coughing, sneezing, and nasal discharge. The examination on Day 169 also served to confirm that the horses were in a condition of health suitable for transport to the challenge site which was located approximately 360 miles from the vaccination site.

The animals were acclimated to the challenge site and were observed approximately daily by a veterinarian or animal technician for evidence of disease. A general physical examination was performed on Day 171 post-vaccination to monitor the following: demeanor, behavior, coughing, sneezing, and nasal discharge. From Days 172 to 177, similar observations as well as rectal temperature were recorded, according to the judgment of the attending veterinarian for any individual horse with abnormal clinical presentation.

No vaccinated horses showed any adverse reactions post-vaccination. One vaccinate was found dead about two months after vaccination. This horse showed no evidence of adverse reaction when observed for at least one month after vaccination. Although no cause of death could be firmly established, the death was not instantaneous and was considered to be consistent with possible contributing factors such as colic, bone fracture, or severe worm burden. Since there was no other evidence for any adverse reactions post-vaccination in any other vaccinates, it is highly unlikely that the vaccine contributed to any adverse reaction in this case.

Challenges were performed on Day 181 post-vaccination. The following wild-type isolate of equine influenza virus previously shown to cause disease in horses was used as the challenge virus: A/equine/2/Kentucky/91. Prior to infection of each challenge group, the challenge material was rapidly thawed at approximately 37° C. The virus was diluted with phosphate-buffered saline to a total volume of approximately 21 ml. The diluted material was stored chilled on ice until immediately before inoculation. Before inoculation and at the end of nebulization for each challenge group, a sample of diluted challenge virus was collected for pre-and post-inoculation virus titer confirmation. Vaccinates and controls were randomly assigned to 4 challenge groups of 6 horses each and one challenge group of 5 horses so that each challenge group contained a mixture of 4 vaccinates and 2 controls or 3 vaccinates and 2 controls.

Challenge virus in aerosol form was delivered through a tube inserted through a small opening centrally in the plastic ceiling with an ultrasonic nebulizer (e.g., DeVilbiss Model 099HD, DeVilbiss Healthcare Inc., Somerset, Pa.) for a period of approximately 10 minutes. The horses remained in the chamber for a further period of approximately 30 minutes after the nebulization had been completed (total exposure time, approximately 40 minutes). At that time, the plastic was removed to vent the chamber, and the horses were released and returned to their pen. The challenge procedure was repeated for each group.

All statistical methods in this study were performed using SAS (SAS Institute, Cary, N.C.), and P<0.05 was considered to be statistically significant. Beginning on Day 178 post-vaccination (three days prior to challenge) through Day 191 (day 10 post-challenge), the horses were observed daily by both distant and individual examinations. Rectal temperatures were measured at these times. Data from day 0 (challenge day) to day 10 were included in the analysis; see Table 15.

TABLE 15

Effect of challenge on daily temperatures (° C.) in vaccinated and control horses (least squares means).

| Day post challenge | Vaccinated (n = 19) | non-vaccinated (n = 10) | P-value |
|---|---|---|---|
| 0 | 100.7 | 100.8 | 0.8434 |
| 1 | 100.5 | 100.4 | 0.7934 |
| 2 | 103.4 | 104.9 | 0.0024 |
| 3 | 101.8 | 103.9 | 0.0001 |
| 4 | 101.5 | 103.2 | 0.0002 |
| 5 | 101.7 | 103.8 | 0.0001 |
| 6 | 101.3 | 103.6 | 0.0001 |
| 7 | 100.7 | 102.3 | 0.0007 |
| 8 | 100.5 | 101.4 | 0.0379 |
| 9 | 100.1 | 100.3 | 0.7416 |
| 10 | 100.3 | 100.5 | 0.7416 |
| pooled SEM* | 0.27 | 0.38 | |

*Standard error of the mean

Table 15 shows that on days 2 through 8, vaccinated horses had lower temperatures (P<0.05) than the non-vaccinated control horses.

The distant examination consisted of a period of 20 minutes where the following observations were made: coughing, nasal discharge, respiration, and depression. Scoring criteria are shown in Table 16.

TABLE 16

Clinical signs and scoring index.

| Clinical Sign | Description | Score |
|---|---|---|
| Coughing | normal during observation period of 15 min | 0 |
| | coughing once during observation | 1 |
| | coughing twice or more during observation | 2 |
| Nasal discharge | normal | 0 |
| | abnormal, serous | 1 |
| | abnormal, mucopurulent | 2 |
| | abnormal, profuse | 3 |
| Respiration | normal | 0 |
| | abnormal (dyspnea, tachypnea) | 1 |
| Depression | normal | 0 |
| | depression present† | 1 |

†Depression was assessed by subjective evaluation of individual animal behavior that included the following: failure to approach food rapidly, general lethargy, inappetence, and anorexia.

Each horse was scored for each of these categories. Additionally, submandibular lymph nodes were palpated to monitor for possible bacterial infection. In any case where there was a different value recorded for a subjective clinical sign score from an observation on the same day at the distant versus the individual examination, the greater score was used in the compilation and analysis of results. For purposes of assessing the health of the horses prior to final disposition, distant examinations were performed at 14, 18, and 21 days post-challenge. Data from days 1 through 10 post-challenge were included in the analysis. These scores were summed on each day for each horse, and the vaccinates and controls were compared using the Wilcoxon rank sums test. In addition, these scores were summed across all days for each horse, and compared in the same manner. The mean ranks and mean clinical scores are shown in Tables 17 and 18, respectively. Five days post-challenge, the mean rank of scores in the vaccinated horses was lower (P<0.05) than in the non-vaccinated control horses; and this effect continued on days 6, 7, 8, 9, and 10 (P<0.05). The cumulative rank over the entire test period was also lower (P<0.05) in the vaccinated horses than the non-vaccinated controls.

TABLE 17

Effect of challenge on clinical sign scores in vaccinated and control horses (mean rank).

| Day post challenge | Vaccinated (n = 19), mean rank* | Non-vaccinated (n = 10), mean rank | P-value |
|---|---|---|---|
| 0 | 13.6 | 17.6 | 0.1853 |
| 1 | 16.4 | 12.4 | 0.2015 |
| 2 | 15.1 | 14.9 | 0.9812 |
| 3 | 13.3 | 18.3 | 0.1331 |
| 4 | 13.5 | 17.9 | 0.1721 |
| 5 | 12.4 | 19.9 | 0.0237 |
| 6 | 12.7 | 19.4 | 0.0425 |
| 7 | 12.1 | 20.6 | 0.0074 |
| 8 | 12.6 | 19.6 | 0.0312 |
| 9 | 13.1 | 18.7 | 0.0729 |
| 10 | 12.3 | 20.1 | 0.0135 |
| total over 11 days | 11.8 | 21.2 | 0.0051 |

*By Wilcoxon rank sum test.

TABLE 18

Effect of challenge on clinical sign scores in
vaccinated and control horses (mean scores).

| Day post challenge | Vaccinated (n = 19) | Non-vaccinated (n = 10) |
|---|---|---|
| 0 | 1.2 | 1.6 |
| 1 | 1.5 | 0.9 |
| 2 | 2.4 | 2.5 |
| 3 | 3.2 | 4.1 |
| 4 | 3.4 | 4.3 |
| 5 | 3.2 | 4.7 |
| 6 | 3.4 | 4.8 |
| 7 | 3.3 | 4.7 |
| 8 | 3.2 | 4.5 |
| 9 | 3.2 | 3.9 |
| 10 | 2.4 | 3.4 |

Nasopharyngeal swabs were obtained on the day prior to challenge and on days 1 to 8 post-challenge, as described in Example 3, and tested for shed virus by cell culture assay. The percent of horses shedding challenge virus in each group is shown in Table 19. The percent of horses shedding the challenge virus in the vaccinated group was lower (P<0.05) on days 5 and 6 post-challenge than in the non-vaccinated controls. The mean number of days the challenge virus was shed was also lower (P<0.05) in the vaccinated group as compared to the non-vaccinated controls.

TABLE 19

Percent of horses shedding virus per day post-challenge
and mean number of days of shedding per group.

| Day post challenge | Vaccinated (n = 19) | Non-vaccinated (n = 10) |
|---|---|---|
| −1 | 0 | 0 |
| 1 | 63.2 | 90 |
| 2 | 100 | 100 |
| 3 | 84.2 | 100 |
| 4 | 100 | 100 |
| 5 | 47.4 | 88.9* |
| 6 | 10.5 | 77.8* |
| 7 | 5.3 | 20 |
| 8 | 0 | 0 |
| average number of days shedding | 4.1 | 5.6* |

*Within a time point, vaccinates different from non-vaccinates (P < 0.05) by either Fisher's exact test (percent data) or Wilcoxon rank sums test (days shedding).

The scores from clinical signs relevant to influenza and the objective temperature measurements both demonstrated a statistically significant reduction in the group of vaccinates when compared to those from the control group; this is consistent with an interpretation that the vaccine conferred significant protection from disease.

The ability of horses to shed influenza virus post-challenge was also significantly reduced in vaccinates as compared to controls in both the incidence of horses positive for shedding on certain days post-challenge and the mean number of days of shedding per horse. This decreased shedding by vaccinates is important in that it should serve to reduce the potential for exposure of susceptible animals to the wild-type virus in an outbreak of influenza.

The results of this study are consistent with the interpretation that the vaccine safely conferred protection for 6 months from clinical disease caused by equine influenza and reduced the potential for the spread of naturally occurring virulent equine influenza virus. While the degree of protection from disease was not complete (13 out of 19 vaccinates were pro-tected, while 10/10 controls were sick), there was a clear reduction in the severity and duration of clinical illness and a noticeable effect on the potential for viral shedding after exposure to a virulent strain of equine influenza. The finding that both vaccinates and controls were seronegative immediately prior to challenge at 6 months post-immunization suggests that immunity mediated by something other than serum antibody may be of primary importance in the ability of this vaccine to confer measurable and durable protection.

EXAMPLE 9

This Example discloses an animal study to evaluate the ability of a therapeutic composition comprising cold-adapted equine influenza virus EIV-P821 to aid in the prevention of disease following exposure to a heterologous strain of equine influenza virus.

The heterologous strain tested was A/equine/2/Saskatoon/90, described genetically as a Eurasian strain (obtained from Hugh Townsend, University of Saskatchewan). Twenty female Percheron horses approximately 15 months of age (at the time of vaccination) were used for the efficacy study. The horses were assigned to two groups, one group of 10 to be vaccinated and another group of 10 to serve as non-vaccinated controls. On day 0, the vaccinate group was vaccinated in the manner described in Example 8.

The challenge material, i.e. equine flu strain A/equine/2/Saskatoon/90 [H3N8] was prepared similarly to the preparation in Example 8. Vaccinates and controls were randomly assigned to 4 challenge groups of 5 horses each such that each challenge group contained a mixture of 2 vaccinates and three controls or vice versa. The challenge procedure was similar to that described in Example 8. Challenges were performed on Day 28 post-vaccination.

Clinical observations were performed for the vaccinates and controls on Day −4 and on Study Days 0 (before vaccination and up to 4 hours post-vaccination), 1 to 7, 12, 15 to 17, 19 to 23, 25 to 38, and 42. For days on which clinical observations were performed during Days −4 to 42, clinical observations including rectal temperature were recorded according to the judgment of the attending veterinarian for any individual horse with abnormal clinical presentation. Horses were scored using the same criteria as in Example 8 (Table 15). Distant examinations were performed on these days as described in Example 8. On Day 20 and from Days 25 to 38, the horses were also observed by both distant and individual examinations (also performed as described in Example 8).

Rectal temperatures were measured daily beginning 3 days prior to challenge, and continuing until 10 days post-challenge. Day 0 is the day relative to challenge. Data from days 0 through 10 were included in the analysis. Statistical methods and criteria were identical to those used in Example 8. On days 2, 5 and 7, vaccinated horses had statistically significant lower body temperatures than the non-vaccinated control horses (Table 20).

TABLE 20

Effect of challenge on daily temperatures (° C.) in
vaccinated and control horses (least squares means).

| Day post challenge | Vaccinated (n = 10) | Non-vaccinated (n = 10) | P-value |
|---|---|---|---|
| 0 | 99.9 | 99.8 | 0.9098 |
| 1 | 100.5 | 100.3 | 0.4282 |
| 2 | 101.0 | 102.8 | 0.0001 |
| 3 | 100.7 | 100.6 | 0.7554 |

TABLE 20-continued

Effect of challenge on daily temperatures (° C.) in vaccinated and control horses (least squares means).

| Day post challenge | Vaccinated (n = 10) | Non-vaccinated (n = 10) | P-value |
|---|---|---|---|
| 4 | 101.0 | 101.3 | 0.4119 |
| 5 | 100.8 | 102.1 | 0.0004 |
| 6 | 100.4 | 100.4 | 0.9774 |
| 7 | 100.3 | 101.1 | 0.0325 |
| 8 | 100.6 | 100.7 | 0.8651 |
| 9 | 100.5 | 100.6 | 0.8874 |
| 10 | 100.5 | 100.1 | 0.2465 |

Standard error of the mean = 0.249.

Data from days 1 through 10 post-challenge were included in the analysis. These scores were summed on each day for each horse, and the vaccinates and controls were compared using the Wilcoxon rank sums test. All statistical methods were performed as described in Example 9. In addition, these scores were summed across all days for each horse, and compared in the same manner. Mean ranks are shown in Table 21.

TABLE 21

Effect of challenge on clinical sign scores in vaccinated and control horses (mean rank).

| Day post challenge | Vaccinated (n = 10) | Non-vaccinated (n = 10) | P-value* |
|---|---|---|---|
| 1 | 8.85 | 12.15 | 0.1741 |
| 2 | 8.80 | 12.20 | 0.1932 |
| 3 | 8.90 | 12.10 | 0.2027 |
| 4 | 7.60 | 13.40 | 0.0225 |
| 5 | 6.90 | 14.10 | 0.0053 |
| 6 | 7.00 | 14.00 | 0.0059 |
| 7 | 6.90 | 14.10 | 0.0053 |
| 8 | 7.60 | 13.40 | 0.0251 |
| 9 | 6.90 | 14.10 | 0.0048 |
| 10 | 6.10 | 14.90 | 0.0006 |
| total over 10 days | 5.70 | 15.30 | 0.0003 |

*By Wilcoxon 2 sample test.

On day 4 post-challenge, the mean rank of scores in the vaccinated horses was lower (P<0.05) than the non-vaccinated control horses, and this effect continued throughout the remainder of the study (P<0.05). The cumulative rank over the entire test period was also lower in the vaccinated horses than the non-vaccinated controls (P<0.05).

Nasopharyngeal swabs were collected on days 1 and 8 post-challenge, as described in Example 3. The nasal samples were analyzed for the presence of virus by cell inoculation with virus detection by cytopathogenic effect (CPE) or by egg inoculation with virus detection by hemagglutination (HA). The cell-culture assay was performed as generally described by Youngner et al., 1994, *J. Clin. Microbiol.* 32, 750-754. Serially diluted nasal samples were added to wells containing monolayers of Madin Darby Canine Kidney (MDCK) cells. After incubation, wells were examined for the presence and degree of cytopathogenic effect. The quantity of virus in $TCID_{50}$ units was calculated by the Reed-Muench technique. The egg infectivity assay was performed as described in Example 1. The percent of horses shedding challenge virus for each assay in each group is shown in Tables 22 and 23. The percent of horses shedding the challenge virus in the vaccinated group was lower (P<0.05) on days 2 through 7 post-challenge by either method. No differences were seen on days 1 or 8 post-challenge. The number of days the challenge virus was shed was also lower (P<0.05) in the vaccinated group as compared to the non-vaccinated controls; see Tables 22 and 23.

TABLE 22

Percent of horses shedding virus following challenge - cell culture assay.

| Day post challenge | Vaccinated (n = 10) | Non-vaccinated (n = 10) |
|---|---|---|
| 1 | 0 | 0 |
| 2 | 0 | 70* |
| 3 | 0 | 70* |
| 4 | 20 | 100* |
| 5 | 10 | 100* |
| 6 | 20 | 100* |
| 7 | 0 | 80* |
| 8 | 0 | 30 |
| average number of days shedding | 0.5 | 5.5* |

*Within a time point, vaccinates different from non-vaccinates, P < 0.05 by either Fisher's exact test (percent data) or Wilcoxon 2 sample test (days shedding)

TABLE 23

Percent of horses shedding virus following challenge - egg infectivity assay.

| Day post challenge | Vaccinated (n = 10) | Non-vaccinated (n = 10) |
|---|---|---|
| 1 | 0 | 0 |
| 2 | 0 | 70* |
| 3 | 10 | 70* |
| 4 | 0 | 90* |
| 5 | 10 | 70* |
| 6 | 20 | 90* |
| 7 | 0 | 50* |
| 8 | 0 | 0 |
| average number of days shedding | 0.4 | 4.4* |

*Within a time point, vaccinates different from non-vaccinates, P < 0.05 by either Fisher's exact test (percent data) or Wilcoxon 2 sample test (days shedding).

The extent (severity and duration) of clinical signs of influenza among vaccinates was substantially reduced relative to the controls. The scores from clinical signs relevant to influenza and the objective temperature measurements both demonstrated a statistically significant reduction in the group of vaccinates when compared to those from the control group; indicating that the vaccine conferred significant protection from disease by the heterologous strain.

The ability of horses to shed influenza virus post-challenge was also significantly reduced in vaccinates as opposed to controls in both the incidence of horses positive for shedding on certain days post-challenge and the mean number of days of shedding per horse. This decreased shedding by vaccinates is important in that it should serve to reduce the potential for exposure of susceptible animals to the wild-type virus in an outbreak of influenza.

Overall, the results of this study show that the vaccine conferred protection against a heterologous challenge by a member of the Eurasian lineage of equine influenza virus strains.

EXAMPLE 10

This Example discloses an animal study to evaluate the ability of a therapeutic composition comprising cold-adapted equine influenza virus EIV-P821 to aid in the prevention of disease following exposure to a heterologous strain of equine influenza virus.

The heterologous strain tested was A/equine/2/Kentucky/98 [H3N8](obtained from Tom Chambers, University of Kentucky). Eight ponies aged 5 to 7 months were used for this efficacy study. The horses were assigned to two groups, one group of 4 to be vaccinated and another group of 4 to serve as non-vaccinated controls. Ponies were vaccinated as described in Example 8, on Day 0.

Clinical observations were performed for the vaccinates on Study Day 0 (before vaccination and at 4 hours post-vaccination), as well as on Days 1 to 8, 23, 30 to 50, and 57 post-vaccination. Controls were observed clinically on Days 29 to 50 and 57. The observations were performed and scored as described in Example 8.

The challenge material i.e. equine flu strain from Kentucky/98, was prepared by passing the isolated virus two times in eggs. The inoculum for each horse was prepared by thawing 0.5 ml of the virus, then diluting in 4.5 ml of sterile phosphate-buffered saline. The inoculum was administered by nebulization using a mask for each individual horse on Day 36 post-vaccination.

The clinical observation scores were summed on each day for each horse, and horses were ranked according to the cumulative total score from days 1 to 9 post-challenge. Theses results are shown in Table 24.

TABLE 24

Clinical sign observations: total scores, ranked by total score.

| Group | Halter Identity | Total Score[#] Days 1 to 9 post-challenge |
|---|---|---|
| 1-Vaccinate | 50 | 0 |
| 1-Vaccinate | 52 | 0 |
| 1-Vaccinate | 55 | 1 |
| 1-Vaccinate | 15 | 2 |
| 2-Control | 61 | 21 |
| 2-Control | 20 | 25 |
| 2-Control | 7 | 26 |
| 2-Control | 13 | 26 |

[#]Total scores represent the sum of daily scores (where daily scores equal the sum of scores for coughing, nasal discharge, respiration, and depression) and are ranked from the lowest (least severe) to highest (most severe) scores.

The results of Table 24 show that the scores for vaccinates were between 0 and 2, which was significantly lower than the score for controls, which were between 21 and 26.

Rectal temperatures were measured daily beginning 6 days prior to challenge, and continuing until 9 days post-challenge. Day 0 is the day relative to challenge. Data from days 0 through 9 were included in the analysis. These results are shown in Table 25.

TABLE 25

Effect of Challenge on daily mean temperatures (° C.) in vaccinated and control horses.

| Day post challenge | control | vaccinate | difference |
|---|---|---|---|
| 0 | 99.7 | 99.5 | 0.2 |
| 1 | 100.0 | 99.6 | 0.4 |
| 2 | 103.9 | 100.2 | 3.7 |
| 3 | 99.8 | 99.2 | 0.6 |
| 4 | 99.6 | 99.1 | 0.5 |
| 5 | 99.8 | 99.3 | 0.5 |
| 6 | 99.6 | 99.3 | 0.3 |
| 7 | 99.3 | 99.0 | 0.3 |
| 8 | 99.7 | 99.6 | 0.1 |
| 9 | 99.5 | 99.1 | 0.4 |

The temperatures of the control horses were higher than the temperatures of the vaccinated horses on all days. The temperature in control horses was significantly higher on day 2.

Nasopharyngeal swabs were collected on days 1 and 8, post-challenge, as described in Example 3. These samples were tested for shed virus by an egg infectivity assay as described in Example 1. The results of the assay are shown in Table 26.

TABLE 26

Virus shedding post-challenge detected by egg infectivity.

| | | Study day | | | | | | | | | |
|---|---|---|---|---|---|---|---|---|---|---|---|
| | | 35 | 37 | 38 | 39 | 40 | 41 | 42 | 43 | 44 | |
| | | Days post-challenge | | | | | | | | | |
| Group | Identity No. | −1 | 1 | 2 | 3 | 4 | 5 | 6 | 7 | 8 | No. days positive per horse |
| | | Detection of virus* | | | | | | | | | |
| Vaccinates | 15 | 0 | 2 | 0 | 3 | 3 | 0 | 2 | 1 | 0 | 5 |
| | 50 | 0 | 0 | 0 | 0 | 0 | 1 | 0 | 0 | 0 | 1 |
| | 52 | 0 | 0 | 3 | 3 | 2 | 2 | 0 | 0 | 0 | 4 |
| | 55 | 0 | 2 | 3 | 1 | 3 | 0 | 0 | 0 | 0 | 4 |
| No. horses positive per day | | 0 | 2 | 2 | 3 | 3 | 2 | 1 | 1 | 0 | |
| Controls | 07 | 0 | 3 | 3 | 3 | 3 | 3 | 3 | 1 | 0 | 7 |
| | 13 | 0 | 3 | 3 | 3 | 3 | 3 | 3 | 1 | 0 | 7 |
| | 20 | 0 | 2 | 3 | 3 | 3 | 3 | 3 | 1 | 0 | 7 |

TABLE 26-continued

Virus shedding post-challenge detected by egg infectivity.

|  |  | Study day | | | | | | | | |
|---|---|---|---|---|---|---|---|---|---|---|
|  |  | 35 | 37 | 38 | 39 | 40 | 41 | 42 | 43 | 44 |
|  |  | | | Days post-challenge | | | | | | |
| Group | Identity No. | −1 | 1 | 2 | 3 | 4 | 5 | 6 | 7 | 8 | No. days positive per horse |
|  |  | | | Detection of virus* | | | | | | |
|  | 61 | 0 | 3 | 3 | 3 | 3 | 3 | 3 | 2 | 0 | 7 |
| No. horses positive per day | | 0 | 4 | 4 | 4 | 4 | 4 | 4 | 4 | 0 | |

*Values refer to the number of eggs testing positive of 3 eggs tested per sample. For statistical analysis, a sample was considered positive for virus if at least 1 egg was positive per sample.

The results of Table 26 show that the number of horses positive per day was higher for the controls than for the vaccinates. Additionally, control horses were positive for more days than vaccinates.

The scores from clinical signs relevant to influenza and the objective temperature measurements both demonstrated significant differences in the group of vaccinates when compared to the control group; this shows that the vaccine conferred significant protection from disease caused by the heterologous strain Kentucky/98.

The ability of horses to shed influenza virus post-challenge was also significantly reduced in vaccinated as opposed to controls in the mean number of days of shedding per horse. This decreased shedding by vaccinates is important in that it should serve to reduce the potential for exposure of susceptible animals to the wild-type virus in an outbreak of influenza.

Overall, the results of this study show that the vaccine safely conferred protection to a heterologous challenge by a recent and clinically relevant isolate. When the results of this study are viewed in the light of the protection previously demonstrated against heterologous challenge with a Eurasian strain (Example 9), there is clear evidence to support the assertion that this modified live vaccine can confer protection against heterologous as well as homologous equine influenza infection.

EXAMPLE 11

This example describes the cloning and sequencing of equine influenza M (matrix) protein nucleic acid molecules for wild type and cold-adapted equine influenza viruses.

A. Nucleic acid molecules encoding wild type or cold-adapted equine influenza virus M protein, were produced as follows. A PCR product containing an equine M gene was produced by PCR amplification from equine influenza virus DNA, and primers w584 and w585, designated SEQ ID NO:26, and SEQ ID NO:27, respectively. A nucleic acid molecule of 1023 nucleotides, denoted $nei_{wt}M_{1023}$, with a coding strand having a nucleic acid sequence designated SEQ ID NO:1 was produced by further PCR amplification using the above described PCR product as a template and cloned into pCR 2.1®TA cloning vector, available from Invitrogen, Carlsbad, Calif., using standard procedures recommended by the manufacturer. The primers used were the T7 primer, designated by SEQ ID NO:29 and the REV primer, designated by SEQ ID NO:28. Plasmid DNA was purified using a mini-prep method available from Qiagen, Valencia, Calif. PCR products were prepared for sequencing using a PRISM™ Dye Terminator Cycle Sequencing Ready Reaction kit, a PRISM™ drhodamine Terminator Cycle Sequencing Ready Reaction kit, or a PRISM™ BigDye™ Terminator Cycle Sequencing Ready Reaction kit, all available from PE Applied Biosystems, Foster City, Calif., following the manufacturer's protocol. Specific PCR conditions used with the kit were a rapid ramp to 95° C., hold for 10 seconds followed by a rapid ramp to 50° C. with a 5 second hold then a rapid ramp to 60° C. with a 4 minute hold, repeating for 25 cycles. Different sets of primers were used in different reactions: T7 and REV were used in one reaction; w584 and w585 were used in a second reaction; and efM-a1, designated SEQ ID NO:31 and efM-s1, designated SEQ ID NO:30 were used in a third reaction. PCR products were purified by ethanol/magnesium chloride precipitation. Automated sequencing of DNA samples was performed using an ABI PRISM™ Model 377 with XL upgrade DNA Sequencer, available from PE Applied Biosystems.

Translation of SEQ ID NO:1 indicates that nucleic acid molecule $nei_{wt}M_{1023}$ encodes a full-length equine influenza M protein of about 252 amino acids, referred to herein as $Pei_{wt}M_{252}$, having amino acid sequence SEQ ID NO:2, assuming an open reading frame in which the initiation codon spans from nucleotide 25 through nucleotide 28 of SEQ ID NO:1 and the termination codon spans from nucleotide 781 through nucleotide 783 of SEQ ID NO:1. The region encoding $Pei_{wt}M_{252}$, designated $nei_{wt}M_{756}$, and having a coding strand comprising nucleotides 25 to 780 of SEQ ID NO:1, is represented by SEQ ID NO:3.

SEQ ID NO:1 and SEQ ID NO:3 represent the consensus sequence obtained from two wild type nucleic acid molecules, which differ in one nucleotide. Nucleotide 663 of $nei_{wt1}M_{1023}$, i.e., nucleotide 649 of $nei_{wt1}M_{756}$, was adenine, while nucleotide 663 of $nei_{wt2}M_{1023}$, i.e., nucleotide 649 of $nei_{wt2}M_{756}$, was guanine. Translation of these sequences does not result in an amino acid change at the corresponding amino acid; both translate to valine at residue 221 in $Pei_{wt}M_{252}$, B. A nucleic acid molecule of 1023 nucleotides encoding a cold-adapted equine influenza virus M, denoted $nei_{ca1}M_{1023}$, with a coding strand having a sequence designated SEQ ID NO:4 was produced by further PCR amplification and cloned into the pCR®-Blunt cloning vector available from Invitrogen, using conditions recommended by the manufacturer, and primers T7 and REV. Plasmid DNA purification and cycle sequencing were performed as described in Example 11, part A. Translation of SEQ ID NO:4 indicates that nucleic acid molecule $nei_{ca1}M_{1023}$ encodes a full-length equine influenza M protein of about 252 amino acids, referred to herein as $Pei_{ca1}M_{252}$, having amino acid sequence SEQ ID NO:5, assuming an open reading frame in which the initiation codon spans from nucleotide 25 through nucleotide 28 of SEQ ID NO:4 and the termination codon spans from nucleotide 781 through nucleotide 783 of SEQ ID NO:4. The region encoding Pei$_{ca1}$M$_{252}$, designated nei$_{ca1}$M$_{756}$, and having a coding strand comprising nucleotides 25 to 780 of SEQ ID NO:4, is represented by SEQ ID NO:6. PCR amplification of a second nucleic acid molecule encoding a cold-adapted equine influenza M protein in the same manner resulted in molecules $nei_{ca2}M_{1023}$, identical to $nei_{ca1}M_{1023}$, and $nei_{ca2}M_{756}$, identical to $nei_{ca1}M_{756}$.

C. Comparison of the nucleic acid sequences of the coding strands of $nei_{wt}M_{1023}$ (SEQ ID NO:1) and $nei_{ca1}M_{1023}$ (SEQ ID NO:4) by DNA alignment reveals the following differences: a G to T shift at base 67, a C to T shift at base 527, and a C to C shift at base 886. Comparison of the amino acid sequences of proteins $Pei_{wt}M_{252}$ (SEQ ID NO:2) and $Pei_{ca1}M_{252}$ (SEQ ID NO:5) reveals the following differences: a V to L shift at amino acid 23 relating to the G to T shift at base 67 in the DNA sequences; and a T to I shift at amino acid 187 relating to the C to T shift at base 527 in the DNA sequences.

EXAMPLE 12

This example describes the cloning and sequencing of equine influenza HA (hemagglutinin) protein nucleic acid molecules for wild type or cold-adapted equine influenza viruses.

A. Nucleic acid molecules encoding wild type or cold-adapted equine influenza virus HA proteins were produced as follows. A PCR product containing an equine HA gene was produced by PCR amplification from equine influenza virus DNA and primers w578 and w579, designated SEQ ID NO:32 and SEQ ID NO:33, respectively. A nucleic acid molecule of 1762 nucleotides encoding a wild-type HA protein, denoted $nei_{wt}HA_{1762}$, with a coding strand having a nucleic acid sequence designated SEQ ID NO:7 was produced by further PCR amplification using the above-described PCR product as a template and cloned into pCR 2.1®TA cloning vector as described in Example 11A. Plasmid DNA was purified and sequenced as in Example 11A, except that primers used in the sequencing kits were either T7 and REV in one case, or HA-1, designated SEQ ID NO:34, and HA-2, designated SEQ ID NO:35, in a second case.

Translation of SEQ ID NO:7 indicates that nucleic acid molecule $nei_{wt}HA_{1762}$ encodes a full-length equine influenza HA protein of about 565 amino acids, referred to herein as $Pei_{wt}HA_{565}$, having amino acid sequence SEQ ID NO:8, assuming an open reading frame in which the initiation codon spans from nucleotide 30 through nucleotide 33 of SEQ ID NO:7 and the termination codon spans from nucleotide 1725 through nucleotide 1727 of SEQ ID NO:7. The region encoding $Pei_{wt}HA_{565}$, designated $nei_{wt}HA_{1695}$, and having a coding strand comprising nucleotides 30 to 1724 of SEQ ID NO:7 is represented by SEQ ID NO:9.

B. A nucleic acid molecule of 1762 nucleotides encoding a cold-adapted equine influenza virus HA protein, denoted $nei_{ca1}HA_{1762}$, with a coding strand having a sequence designated SEQ ID NO:10 was produced as described in Example 1113. Plasmid DNA purification and cycle sequencing were performed as described in Example 12, part A.

Translation of SEQ ID NO:10 indicates that nucleic acid molecule $nei_{ca1}HA_{1762}$ encodes a full-length equine influenza HA protein of about 565 amino acids, referred to herein as $Pei_{ca1}HA_{565}$, having amino acid sequence SEQ ID NO:11, assuming an open reading frame in which the initiation codon spans from nucleotide 30 through nucleotide 33 of SEQ ID NO:10 and the termination codon spans from nucleotide 1725 through nucleotide 1727 of SEQ ID NO:10. The region encoding $Pei_{ca1}HA_{565}$, designated $nei_{ca1}HA_{1695}$, and having a coding strand comprising nucleotides 30 to 1724 of SEQ ID NO:10, is represented by SEQ ID NO:12.

PCR amplification of a second nucleic acid molecule encoding a cold-adapted equine influenza HA protein in the same manner resulted in molecules $nei_{ca2}HA_{1762}$, identical to $nei_{ca1}HA_{1762}$, and $neica_2HA_{1695}$, identical to $nei_{ca1}HA_{1695}$.

C. Comparison of the nucleic acid sequences of the coding strands of $nei_{wt}HA_{1762}$ (SEQ ID NO:7) and $nei_{ca1}HA_{1762}$ (SEQ ID NO:10) by DNA alignment reveals the following differences: a C to T shift at base 55, a G to A shift at base 499, a G to A shift at base 671, a C to T shift at base 738, a T to C shift at base 805, a G to A shift at base 1289, and an A to G shift at base 1368. Comparison of the amino acid sequences of proteins $Pei_{ca1}HA_{565}$ (SEQ ID NO:8) and $Pei_{ca1}HA_{565}$ (SEQ ID NO:11) reveals the following differences: a P to L shift at amino acid 18 relating to the C to T shift at base 55 in the DNA sequences; a G to E shift at amino acid 166 relating to the & to A shift at base 499 in the DNA sequences; an R to W shift at amino acid 246 relating to the C to T shift at base 738 in the DNA sequences; an M to T shift at amino acid 268 relating to the T to C shift at base 805 in the DNA sequences; a K to E shift at amino acid 456 relating to the A to G shift at base 1368 in the DNA sequences. There is no change of the serine (S) at residue 223 relating to the G to A shift at base 671 in the DNA sequences, nor is there a change of the arginine (R) at residue 429 relating to the G to A shift at base 1289 in the DNA sequences.

EXAMPLE 13

This example describes the cloning and sequencing of equine influenza PB2 protein (RNA-directed RNA polymerase) nucleic acid molecules corresponding to the N-terminal portion of the protein, for wild type or cold-adapted equine influenza viruses.

A. Nucleic acid molecules encoding wild type or cold-adapted equine influenza virus PB2-N proteins were produced as follows. A PCR product containing an N-terminal portion of the equine PB2 gene was produced by PCR amplification from equine influenza virus DNA, and primers w570 and w571, designated SEQ ID NO:36 and SEQ ID NO:37, respectively. A nucleic acid molecule of 1241 nucleotides encoding a wild type PB2-N protein, denoted $nei_{et}PB2\text{-}N_{1241}$, with a coding strand having a nucleic acid sequence designated SEQ ID NO:13 was produced by further PCR amplification using the above described PCR product as a template and cloned as described in Example 11B. Plasmid DNA was purified and sequenced as in Example 11B, except that only T7 and REV primers were used in the sequencing kits.

Translation of SEQ ID NO:13 indicates that nucleic acid molecule $nei_{wt}PB2\text{-}N_{1241}$ encodes an N-terminal portion of influenza PB2 protein of about 404 amino acids, referred to herein as $P_{wt}PB2\text{-}N_{404}$, having amino acid sequence SEQ ID NO:14, assuming an open reading frame in which the initiation codon spans from nucleotide 28 through nucleotide 30 of SEQ ID NO:13, and the last codon spans from nucleotide 1237 through nucleotide 1239. The region encoding $P_{wt}PB2\text{-}N_{404}$, designated $nei_{wt}PB2\text{-}N_{1214}$, and having a coding strand comprising nucleotides 28 to 1239 of SEQ ID NO:13 is represented by SEQ ID NO:15.

B. A nucleic acid molecule of 1239 nucleotides encoding an N-terminal portion of influenza PB2 cold-adapted equine influenza virus PB2-N protein, denoted $nei_{ca1}PB2\text{-}N_{1241}$, with a coding strand having a sequence designated SEQ ID NO:16 was produced, and sequenced as described in as in Example 12, part A.

Translation of SEQ ID NO:16 indicates that nucleic acid molecule nei$_{ca1}$PB2-N$_{1241}$ encodes an N-terminal portion of equine influenza PB-2 protein of about 404 amino acids, referred to herein as P$_{ca1}$PB2-N$_{404}$, having amino acid sequence SEQ ID NO:17, assuming an open reading frame in which the initiation codon spans from nucleotide 28 through nucleotide 30 of SEQ ID NO:16, and the last codon spans from nucleotide 1237 through nucleotide 1239. The region encoding P$_{ca1}$PB2-N$_{404}$, designated nei$_{ca1}$PB2-N$_{1214}$, and having a coding strand comprising nucleotides 28 to 1239 of SEQ ID NO:16, is represented by SEQ ID NO:18.

PCR amplification of a second nucleic acid molecule encoding a cold-adapted equine influenza PB2-N protein in the same manner resulted in molecules nei$_{ca2}$PB2-N$_{1241}$, identical to nei$_{ca1}$PB2-N$_{1241}$, and nei$_{ca2}$PB2-N$_{1214}$, identical to nei$_{ca1}$PB2-N$_{1214}$.

C. Comparison of the nucleic acid sequences of the coding strands of nei$_{wt}$PB2-N$_{1241}$ (SEQ ID NO:13) and nei$_{ca1}$PB2-N$_{1241}$ (SEQ ID NO:16) by DNA alignment reveals the following difference: a T to C base shift at base 370. Comparison of the amino acid sequences of proteins P$_{wt}$PB2-N$_{404}$ (SEQ ID NO:14) and P$_{ca1}$PB2-N$_{404}$ (SEQ ID NO:17) reveals the following difference: a Y to H shift at amino acid 124 relating to the a T to C shift at base 370 in the DNA sequence.

EXAMPLE 14

This example describes the cloning and sequencing of equine influenza PB2 protein (RNA-directed RNA polymerase) nucleic acid molecules corresponding to the C-terminal portion of the protein, for wild type or cold-adapted equine influenza viruses.

A. Nucleic acid molecules encoding wild type or cold-adapted equine influenza virus PB2-C proteins were produced as follows. A PCR product containing the C-terminal portion of the equine PB2 gene was produced by PCR amplification using from equine influenza virus DNA and primers w572 and w573, designated SEQ ID NO:38 and SEQ ID NO:39, respectively. A nucleic acid molecule of 1233 nucleotides encoding a wild type PB2-C protein, denoted nei$_{wt}$PB2-C$_{1233}$, with a coding strand having a nucleic acid sequence designated SEQ ID NO: 19 was produced by further PCR amplification using the above-described PCR product as a template and cloned as described in Example 11B. Plasmid DNA was purified and sequenced as in Example 11A, except that different primers were used in the sequencing kits. T7 and REV were used in one instance; efPB2-a1, designated SEQ ID NO:40 and efPB2-s1, designated SEQ ID NO:41 were used in another instance, and efPB2-a2, designated SEQ ID NO:42 and efPB2-s2, designated SEQ ID NO:43 were used in another instance.

Translation of SEQ ID NO:19 indicates that nucleic acid molecule nei$_{wt1}$PB2-C$_{1233}$ encodes a C-terminal portion of influenza PB2 protein of about 398 amino acids, referred to herein as P$_{wt}$PB2-C$_{398}$, having amino acid sequence SEQ ID NO:20, assuming an open reading frame having a first codon spans from nucleotide 3 through nucleotide 5 and a termination codon which spans from nucleotide 1197 through nucleotide 1199 of SEQ ID NO:19. Because SEQ ID NO:19 is only a partial gene sequence, it does not contain an initiation codon. The region encoding P$_{wt}$PB2-C$_{398}$, designated nei$_{wt}$PB2-C$_{1194}$, and having a coding strand comprising nucleotides 3 to 1196 of SEQ ID NO:19 is represented by SEQ ID NO:21.

PCR amplification of a second nucleic acid molecule encoding a wild type equine influenza PB2-N protein in the same manner resulted in a nucleic acid molecule of 1232 nucleotides denoted nei$_{wt2}$PB2-N$_{1232}$, with a coding strand with a sequence designated SEQ ID NO:22. nei$_{wt2}$PB2-N$_{1232}$ is identical to nei$_{wt1}$PB2-C$_{1233}$, expect that nei$_{wt2}$PB2-N$_{1232}$ lacks one nucleotide on the 5'-end. Translation of SEQ ID NO:22 indicates that nucleic acid molecule nei$_{wt1}$PB2-C$_{1233}$ also encodes P$_{wt}$PB2-C$_{398}$(SEQ ID NO:20), assuming an open reading frame having a first codon which spans from nucleotide 2 through nucleotide 4 and a termination codon spans from nucleotide 1196 through nucleotide 1198 of SEQ ID NO:22. Because SEQ ID NO:22 is only a partial gene sequence, it does not contain an initiation codon. The nucleic acid molecule having a coding strand comprising nucleotides 2 to 1195 of SEQ ID NO:22, denoted nei$_{wt2}$PB2-C$_{1194}$, is identical to SEQ ID NO:21.

B. A nucleic acid molecule of 1232 nucleotides encoding a C-terminal portion of influenza PB2 cold-adapted equine influenza virus protein, denoted nei$_{ca1}$PB2-C$_{1232}$, and having a coding strand having a sequence designated SEQ ID NO:23 was produced as described in as in Example 14, part A, except that the pCR®-Blunt cloning vector was used.

Translation of SEQ ID NO:23 indicates that nucleic acid molecule nei$_{ca1}$PB2-C$_{1232}$ encodes a C-terminal portion of equine influenza PB-2 protein of about 398 amino acids, referred to herein as P$_{ca1}$PB2-C$_{398}$, having amino acid sequence SEQ ID NO:24, assuming an open reading frame having a first codon which spans from nucleotide 2 through nucleotide 4 and a termination codon spans from nucleotide 1196 through nucleotide 1198 of SEQ ID NO:23. Because SEQ ID NO:23 is only a partial gene sequence, it does not contain an initiation codon. The region encoding P$_{ca1}$PB2-C$_{398}$, designated nei$_{ca1}$PB2-C1194, and having a coding strand comprising nucleotides 2 to 1195 of SEQ ID NO:23, is represented by SEQ ID NO:25.

PCR amplification of a second nucleic acid molecule encoding a cold-adapted equine influenza PB2-C protein in the same manner resulted in molecules nei$_{ca2}$PB2-C$_{1231}$, containing one less nucleotide at the 3' end than nei$_{ca1}$PB2-N$_{1241}$; and nei$_{ca2}$PB2-N$_{1214}$, identical to nei$_{ca1}$PB2-N$_{1214}$, C. Comparison of the nucleic acid sequences of the coding strands of nei$_{wt1}$PB2-C$_{1233}$ (SEQ ID NO:19) and nei$_{wt1}$ PB2-C$_{1232}$ (SEQ ID NO:23) by DNA alignment reveals the following differences: an A to C base shift at base 153 of SEQ ID NO:19, and a G to A base shift at base 929 of SEQ ID NO:19. Comparison of the amino acid sequences of proteins P$_{wt}$PB2-C$_{398}$ (SEQ ID NO:20) and P$_{ca1}$PB2-$_{398}$ (SEQ ID NO:24) reveals the following difference: a K to Q shift at amino acid 51 when relating to the an A to C base shift at base 153 in the DNA sequences. There is no amino acid shift resulting from the G to A base shift at base 929.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein comprising an amino acid sequence selected from the group consisting of:
   (a) an amino acid sequence identical to SEQ ID NO:2, with the exception that the amino acid at position 23 of said amino acid sequence is a leucine residue;
   (b) an amino acid sequence identical to SEQ ID NO:2, with the exception that the amino acid at position 187 of said amino acid sequence is an isoleucine residue; and
   (c) an amino acid sequence identical to SEQ ID NO:2, with the exception that the amino acid at position 23 of said amino acid sequence is a leucine residue and the amino acid at position 187 of said amino acid sequence is an isoleucine residue.

2. The isolated protein of claim 1, wherein said amino acid sequence is encoded by a nucleic acid sequence selected from the group consisting of:
   (a) a nucleic acid sequence identical to SEQ ID NO:3, with the exception that the nucleotide at position 43 of said nucleic acid sequence is a thymidine;
   (b) a nucleic acid sequence identical to SEQ ID NO:3, with the exception that the nucleotide at position 503 of said nucleic acid sequence is a thymidine; and
   (c) a nucleic acid sequence identical to SEQ ID NO:3, with the exception that the nucleotide at position 43 of said nucleic acid sequence is a thymidine, and the nucleotide at position 503 of said nucleic acid sequence is a thymidine.

3. The isolated protein of claim 1, wherein said amino acid sequence is encoded by SEQ ID NO:6.

4. The isolated protein of claim 1, wherein said amino acid sequence consists of SEQ ID NO:5.

5. An isolated protein consisting an amino acid sequence selected from the group consisting of:
   (a) an amino acid sequence identical to SEQ ID NO:2, with the exception that the amino acid at position 23 of said amino acid sequence is a leucine residue;
   (b) an amino acid sequence identical to SEQ ID NO:2, with the exception that the amino acid at position 187 of said amino acid sequence is an isoleucine residue; and
   (c) an amino acid sequence identical to SEQ ID NO:2, with the exception that the amino acid at position 23 of said amino acid sequence is a leucine residue and the amino acid at position 187 of said amino acid sequence is an isoleucine residue.

6. The isolated protein of claim 1, wherein said amino acid sequence is encoded by a nucleic acid sequence selected from the group consisting of:
   (a) a nucleic acid sequence identical to SEQ ID NO:3, with the exception that the nucleotide at position 43 of said nucleic acid sequence is a thymidine;
   (b) a nucleic acid sequence identical to SEQ ID NO:3, with the exception that the nucleotide at position 503 of said nucleic acid sequence is a thymidine; and
   (c) a nucleic acid sequence identical to SEQ ID NO:3, with the exception that the nucleotide at position 43 of said nucleic acid sequence is a thymidine, and the nucleotide at position 503 of said nucleic acid sequence is a thymidine.

7. The isolated protein of claim 1, wherein said amino acid sequence is encoded by SEQ ID NO:6.

8. An isolated protein consisting of SEQ ID NO:5.

* * * * *

SEQUENCE LISTING

<160> NUMBER OF SEQ ID NOS: 43

<210> SEQ ID NO 1
<211> LENGTH: 1023
<212> TYPE: DNA
<213> ORGANISM: Equine influenza virus H3N8
<220> FEATURE:
<221> NAME/KEY: CDS
<222> LOCATION: (25)..(780)
<223> OTHER INFORMATION:
<220> FEATURE:
<221> NAME/KEY: misc_feature
<222>

-continued

```
                220                 225                 230
ctt gaa aat ttg cag gcc tac cag aaa cgg atg gga gtg caa atg cag      771
Leu Glu Asn Leu Gln Ala Tyr Gln Lys Arg Met Gly Val Gln Met Gln
    235                 240                 245 cga ttc aag tgatcctctc gttattgcag caagtatcat tgggatcttg              820
Arg Phe Lys
250 cacttgatat tgtggattct tgatcgcctt tcttcaaat tcatttatcg tcgccttaaa     880 tacgggttga aagagggcc ttctacggaa ggagtacctg agtctatgag gaagaatat      940 cggcaggaac agcagaatgc tgtggatgtt gacgatggtc attttgtcaa catagagctg    1000 gagtaaaaaa ctaccttgtt tct                                            1023
```

<210> SEQ ID NO 2
<211> LENGTH: 252
<212> TYPE: PRT
<213> ORGANISM: Equine influenza virus H3N8
<220> FEATURE:
<221> NAME/KEY: misc_feature
<222> LOCATION: (213)..(213)
<223> OTHER INFORMATION: The 'Xaa' at location 213 stands for Val.

<400> SEQUENCE: 2

```
Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
                20                  25                  30

Ala Gly Lys Asn Thr Asp Leu Glu Ala Leu Met Glu Trp Leu Lys Thr
            35                  40                  45

Arg Pro Ile Leu Ser Pro Leu Thr Lys Gly Ile Leu Gly Phe Val Phe
        50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Lys
        195                 200                 205

Ala Arg Gln Met Xaa Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 3
<211> LENGTH: 756
<212> TYPE: DNA
<213> ORGANISM: Equine influenza virus H3N8

<400> SEQUENCE: 3

```
atgagtcttc tgaccgaggt cgaaacgtac gttctctcta tcgtaccatc aggccccctc    60
aaagccgaga tcgcgcagag acttgaagat gtctttgcag ggaagaacac cgatcttgag   120
gcactcatgg aatggctaaa gacaagacca atcctgtcac ctctgactaa agggatttta   180
ggattcgtat tcacgctcac cgtgcccagt gagcgaggac tgcagcgtag acgctttgtc   240
caaaatgccc ttagtggaaa cggagatcca acaacatgg acagagcagt aaaactgtac   300
aggaagctta aagagaaat aacattccat ggggcaaaag aggtggcact cagctattcc    360
actggtgcac tagccagctg catgggactc atatacaaca gaatgggaac tgtgacaacc   420
gaagtggcat ttggcctggt atgcgccaca tgtgaacaga tcgctgattc ccagcatcga   480
tctcacaggc agatggtgac aacaaccaac ccattaatca gacatgaaaa agaatggta   540
ttagccagta ccacggctaa agccatggag cagatggcag ggtcgagtga gcaggcagca   600
gaggccatgg aggttgctag taaggctagg cagatggtrc aggcaatgag aaccattggg   660
acccacccta gctccagtgc cggttttgaaa gatgatctcc ttgaaaattt gcaggcctac   720
cagaaacgga tgggagtgca aatgcagcga ttcaag                             756
```

<210> SEQ ID NO 4
<211> LENGTH: 1023
<212> TYPE: DNA
<213> ORGANISM: Equine influenza virus H3N8
<220> FEATURE:
<221> NAME/KEY: CDS
<222> LOCATION: (25)..(780)
<223> OTHER INFORMATION:

<400> SEQUENCE: 4

```
gcaaaagcag gtagatattt aaag atg agt ctt ctg acc gag gtc gaa acg         51
                             Met Ser Leu Leu Thr Glu Val Glu Thr
                             1               5 tac gtt ctc tct atc tta cca tca ggc ccc ctc aaa gcc gag atc gcg        99
Tyr Val Leu Ser Ile Leu Pro Ser Gly Pro Leu Lys Ala Glu Ile Ala
 10                  15                  20                  25 cag aga ctt gaa gat gtc ttt gca ggg aag aac acc gat ctt gag gca       147
Gln Arg Leu Glu Asp Val Phe Ala Gly Lys Asn Thr Asp Leu Glu Ala
                 30                  35                  40 ctc atg gaa tgg cta aag aca aga cca atc ctg tca cct ctg act aaa       195
Leu Met Glu Trp Leu Lys Thr Arg Pro Ile Leu Ser Pro Leu Thr Lys
             45                  50                  55 ggg att tta gga ttc gta ttc acg ctc acc gtg ccc agt gag cga gga       243
Gly Ile Leu Gly Phe Val Phe Thr Leu Thr Val Pro Ser Glu Arg Gly
         60                  65                  70 ctg cag cgt aga cgc ttt gtc caa aat gcc ctt agt gga aac gga gat       291
Leu Gln Arg Arg Arg Phe Val Gln Asn Ala Leu Ser Gly Asn Gly Asp
 75                  80                  85 cca aac aac atg gac aga gca gta aaa ctg tac agg aag ctt aaa aga       339
Pro Asn Asn Met Asp Arg Ala Val Lys Leu Tyr Arg Lys Leu Lys Arg
 90                  95                 100                 105 gaa ata aca ttc cat ggg gca aaa gag gtg gca ctc agc tat tcc act       387
Glu Ile Thr Phe His Gly Ala Lys Glu Val Ala Leu Ser Tyr Ser Thr
                110                 115                 120 ggt gca cta gcc agc tgc atg gga ctc ata tac aac aga atg gga act       435
Gly Ala Leu Ala Ser Cys Met Gly Leu Ile Tyr Asn Arg Met Gly Thr
```

-continued

```
gtg aca acc gaa gtg gca ttt ggc ctg gta tgc gcc aca tgt gaa cag     483
Val Thr Thr Glu Val Ala Phe Gly Leu Val Cys Ala Thr Cys Glu Gln
        140                 145                 150 atc gct gat tcc cag cat cga tct cac agg cag atg gtg aca ata acc     531
Ile Ala Asp Ser Gln His Arg Ser His Arg Gln Met Val Thr Ile Thr
    155                 160                 165 aac cca tta atc aga cat gaa aac aga atg gta tta gcc agt acc acg     579
Asn Pro Leu Ile Arg His Glu Asn Arg Met Val Leu Ala Ser Thr Thr
170                 175                 180                 185 gct aaa gcc atg gag cag atg gca ggg tcg agt gag cag gca gca gag     627
Ala Lys Ala Met Glu Gln Met Ala Gly Ser Ser Glu Gln Ala Ala Glu
            190                 195                 200 gcc atg gag gtt gct agt aag gct agg cag atg gta cag gca atg aga     675
Ala Met Glu Val Ala Ser Lys Ala Arg Gln Met Val Gln Ala Met Arg
        205                 210                 215 acc att ggg acc cac cct agc tcc agt gcc ggt ttg aaa gat gat ctc     723
Thr Ile Gly Thr His Pro Ser Ser Ser Ala Gly Leu Lys Asp Asp Leu
    220                 225                 230 ctt gaa aat ttg cag gcc tac cag aaa cgg atg gga gtg caa atg cag     771
Leu Glu Asn Leu Gln Ala Tyr Gln Lys Arg Met Gly Val Gln Met Gln
235                 240                 245 cga ttc aag tgatcctctc gttattgcag caagtatcat tgggatcttg             820
Arg Phe Lys
250 cacttgatat tgtggattct tgatcgcctt ttcttcaaat tcatttatcg tcgccttaaa   880 tacggcttga aaagagggcc ttctacggaa ggagtacctg agtctatgag ggaagaatat   940 cggcaggaac agcagaatgc tgtggatgtt gacgatggtc attttgtcaa catagagctg   1000 gagtaaaaaa ctaccttgtt tct                                          1023

<210> SEQ ID NO 5
<211> LENGTH: 252
<212> TYPE: PRT
<213> ORGANISM: Equine influenza virus H3N8

<400> SEQUENCE: 5

Met Ser Leu Leu Thr Glu Val Glu Thr Tyr Val Leu Ser Ile Leu Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160
```

```
Ser His Arg Gln Met Val Thr Ile Thr Asn Pro Leu Ile Arg His Glu
            165                 170                 175

Asn Arg Met Val Leu Ala Ser Thr Thr Ala Lys Ala Met Glu Gln Met
        180                 185                 190

Ala Gly Ser Ser Glu Gln Ala Ala Glu Ala Met Glu Val Ala Ser Lys
    195                 200                 205

Ala Arg Gln Met Val Gln Ala Met Arg Thr Ile Gly Thr His Pro Ser
210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
            245                 250

<210> SEQ ID NO 6
<211> LENGTH: 756
<212> TYPE: DNA
<213> ORGANISM: Equine influenza virus H3N8

<400> SEQUENCE: 6
atgagtcttc tgaccgaggt cgaaacgtac gttctctcta tcttaccatc aggccccctc        60
aaagccgaga tcgcgcagag acttgaagat gtctttgcag ggaagaacac cgatcttgag       120
gcactcatgg aatggctaaa gacaagacca atcctgtcac ctctgactaa agggatttta       180
ggattcgtat tcacgctcac cgtgcccagt gagcgaggac tgcagcgtag acgctttgtc       240
caaaatgccc ttagtggaaa cggagatcca acaacatgg acagagcagt aaaactgtac       300
aggaagctta aaagagaaat aacattccat ggggcaaaag aggtggcact cagctattcc       360
actggtgcac tagccagctg catgggactc atatacaaca gaatgggaac tgtgacaacc       420
gaagtggcat ttggcctggt atgcgccaca tgtgaacaga tcgctgattc ccagcatcga       480
tctcacaggc agatggtgac aataaccaac ccattaatca gacatgaaaa cagaatggta       540
ttagccagta ccacggctaa agccatggag cagatggcag ggtcgagtga gcaggcagca       600
gaggccatgg aggttgctag taaggctagg cagatggtac aggcaatgag aaccattggg       660
acccacccta gctccagtgc cggtttgaaa gatgatctcc ttgaaaattt gcaggcctac       720
cagaaacgga tgggagtgca aatgcagcga ttcaag                                756

<210> SEQ ID NO 7
<211> LENGTH: 1762
<212> TYPE: DNA
<213> ORGANISM: Equine influenza virus H3N8
<220> FEATURE:
<221> NAME/KEY: CDS
<222> LOCATION: (30)..(1724)
<223> OTHER INFORMATION:

<400> SEQUENCE: 7
agcaaaagca ggggatattt ctgtcaatc atg aag aca acc att att ttg ata         53
                                Met Lys Thr Thr Ile Ile Leu Ile
                                  1               5 cca ctg acc cat tgg gtc tac agt caa aac cca acc agt ggc aac aac        101
Pro Leu Thr His Trp Val Tyr Ser Gln Asn Pro Thr Ser Gly Asn Asn
         10                  15                  20 aca gcc aca tta tgt ctg gga cac cat gca gta gca aat gga aca ttg        149
Thr Ala Thr Leu Cys Leu Gly His His Ala Val Ala Asn Gly Thr Leu
 25                  30                  35                  40 gta aaa aca ata act gat gac caa att gag gtg aca aat gct act gaa        197
Val Lys Thr Ile Thr Asp Asp Gln Ile Glu Val Thr Asn Ala Thr Glu
                 45                  50                  55
```

```
tta gtt cag agc att tca ata ggg aaa ata tgc aac aac tca tat aga      245
Leu Val Gln Ser Ile Ser Ile Gly Lys Ile Cys Asn Asn Ser Tyr Arg
            60                  65                  70 gtt cta gat gga aga aat tgc aca tta ata gat gca atg cta gga gac      293
Val Leu Asp Gly Arg Asn Cys Thr Leu Ile Asp Ala Met Leu Gly Asp
        75                  80                  85 ccc cac tgt gat gtc ttt cag tat gag aat tgg gac ctc ttc ata gaa      341
Pro His Cys Asp Val Phe Gln Tyr Glu Asn Trp Asp Leu Phe Ile Glu
    90                  95                 100 aga agc agc gct ttc agc agt tgc tac cca tat gac atc cct gac tat      389
Arg Ser Ser Ala Phe Ser Ser Cys Tyr Pro Tyr Asp Ile Pro Asp Tyr
105                 110                 115                 120 gca tcg ctc cgg tcc att gta gca tcc tca gga aca ttg gaa ttc aca      437
Ala Ser Leu Arg Ser Ile Val Ala Ser Ser Gly Thr Leu Glu Phe Thr
                125                 130                 135 gca gag gga ttc aca tgg aca ggt gtc act caa aac gga aga agt gga      485
Ala Glu Gly Phe Thr Trp Thr Gly Val Thr Gln Asn Gly Arg Ser Gly
            140                 145                 150 tcc tgc aaa agg gga tca gcc gat agt ttc ttt agc cga ctg aat tgg      533
Ser Cys Lys Arg Gly Ser Ala Asp Ser Phe Phe Ser Arg Leu Asn Trp
        155                 160                 165 cta aca gaa tct gga aac tct tac ccc aca ttg aat gtg aca atg cct      581
Leu Thr Glu Ser Gly Asn Ser Tyr Pro Thr Leu Asn Val Thr Met Pro
    170                 175                 180 aac aat aaa aat ttc gac aaa cta tac atc tgg ggg att cat cac ccg      629
Asn Asn Lys Asn Phe Asp Lys Leu Tyr Ile Trp Gly Ile His His Pro
185                 190                 195                 200 agc tca aac aaa gag cag aca aaa ttg tac atc caa gaa tcg gga cga      677
Ser Ser Asn Lys Glu Gln Thr Lys Leu Tyr Ile Gln Glu Ser Gly Arg
                205                 210                 215 gta aca gtc tca aca aaa aga agt caa caa aca ata atc cct aac atc      725
Val Thr Val Ser Thr Lys Arg Ser Gln Gln Thr Ile Ile Pro Asn Ile
            220                 225                 230 gga tct aga ccg cgg gtc agg ggt caa tca ggc agg ata agc ata tac      773
Gly Ser Arg Pro Arg Val Arg Gly Gln Ser Gly Arg Ile Ser Ile Tyr
        235                 240                 245 tgg acc att gta aaa cct gga gat atc cta atg ata aac agt aat ggc      821
Trp Thr Ile Val Lys Pro Gly Asp Ile Leu Met Ile Asn Ser Asn Gly
    250                 255                 260 aac tta gtt gca ccg cgg gga tat ttt aaa ttg aaa aca ggg aaa agc      869
Asn Leu Val Ala Pro Arg Gly Tyr Phe Lys Leu Lys Thr Gly Lys Ser
265                 270                 275                 280 tct gta atg aga tca gat gca ccc ata gac att tgt gtg tct gaa tgt      917
Ser Val Met Arg Ser Asp Ala Pro Ile Asp Ile Cys Val Ser Glu Cys
                285                 290                 295 att aca cca aat gga agc atc ccc aac gac aaa cca ttt caa aat gtg      965
Ile Thr Pro Asn Gly Ser Ile Pro Asn Asp Lys Pro Phe Gln Asn Val
            300                 305                 310 aac aaa gtt aca tat gga aaa tgc ccc aag tat atc agg caa aac act     1013
Asn Lys Val Thr Tyr Gly Lys Cys Pro Lys Tyr Ile Arg Gln Asn Thr
        315                 320                 325 tta aag ctg gcc act ggg atg agg aat gta cca gaa aag caa atc aga     1061
Leu Lys Leu Ala Thr Gly Met Arg Asn Val Pro Glu Lys Gln Ile Arg
    330                 335                 340 gga atc ttt gga gca ata gcg gga ttc ata gaa aac ggc tgg gaa gga     1109
Gly Ile Phe Gly Ala Ile Ala Gly Phe Ile Glu Asn Gly Trp Glu Gly
345                 350                 355                 360 atg gtt gat ggg tgg tat gga ttc cga tat caa aac tcg gaa gga aca     1157
Met Val Asp Gly Trp Tyr Gly Phe Arg Tyr Gln Asn Ser Glu Gly Thr
```

```
                          365                 370                 375
gga caa gct gca gat cta aag agc act caa gca gcc atc gac cag atc      1205
Gly Gln Ala Ala Asp Leu Lys Ser Thr Gln Ala Ala Ile Asp Gln Ile
            380                 385                 390 aat gga aaa tta aac aga gtg att gaa agg acc aat gag aaa ttc cat      1253
Asn Gly Lys Leu Asn Arg Val Ile Glu Arg Thr Asn Glu Lys Phe His
        395                 400                 405 caa ata gag aag gaa ttc tca gaa gta gaa ggg agg atc cag gac ttg      1301
Gln Ile Glu Lys Glu Phe Ser Glu Val Glu Gly Arg Ile Gln Asp Leu
    410                 415                 420 gag aag tat gta gaa gac acc aaa ata gac cta tgg tcc tac aat gca      1349
Glu Lys Tyr Val Glu Asp Thr Lys Ile Asp Leu Trp Ser Tyr Asn Ala
425                 430                 435                 440 gaa ttg ctg gtg gct cta aaa aat caa cat aca att gac tta aca gat      1397
Glu Leu Leu Val Ala Leu Lys Asn Gln His Thr Ile Asp Leu Thr Asp
                445                 450                 455 gca gaa atg aat aaa tta ttc gag aag act aga cgc cag tta aga gaa      1445
Ala Glu Met Asn Lys Leu Phe Glu Lys Thr Arg Arg Gln Leu Arg Glu
            460                 465                 470 aac gcg gaa gac atg gga ggt gga tgt ttc aag ata tac cac aaa tgt      1493
Asn Ala Glu Asp Met Gly Gly Gly Cys Phe Lys Ile Tyr His Lys Cys
        475                 480                 485 gat aat gca tgc att gga tca ata aga aat ggg aca tat gac cat tac      1541
Asp Asn Ala Cys Ile Gly Ser Ile Arg Asn Gly Thr Tyr Asp His Tyr
    490                 495                 500 ata tac aga gat gaa gca tta aac aac cgg ttt caa atc aaa ggt gtt      1589
Ile Tyr Arg Asp Glu Ala Leu Asn Asn Arg Phe Gln Ile Lys Gly Val
505                 510                 515                 520 gag ttg aaa tca ggc tac aaa gat tgg ata ctg tgg att tca ttc gcc      1637
Glu Leu Lys Ser Gly Tyr Lys Asp Trp Ile Leu Trp Ile Ser Phe Ala
                525                 530                 535 ata tca tgc ttc tta att tgc gtt gtt cta ttg ggt ttc att atg tgg      1685
Ile Ser Cys Phe Leu Ile Cys Val Val Leu Leu Gly Phe Ile Met Trp
            540                 545                 550 gct tgc caa aaa ggc aac atc aga tgc aac att tgc att tgagtaaact      1734
Ala Cys Gln Lys Gly Asn Ile Arg Cys Asn Ile Cys Ile
        555                 560                 565 gatagttaaa aacacccttg tttctact                                       1762

<210> SEQ ID NO 8
<211> LENGTH: 565
<212> TYPE: PRT
<213> ORGANISM: Equine influenza virus H3N8

<400> SEQUENCE: 8

Met Lys Thr Thr Ile Ile Leu Ile Pro Leu Thr His Trp Val Tyr Ser
1               5                   10                  15

Gln Asn Pro Thr Ser Gly Asn Asn Thr Ala Thr Leu Cys Leu Gly His
            20                  25                  30

His Ala Val Ala Asn Gly Thr Leu Val Lys Thr Ile Thr Asp Asp Gln
        35                  40                  45

Ile Glu Val Thr Asn Ala Thr Glu Leu Val Gln Ser Ile Ser Ile Gly
    50                  55                  60

Lys Ile Cys Asn Asn Ser Tyr Arg Val Leu Asp Gly Arg Asn Cys Thr
65                  70                  75                  80

Leu Ile Asp Ala Met Leu Gly Asp Pro His Cys Asp Val Phe Gln Tyr
                85                  90                  95

Glu Asn Trp Asp Leu Phe Ile Glu Arg Ser Ser Ala Phe Ser Ser Cys
```

-continued

|   | | | | | 100 | | | | | 105 | | | | | 110 | |
|---|---|---|---|---|---|---|---|---|---|---|---|---|---|---|---|---|

Tyr Pro Tyr Asp Ile Pro Asp Tyr Ala Ser Leu Arg Ser Ile Val Ala
           115                        120                       125

Ser Ser Gly Thr Leu Glu Phe Thr Ala Glu Gly Phe Thr Trp Thr Gly
130                            135                        140

Val Thr Gln Asn Gly Arg Ser Gly Ser Cys Lys Arg Gly Ser Ala Asp
145                      150                  155                      160

Ser Phe Phe Ser Arg Leu Asn Trp Leu Thr Glu Ser Gly Asn Ser Tyr
               165                   170                    175

Pro Thr Leu Asn Val Thr Met Pro Asn Lys Asn Phe Asp Lys Leu
            180                  185                  190

Tyr Ile Trp Gly Ile His His Pro Ser Ser Asn Lys Glu Gln Thr Lys
            195                  200                  205

Leu Tyr Ile Gln Glu Ser Gly Arg Val Thr Val Ser Thr Lys Arg Ser
210                          215                  220

Gln Gln Thr Ile Ile Pro Asn Ile Gly Ser Arg Pro Arg Val Arg Gly
225                      230                  235                  240

Gln Ser Gly Arg Ile Ser Ile Tyr Trp Thr Ile Val Lys Pro Gly Asp
               245                   250                    255

Ile Leu Met Ile Asn Ser Asn Gly Asn Leu Val Ala Pro Arg Gly Tyr
            260                  265                  270

Phe Lys Leu Lys Thr Gly Lys Ser Ser Val Met Arg Ser Asp Ala Pro
           275                  280                  285

Ile Asp Ile Cys Val Ser Glu Cys Ile Thr Pro Asn Gly Ser Ile Pro
290                        295                    300

Asn Asp Lys Pro Phe Gln Asn Val Asn Lys Val Thr Tyr Gly Lys Cys
305                      310                  315                  320

Pro Lys Tyr Ile Arg Gln Asn Thr Leu Lys Leu Ala Thr Gly Met Arg
            325                  330                  335

Asn Val Pro Glu Lys Gln Ile Arg Gly Ile Phe Gly Ala Ile Ala Gly
               340                   345                  350

Phe Ile Glu Asn Gly Trp Glu Gly Met Val Asp Gly Trp Tyr Gly Phe
           355                  360                  365

Arg Tyr Gln Asn Ser Glu Gly Thr Gly Gln Ala Ala Asp Leu Lys Ser
370                          375                  380

Thr Gln Ala Ala Ile Asp Gln Ile Asn Gly Lys Leu Asn Arg Val Ile
385                      390                  395                  400

Glu Arg Thr Asn Glu Lys Phe His Gln Ile Glu Lys Glu Phe Ser Glu
               405                   410                    415

Val Glu Gly Arg Ile Gln Asp Leu Glu Lys Tyr Val Glu Asp Thr Lys
           420                  425                  430

Ile Asp Leu Trp Ser Tyr Asn Ala Glu Leu Leu Val Ala Leu Lys Asn
            435                  440                  445

Gln His Thr Ile Asp Leu Thr Asp Ala Glu Met Asn Lys Leu Phe Glu
           450                  455                  460

Lys Thr Arg Arg Gln Leu Arg Glu Asn Ala Glu Asp Met Gly Gly Gly
465                          470                  475                  480

Cys Phe Lys Ile Tyr His Lys Cys Asp Asn Ala Cys Ile Gly Ser Ile
               485                   490                  495

Arg Asn Gly Thr Tyr Asp His Tyr Ile Tyr Arg Asp Glu Ala Leu Asn
            500                  505                  510

Asn Arg Phe Gln Ile Lys Gly Val Glu Leu Lys Ser Gly Tyr Lys Asp
           515                  520                  525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565

<210> SEQ ID NO 9
<211> LENGTH: 1695
<212> TYPE: DNA
<213> ORGANISM: Equine influenza virus H3N8

<400> SEQUENCE: 9

```
atgaagacaa ccattatttt gataccactg acccattggg tctacagtca aacccaacc      60
agtggcaaca cacagccac attatgtctg ggacaccatg cagtagcaaa tggaacattg     120
gtaaaaacaa taactgatga ccaaattgag gtgacaaatg ctactgaatt agttcagagc    180
atttcaatag ggaaaatatg caacaactca tatagagttc tagatggaag aaattgcaca    240
ttaatagatg caatgctagg agaccccac tgtgatgtct ttcagtatga gaattgggac     300
ctcttcatag aaagaagcag cgctttcagc agttgctacc catatgacat ccctgactat    360
gcatcgctcc ggtccattgt agcatcctca ggaacattgg aattcacagc agagggattc    420
acatggacag gtgtcactca aaacggaaga agtggatcct gcaaagggg atcagccgat    480
agtttcttta gccgactgaa ttggctaaca gaatctggaa actcttaccc cacattgaat    540
gtgacaatgc ctaacaataa aaatttcgac aaactataca tctgggggat tcatcacccg    600
agctcaaaca aagagcagac aaaattgtac atccaagaat cgggacgagt aacagtctca    660
acaaaaagaa gtcaacaaac aataatccct aacatcggat ctagaccgcg ggtcaggggt    720
caatcaggca ggataagcat atactggacc attgtaaaac ctggagatat cctaatgata    780
aacagtaatg caacttagt tgcaccgcgg ggatatttta aattgaaaac agggaaaagc     840
tctgtaatga atcagatgc acccatagac atttgtgtgt ctgaatgtat tacaccaaat    900
ggaagcatcc ccaacgacaa accatttcaa aatgtgaaca aagttacata tggaaaatgc    960
cccaagtata tcaggcaaaa cactttaaag ctggccactg ggatgaggaa tgtaccagaa   1020
aagcaaatca gaggaatctt tggagcaata gcgggattca tagaaaacgg ctgggaagga   1080
atggttgatg ggtggtatgg attccgatat caaaactcgg aaggaacagg acaagctgca   1140
gatctaaaga gcactcaagc agccatcgac cagatcaatg gaaaattaaa cagagtgatt   1200
gaaaggacca atgagaaatt ccatcaaata gagaaggaat tctcagaagt agaagggagg   1260
atccaggact tggagaagta tgtagaagac accaaaatag acctatggtc ctacaatgca   1320
gaattgctgg tggctctaaa aaatcaacat acaattgact aacagatgc agaaatgaat    1380
aaattattcg agaagactag acgccagtta agagaaaacg cggaagacat gggaggtgga   1440
tgtttcaaga tataccacaa atgtgataat gcatgcattg gatcaataag aaatgggaca   1500
tatgaccatt acatatacag agatgaagca ttaaacaacc ggtttcaaat caaggtgtt    1560
gagttgaaat caggctacaa agattggata ctgtggattt cattcgccat atcatgcttc   1620
ttaatttgcg ttgttctatt gggtttcatt atgtgggctt gccaaaaagg caacatcaga   1680
tgcaacattt gcatt                                                    1695
```

<210> SEQ ID NO 10
<211> LENGTH: 1762

<210> TYPE: DNA
<213> ORGANISM: Equine influenza virus H3N8
<220> FEATURE:
<221> NAME/KEY: CDS
<222> LOCATION: (30)..(1724)
<223> OTHER INFORMATION:

<400> SEQUENCE: 10

```
agcaaaagca ggggatattt ctgtcaatc atg aag aca acc att att ttg ata      53
                                Met Lys Thr Thr Ile Ile Leu Ile
                                  1               5 cta ctg acc cat tgg gtc tac agt caa aac cca acc agt ggc aac aac      101
Leu Leu Thr His Trp Val Tyr Ser Gln Asn Pro Thr Ser Gly Asn Asn
         10                  15                  20 aca gcc aca tta tgt ctg gga cac cat gca gta gca aat gga aca ttg      149
Thr Ala Thr Leu Cys Leu Gly His His Ala Val Ala Asn Gly Thr Leu
 25                  30                  35                  40 gta aaa aca ata act gat gac caa att gag gtg aca aat gct act gaa      197
Val Lys Thr Ile Thr Asp Asp Gln Ile Glu Val Thr Asn Ala Thr Glu
                 45                  50                  55 tta gtt cag agc att tca ata ggg aaa ata tgc aac aac tca tat aga      245
Leu Val Gln Ser Ile Ser Ile Gly Lys Ile Cys Asn Asn Ser Tyr Arg
             60                  65                  70 gtt cta gat gga aga aat tgc aca tta ata gat gca atg cta gga gac      293
Val Leu Asp Gly Arg Asn Cys Thr Leu Ile Asp Ala Met Leu Gly Asp
         75                  80                  85 ccc cac tgt gat gtc ttt cag tat gag aat tgg gac ctc ttc ata gaa      341
Pro His Cys Asp Val Phe Gln Tyr Glu Asn Trp Asp Leu Phe Ile Glu
 90                  95                 100 aga agc agc gct ttc agc agt tgc tac cca tat gac atc cct gac tat      389
Arg Ser Ser Ala Phe Ser Ser Cys Tyr Pro Tyr Asp Ile Pro Asp Tyr
105                 110                 115                 120 gca tcg ctc cgg tcc att gta gca tcc tca gga aca ttg gaa ttc aca      437
Ala Ser Leu Arg Ser Ile Val Ala Ser Ser Gly Thr Leu Glu Phe Thr
                125                 130                 135 gca gag gga ttc aca tgg aca ggt gtc act caa aac gga aga agt gga      485
Ala Glu Gly Phe Thr Trp Thr Gly Val Thr Gln Asn Gly Arg Ser Gly
            140                 145                 150 tcc tgc aaa agg gaa tca gcc gat agt ttc ttt agc cga ctg aat tgg      533
Ser Cys Lys Arg Glu Ser Ala Asp Ser Phe Phe Ser Arg Leu Asn Trp
        155                 160                 165 cta aca gaa tct gga aac tct tac ccc aca ttg aat gtg aca atg cct      581
Leu Thr Glu Ser Gly Asn Ser Tyr Pro Thr Leu Asn Val Thr Met Pro
    170                 175                 180 aac aat aaa aat ttc gac aaa cta tac atc tgg ggg att cat cac ccg      629
Asn Asn Lys Asn Phe Asp Lys Leu Tyr Ile Trp Gly Ile His His Pro
185                 190                 195                 200 agc tca aac aaa gag cag aca aaa ttg tac atc caa gaa tca gga cga      677
Ser Ser Asn Lys Glu Gln Thr Lys Leu Tyr Ile Gln Glu Ser Gly Arg
                205                 210                 215 gta aca gtc tca aca aaa aga agt caa caa aca ata atc cct aac atc      725
Val Thr Val Ser Thr Lys Arg Ser Gln Gln Thr Ile Ile Pro Asn Ile
            220                 225                 230 gga tct aga ccg tgg gtc agg ggt caa tca ggc agg ata agc ata tac      773
Gly Ser Arg Pro Trp Val Arg Gly Gln Ser Gly Arg Ile Ser Ile Tyr
        235                 240                 245 tgg acc att gta aaa cct gga gat atc cta acg ata aac agt aat ggc      821
Trp Thr Ile Val Lys Pro Gly Asp Ile Leu Thr Ile Asn Ser Asn Gly
    250                 255                 260 aac tta gtt gca ccg cgg gga tat ttt aaa ttg aaa aca ggg aaa agc      869
Asn Leu Val Ala Pro Arg Gly Tyr Phe Lys Leu Lys Thr Gly Lys Ser
```

```
                265                 270                 275                 280
tct gta atg aga tca gat gca ccc ata gac att tgt gtg tct gaa tgt       917
Ser Val Met Arg Ser Asp Ala Pro Ile Asp Ile Cys Val Ser Glu Cys
                        285                 290                 295 att aca cca aat gga agc atc ccc aac gac aaa cca ttt caa aat gtg       965
Ile Thr Pro Asn Gly Ser Ile Pro Asn Asp Lys Pro Phe Gln Asn Val
        300                 305                 310 aac aaa gtt aca tat gga aaa tgc ccc aag tat atc agg caa aac act      1013
Asn Lys Val Thr Tyr Gly Lys Cys Pro Lys Tyr Ile Arg Gln Asn Thr
                315                 320                 325 tta aag ctg gcc act ggg atg agg aat gta cca gaa aag caa atc aga      1061
Leu Lys Leu Ala Thr Gly Met Arg Asn Val Pro Glu Lys Gln Ile Arg
        330                 335                 340 gga atc ttt gga gca ata gcg gga ttc ata gaa aac ggc tgg gaa gga      1109
Gly Ile Phe Gly Ala Ile Ala Gly Phe Ile Glu Asn Gly Trp Glu Gly
345                 350                 355                 360 atg gtt gat ggg tgg tat gga ttc cga tat caa aac tcg gaa gga aca      1157
Met Val Asp Gly Trp Tyr Gly Phe Arg Tyr Gln Asn Ser Glu Gly Thr
                365                 370                 375 gga caa gct gca gat cta aag agc act caa gca gcc atc gac cag atc      1205
Gly Gln Ala Ala Asp Leu Lys Ser Thr Gln Ala Ala Ile Asp Gln Ile
        380                 385                 390 aat gga aaa tta aac aga gtg att gaa agg acc aat gag aaa ttc cat      1253
Asn Gly Lys Leu Asn Arg Val Ile Glu Arg Thr Asn Glu Lys Phe His
                395                 400                 405 caa ata gag aag gaa ttc tca gaa gta gaa ggg aga atc cag gac ttg      1301
Gln Ile Glu Lys Glu Phe Ser Glu Val Glu Gly Arg Ile Gln Asp Leu
        410                 415                 420 gag aag tat gta gaa gac acc aaa ata gac cta tgg tcc tac aat gca      1349
Glu Lys Tyr Val Glu Asp Thr Lys Ile Asp Leu Trp Ser Tyr Asn Ala
425                 430                 435                 440 gaa ttg ctg gtg gct cta gaa aat caa cat aca att gac tta aca gat      1397
Glu Leu Leu Val Ala Leu Glu Asn Gln His Thr Ile Asp Leu Thr Asp
                445                 450                 455 gca gaa atg aat aaa tta ttc gag aag act aga cgc cag tta aga gaa      1445
Ala Glu Met Asn Lys Leu Phe Glu Lys Thr Arg Arg Gln Leu Arg Glu
        460                 465                 470 aac gcg gaa gac atg gga ggt gga tgt ttc aag ata tac cac aaa tgt      1493
Asn Ala Glu Asp Met Gly Gly Gly Cys Phe Lys Ile Tyr His Lys Cys
                475                 480                 485 gat aat gca tgc att gga tca ata aga aat ggg aca tat gac cat tac      1541
Asp Asn Ala Cys Ile Gly Ser Ile Arg Asn Gly Thr Tyr Asp His Tyr
        490                 495                 500 ata tac aga gat gaa gca tta aac aac cgg ttt caa atc aaa ggt gtt      1589
Ile Tyr Arg Asp Glu Ala Leu Asn Asn Arg Phe Gln Ile Lys Gly Val
505                 510                 515                 520 gag ttg aaa tca ggc tac aaa gat tgg ata ctg tgg att tca ttc gcc      1637
Glu Leu Lys Ser Gly Tyr Lys Asp Trp Ile Leu Trp Ile Ser Phe Ala
                525                 530                 535 ata tca tgc ttc tta att tgc gtt gtt cta ttg ggt ttc att atg tgg      1685
Ile Ser Cys Phe Leu Ile Cys Val Val Leu Leu Gly Phe Ile Met Trp
        540                 545                 550 gct tgc caa aaa ggc aac atc aga tgc aac att tgc att tgagtaaact      1734
Ala Cys Gln Lys Gly Asn Ile Arg Cys Asn Ile Cys Ile
                555                 560                 565 gatagttaaa aacacccttg tttctact                                       1762

<210> SEQ ID NO 11
<211> LENGTH: 565
```

<210> TYPE: PRT
<213> ORGANISM: Equine influenza virus H3N8

<400> SEQUENCE: 11

```
Met Lys Thr Thr Ile Ile Leu Ile Leu Leu Thr His Trp Val Tyr Ser
1               5                   10                  15

Gln Asn Pro Thr Ser Gly Asn Asn Thr Ala Thr Leu Cys Leu Gly His
            20                  25                  30

His Ala Val Ala Asn Gly Thr Leu Val Lys Thr Ile Thr Asp Asp Gln
        35                  40                  45

Ile Glu Val Thr Asn Ala Thr Glu Leu Val Gln Ser Ile Ser Ile Gly
50                  55                  60

Lys Ile Cys Asn Asn Ser Tyr Arg Val Leu Asp Gly Arg Asn Cys Thr
65                  70                  75                  80

Leu Ile Asp Ala Met Leu Gly Asp Pro His Cys Asp Val Phe Gln Tyr
                85                  90                  95

Glu Asn Trp Asp Leu Phe Ile Glu Arg Ser Ser Ala Phe Ser Ser Cys
            100                 105                 110

Tyr Pro Tyr Asp Ile Pro Asp Tyr Ala Ser Leu Arg Ser Ile Val Ala
        115                 120                 125

Ser Ser Gly Thr Leu Glu Phe Thr Ala Glu Gly Phe Thr Trp Thr Gly
130                 135                 140

Val Thr Gln Asn Gly Arg Ser Gly Ser Cys Lys Arg Glu Ser Ala Asp
145                 150                 155                 160

Ser Phe Phe Ser Arg Leu Asn Trp Leu Thr Glu Ser Gly Asn Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Lys Glu Gln Thr Lys
        195                 200                 205

Leu Tyr Ile Gln Glu Ser Gly Arg Val Thr Val Ser Thr Lys Arg Ser
210                 215                 220

Gln Gln Thr Ile Ile Pro Asn Ile Gly Ser Arg Pro Trp Val Arg Gly
225                 230                 235                 240

Gln Ser Gly Arg Ile Ser Ile Tyr Trp Thr Ile Val Lys Pro Gly Asp
                245                 250                 255

Ile Leu Thr Ile Asn Ser Asn Gly Asn Leu Val Ala Pro Arg Gly Tyr
            260                 265                 270

Phe Lys Leu Lys Thr Gly Lys Ser Ser Val Met Arg Ser Asp Ala Pro
        275                 280                 285

Ile Asp Ile Cys Val Ser Glu Cys Ile Thr Pro Asn Gly Ser Ile Pro
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Ile Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
370                 375                 380

Thr Gln Ala Ala Ile Asp Gln Ile Asn Gly Lys Leu Asn Arg Val Ile
385                 390                 395                 400
```

```
Glu Arg Thr Asn Glu Lys Phe His Gln Ile Glu Lys Glu Phe Ser Glu
                405                 410                 415
Val Glu Gly Arg Ile Gln Asp Leu Glu Lys Tyr Val Glu Asp Thr Lys
            420                 425                 430
Ile Asp Leu Trp Ser Tyr Asn Ala Glu Leu Leu Val Ala Leu Glu Asn
        435                 440                 445
Gln His Thr Ile Asp Leu Thr Asp Ala Glu Met Asn Lys Leu Phe Glu
    450                 455                 460
Lys Thr Arg Arg Gln Leu Arg Glu Asn Ala Glu Asp Met Gly Gly Gly
465                 470                 475                 480
Cys Phe Lys Ile Tyr His Lys Cys Asp Asn Ala Cys Ile Gly Ser Ile
                485                 490                 495
Arg Asn Gly Thr Tyr Asp His Tyr Ile Tyr Arg Asp Glu Ala Leu Asn
            500                 505                 510
Asn Arg Phe Gln Ile Lys Gly Val Glu Leu Lys Ser Gly Tyr Lys Asp
        515                 520                 525
Trp Ile Leu Trp Ile Ser Phe Ala Ile Ser Cys Phe Leu Ile Cys Val
    530                 535                 540
Val Leu Leu Gly Phe Ile Met Trp Ala Cys Gln Lys Gly Asn Ile Arg
545                 550                 555                 560
Cys Asn Ile Cys Ile
            565

<210> SEQ ID NO 12
<211> LENGTH: 1695
<212> TYPE: DNA
<213> ORGANISM: Equine influenza virus H3N8

<400> SEQUENCE: 12
atgaagacaa ccattatttt gatactactg acccattggg tctacagtca aaacccaacc      60
agtggcaaca acacagccac attatgtctg ggacaccatg cagtagcaaa tggaacattg     120
gtaaaaacaa taactgatga ccaaattgag gtgacaaatg ctactgaatt agttcagagc     180
atttcaatag ggaaaatatg caacaactca tatagagttc tagatggaag aaattgcaca     240
ttaatagatg caatgctagg agaccccac tgtgatgtct ttcagtatga aattgggac      300
ctcttcatag aaagaagcag cgcttcagc agttgctacc catatgacat ccctgactat     360
gcatcgctcc ggtccattgt agcatcctca ggaacattgg aattcacagc agagggattc     420
acatggacag gtgtcactca aaacggaaga agtggatcct gcaaaagggga atcagccgat     480
agtttcttta gccgactgaa ttggctaaca gaatctggaa actcttaccc cacattgaat     540
gtgacaatgc taacaataa aaatttcgac aaactataca tctgggggat tcatcacccg     600
agctcaaaca agagcagac aaaattgtac atccaagaat caggacgagt aacagtctca     660
acaaaaagaa gtcaacaaac aataatccct aacatcggat ctagaccgtg gtcaggggt     720
caatcaggca ggataagcat atactggacc attgtaaaac ctggagatat cctaacgata     780
aacagtaatg caacttagt tgcaccgcgg ggatatttta aattgaaaac agggaaagc     840
tctgtaatga gatcagatgc acccatagac atttgtgtgt ctgaatgtat taccaaat      900
ggaagcatcc ccaacgacaa accatttcaa aatgtgaaca agttacata tggaaaatgc     960
cccaagtata tcaggcaaaa cactttaaag ctggccactg ggatgaggaa tgtaccagaa    1020
aagcaaatca gaggaatctt tggagcaata gcgggattca gaaaaacgg ctgggaagga    1080
atggttgatg ggtggtatgg attccgatat caaaactcgg aaggaacagg acaagctgca    1140
```

-continued

```
gatctaaaga gcactcaagc agccatcgac cagatcaatg gaaaattaaa cagagtgatt   1200
gaaaggacca atgagaaatt ccatcaaata gagaaggaat tctcagaagt agaagggaga   1260
atccaggact tggagaagta tgtagaagac accaaaatag acctatggtc ctacaatgca   1320
gaattgctgg tggctctaga aaatcaacat acaattgact taacagatgc agaaatgaat   1380
aaattattcg agaagactag acgccagtta agagaaaacg cggaagacat gggaggtgga   1440
tgtttcaaga tataccacaa atgtgataat gcatgcattg gatcaataag aaatgggaca   1500
tatgaccatt acatatacag agatgaagca ttaaacaacc ggtttcaaat caaaggtgtt   1560
gagttgaaat caggctacaa agattggata ctgtggattt cattcgccat atcatgcttc   1620
ttaatttgcg ttgttctatt gggtttcatt atgtgggctt gccaaaaagg caacatcaga   1680
tgcaacattt gcatt                                                   1695

<210> SEQ ID NO 13
<211> LENGTH: 1241
<212> TYPE: DNA
<213> ORGANISM: Equine influenza virus H3N8
<220> FEATURE:
<221> NAME/KEY: CDS
<222> LOCATION: (28)..(1239)
<223> OTHER INFORMATION:

<400> SEQUENCE: 13
agcaaaagca ggtcaaatat attcaat atg gag aga ata aaa gaa ctg aga gat    54
                                Met Glu Arg Ile Lys Glu Leu Arg Asp
                                  1               5 cta atg tca caa tcc cgc acc cgc gag ata cta aca aaa act act gtg   102
Leu Met Ser Gln Ser Arg Thr Arg Glu Ile Leu Thr Lys Thr Thr Val
 10                  15                  20                  25 gac cac atg gcc ata atc aag aaa tac aca tca gga aga caa gag aag   150
Asp His Met Ala Ile Ile Lys Lys Tyr Thr Ser Gly Arg Gln Glu Lys
                 30                  35                  40 aac ccc gca ctt agg atg aag tgg atg atg gca atg aaa tac cca att   198
Asn Pro Ala Leu Arg Met Lys Trp Met Met Ala Met Lys Tyr Pro Ile
             45                  50                  55 aca gca gat aag agg ata atg gaa atg att cct gag aga aat gaa cag   246
Thr Ala Asp Lys Arg Ile Met Glu Met Ile Pro Glu Arg Asn Glu Gln
         60                  65                  70 ggg caa acc ctt tgg agc aaa acg aac gat gct ggc tca gac cgc gta   294
Gly Gln Thr Leu Trp Ser Lys Thr Asn Asp Ala Gly Ser Asp Arg Val
     75                  80                  85 atg gta tca cct ctg gca gtg aca tgg tgg aat agg aat gga cca aca   342
Met Val Ser Pro Leu Ala Val Thr Trp Trp Asn Arg Asn Gly Pro Thr
 90                  95                 100                 105 acg agc aca att cat tat cca aaa gtc tac aaa act tat ttt gaa aaa   390
Thr Ser Thr Ile His Tyr Pro Lys Val Tyr Lys Thr Tyr Phe Glu Lys
                110                 115                 120 gtt gaa aga tta aaa cac gga acc ttt ggc ccc gtt cat ttt agg aat   438
Val Glu Arg Leu Lys His Gly Thr Phe Gly Pro Val His Phe Arg Asn
            125                 130                 135 caa gtc aag ata aga cgg aga gtt gat gta aac cct ggt cac gcg gac   486
Gln Val Lys Ile Arg Arg Arg Val Asp Val Asn Pro Gly His Ala Asp
        140                 145                 150 ctc agt gcc aaa gaa gca caa gat gtg atc atg gaa gtt gtt ttc cca   534
Leu Ser Ala Lys Glu Ala Gln Asp Val Ile Met Glu Val Val Phe Pro
    155                 160                 165 aat gaa gtg gga gcc aga att cta aca tcg gaa tca caa cta aca ata   582
Asn Glu Val Gly Ala Arg Ile Leu Thr Ser Glu Ser Gln Leu Thr Ile
```

-continued 170 175 180 185 acc aaa gag aaa aaa gaa gaa ctt cag gac tgc aaa att gcc ccc ttg 630
Thr Lys Glu Lys Lys Glu Glu Leu Gln Asp Cys Lys Ile Ala Pro Leu
190 195 200 atg gta gca tac atg cta gaa aga gag ttg gtc cga aaa aca aga ttc 678
Met Val Ala Tyr Met Leu Glu Arg Glu Leu Val Arg Lys Thr Arg Phe
205 210 215 ctc cca gtg gct ggc gga aca agc agt gta tac att gaa gtg ttg cat 726
Leu Pro Val Ala Gly Gly Thr Ser Ser Val Tyr Ile Glu Val Leu His
220 225 230 ctg act cag gga aca tgc tgg gaa caa atg tac acc cca gga gga gaa 774
Leu Thr Gln Gly Thr Cys Trp Glu Gln Met Tyr Thr Pro Gly Gly Glu
235 240 245 gtt aga aac gat gac att gat caa agt tta att att gct gcc cgg aac 822
Val Arg Asn Asp Asp Ile Asp Gln Ser Leu Ile Ile Ala Ala Arg Asn
250 255 260 265 ata gtg aga aga gcg aca gta tca gca gat cca cta gca tcc ctg ctg 870
Ile Val Arg Arg Ala Thr Val Ser Ala Asp Pro Leu Ala Ser Leu Leu
270 275 280 gaa atg tgc cac agt aca cag att ggt gga ata agg atg gta gac atc 918
Glu Met Cys His Ser Thr Gln Ile Gly Gly Ile Arg Met Val Asp Ile
285 290 295 ctt aag cag aat cca aca gag gaa caa gct gtg gat ata tgc aaa gca 966
Leu Lys Gln Asn Pro Thr Glu Glu Gln Ala Val Asp Ile Cys Lys Ala
300 305 310 gca atg ggg tta aga att agc tca tca ttc agc ttt ggt gga ttc acc 1014
Ala Met Gly Leu Arg Ile Ser Ser Ser Phe Ser Phe Gly Gly Phe Thr
315 320 325 ttt aag aga aca agt gga tca tca gtc aag aga gaa gaa gaa atg ctt 1062
Phe Lys Arg Thr Ser Gly Ser Ser Val Lys Arg Glu Glu Glu Met Leu
330 335 340 345 acg ggc aac ctt caa aca ttg aaa ata aga gtg cat gaa ggc tat gaa 1110
Thr Gly Asn Leu Gln Thr Leu Lys Ile Arg Val His Glu Gly Tyr Glu
350 355 360 gaa ttc aca atg gtc gga aga aga gca aca gcc att ctc aga aag gca 1158
Glu Phe Thr Met Val Gly Arg Arg Ala Thr Ala Ile Leu Arg Lys Ala
365 370 375 acc aga aga ttg att caa ttg ata gta agt ggg aga gat gaa caa tca 1206
Thr Arg Arg Leu Ile Gln Leu Ile Val Ser Gly Arg Asp Glu Gln Ser
380 385 390 att gct gaa gca ata att gta gcc atg gtg ttt tc 1241
Ile Ala Glu Ala Ile Ile Val Ala Met Val Phe
395 400

<210> SEQ ID NO 14
<211> LENGTH: 404
<212> TYPE: PRT
<213> ORGANISM: Equine influenza virus H3N8

<400> SEQUENCE: 14

Met Glu Arg Ile Lys Glu Leu Arg Asp Leu Met Ser Gln Ser Arg Thr
1 5 10 15

Arg Glu Ile Leu Thr Lys Thr Thr Val Asp His Met Ala Ile Ile Lys
20 25 30

Lys Tyr Thr Ser Gly Arg Gln Glu Lys Asn Pro Ala Leu Arg Met Lys
35 40 45

Trp Met Met Ala Met Lys Tyr Pro Ile Thr Ala Asp Lys Arg Ile Met
50 55 60

Glu Met Ile Pro Glu Arg Asn Glu Gln Gly Gln Thr Leu Trp Ser Lys

| | | | | | | | 65 | | | 70 | | | 75 | | | 80 | |
|---|---|---|---|---|---|---|---|---|---|---|---|---|---|---|---|---|---|

Thr Asn Asp Ala Gly Ser Asp Arg Val Met Val Ser Pro Leu Ala Val
         85       90      95

Thr Trp Trp Asn Arg Asn Gly Pro Thr Thr Ser Thr Ile His Tyr Pro
     100       105      110

Lys Val Tyr Lys Thr Tyr Phe Glu Lys Val Glu Arg Leu Lys His Gly
    115       120      125

Thr Phe Gly Pro Val His Phe Arg Asn Gln Val Lys Ile Arg Arg Arg
  130       135      140

Val Asp Val Asn Pro Gly His Ala Asp Leu Ser Ala Lys Glu Ala Gln
145        150       155      160

Asp Val Ile Met Glu Val Val Phe Pro Asn Glu Val Gly Ala Arg Ile
     165       170      175

Leu Thr Ser Glu Ser Gln Leu Thr Ile Thr Lys Glu Lys Lys Glu Glu
    180       185      190

Leu Gln Asp Cys Lys Ile Ala Pro Leu Met Val Ala Tyr Met Leu Glu
   195       200      205

Arg Glu Leu Val Arg Lys Thr Arg Phe Leu Pro Val Ala Gly Gly Thr
210        215       220

Ser Ser Val Tyr Ile Glu Val Leu His Leu Thr Gln Gly Thr Cys Trp
225        230       235      240

Glu Gln Met Tyr Thr Pro Gly Gly Glu Val Arg Asn Asp Asp Ile Asp
    245       250      255

Gln Ser Leu Ile Ile Ala Ala Arg Asn Ile Val Arg Arg Ala Thr Val
  260       265      270

Ser Ala Asp Pro Leu Ala Ser Leu Leu Glu Met Cys His Ser Thr Gln
   275       280      285

Ile Gly Gly Ile Arg Met Val Asp Ile Leu Lys Gln Asn Pro Thr Glu
    290       295      300

Glu Gln Ala Val Asp Ile Cys Lys Ala Ala Met Gly Leu Arg Ile Ser
305        310       315      320

Ser Ser Phe Ser Phe Gly Gly Phe Thr Phe Lys Arg Thr Ser Gly Ser
    325       330      335

Ser Val Lys Arg Glu Glu Glu Met Leu Thr Gly Asn Leu Gln Thr Leu
   340       345      350

Lys Ile Arg Val His Glu Gly Tyr Glu Glu Phe Thr Met Val Gly Arg
    355       360      365

Arg Ala Thr Ala Ile Leu Arg Lys Ala Thr Arg Arg Leu Ile Gln Leu
  370       375      380

Ile Val Ser Gly Arg Asp Glu Gln Ser Ile Ala Glu Ala Ile Ile Val
385        390       395      400

Ala Met Val Phe

<210> SEQ ID NO 15
<211> LENGTH: 1214
<212> TYPE: DNA
<213> ORGANISM: Equine influenza virus H3N8

<400> SEQUENCE: 15

| | | | | |
|---|---|---|---|---|
| atggagagaa | taaagaact | gagagatcta | atgtcacaat | cccgcacccg | cgagatacta | 60 |
| acaaaaacta | ctgtggacca | catggccata | atcaagaaat | acacatcagg | aagacaagag | 120 |
| aagaaccccg | cacttaggat | gaagtggatg | atggcaatga | ataccccaat | tacagcagat | 180 |
| aagaggataa | tggaaatgat | tcctgagaga | aatgaacagg | ggcaaaccct | ttggagcaaa | 240 |

-continued

```
acgaacgatg ctggctcaga ccgcgtaatg gtatcacctc tggcagtgac atggtggaat      300
aggaatggac caacaacgag cacaattcat tatccaaaag tctacaaaac ttattttgaa      360
aaagttgaaa gattaaaaca cggaaccttt ggccccgttc attttaggaa tcaagtcaag      420
ataagacgga gagttgatgt aaaccctggt cacgcggacc tcagtgccaa agaagcacaa      480
gatgtgatca tggaagttgt tttcccaaat gaagtgggag ccagaattct aacatcggaa      540
tcacaactaa caataaccaa agagaaaaaa gaagaacttc aggactgcaa aattgccccc      600
ttgatggtag catacatgct agaaagagag ttggtccgaa aaacaagatt cctcccagtg      660
gctggcggaa caagcagtgt atacattgaa gtgttgcatc tgactcaggg aacatgctgg      720
gaacaaatgt acaccccagg aggagaagtt agaaacgatg acattgatca agtttaatt       780 attgctgccc ggaacatagt gagaagagcg acagtatcag cagatccact agcatccctg      840
ctggaaatgt gccacagtac acagattggt ggaataagga tggtagacat ccttaagcag      900
aatccaacag aggaacaagc tgtggatata tgcaaagcag caatgggggtt aagaattagc     960 tcatcattca gctttggtgg attcaccttt aagagaacaa gtggatcatc agtcaagaga     1020
gaagaagaaa tgcttacggg caaccttcaa acattgaaaa taagagtgca tgaaggctat     1080
gaagaattca caatggtcgg aagaagagca acagccattc tcagaaaggc aaccagaaga     1140
ttgattcaat tgatagtaag tgggagagat gaacaatcaa ttgctgaagc aataattgta     1200
gccatggtgt tttc                                                       1214
```

```
<210> SEQ ID NO 16
<211> LENGTH: 1241
<212> TYPE: DNA
<213> ORGANISM: Equine influenza virus H3N8
<220> FEATURE:
<221> NAME/KEY: CDS
<222> LOCATION: (28)..(1239)
<223> OTHER INFORMATION:

<400> SEQUENCE: 16
```

```
agcaaaagca ggtcaaatat attcaat atg gag aga ata aaa gaa ctg aga gat      54
                                Met Glu Arg Ile Lys Glu Leu Arg Asp
                                  1               5 cta atg tca caa tcc cgc acc cgc gag ata cta aca aaa act act gtg       102
Leu Met Ser Gln Ser Arg Thr Arg Glu Ile Leu Thr Lys Thr Thr Val
 10              15                  20                  25 gac cac atg gcc ata atc aag aaa tac aca tca gga aga caa gag aag       150
Asp His Met Ala Ile Ile Lys Lys Tyr Thr Ser Gly Arg Gln Glu Lys
                 30                  35                  40 aac ccc gca ctt agg atg aag tgg atg atg gca atg aaa tac cca att       198
Asn Pro Ala Leu Arg Met Lys Trp Met Met Ala Met Lys Tyr Pro Ile
             45                  50                  55 aca gca gat aag agg ata atg gaa atg att cct gag aga aat gaa cag       246
Thr Ala Asp Lys Arg Ile Met Glu Met Ile Pro Glu Arg Asn Glu Gln
         60                  65                  70 ggg caa acc ctt tgg agc aaa acg aac gat gct ggc tca gac cgc gta       294
Gly Gln Thr Leu Trp Ser Lys Thr Asn Asp Ala Gly Ser Asp Arg Val
     75                  80                  85 atg gta tca cct ctg gca gtg aca tgg tgg aat agg aat gga cca aca       342
Met Val Ser Pro Leu Ala Val Thr Trp Trp Asn Arg Asn Gly Pro Thr
 90                  95                 100                 105 acg agc aca att cat tat cca aaa gtc cac aaa act tat ttt gaa aaa       390
Thr Ser Thr Ile His Tyr Pro Lys Val His Lys Thr Tyr Phe Glu Lys
                110                 115                 120
```

```
gtt gaa aga tta aaa cac gga acc ttt ggc ccc gtt cat ttt agg aat      438
Val Glu Arg Leu Lys His Gly Thr Phe Gly Pro Val His Phe Arg Asn
        125                 130                 135 caa gtc aag ata aga cgg aga gtt gat gta aac cct ggt cac gcg gac      486
Gln Val Lys Ile Arg Arg Arg Val Asp Val Asn Pro Gly His Ala Asp
        140                 145                 150 ctc agt gcc aaa gaa gca caa gat gtg atc atg gaa gtt gtt ttc cca      534
Leu Ser Ala Lys Glu Ala Gln Asp Val Ile Met Glu Val Val Phe Pro
    155                 160                 165 aat gaa gtg gga gcc aga att cta aca tcg gaa tca caa cta aca ata      582
Asn Glu Val Gly Ala Arg Ile Leu Thr Ser Glu Ser Gln Leu Thr Ile
170                 175                 180                 185 acc aaa gag aaa aaa gaa gaa ctt cag gac tgc aaa att gcc ccc ttg      630
Thr Lys Glu Lys Lys Glu Glu Leu Gln Asp Cys Lys Ile Ala Pro Leu
                190                 195                 200 atg gta gca tac atg cta gaa aga gag ttg gtc cga aaa aca aga ttc      678
Met Val Ala Tyr Met Leu Glu Arg Glu Leu Val Arg Lys Thr Arg Phe
                205                 210                 215 ctc cca gtg gct ggc gga aca agc agt gta tac att gaa gtg ttg cat      726
Leu Pro Val Ala Gly Gly Thr Ser Ser Val Tyr Ile Glu Val Leu His
            220                 225                 230 ctg act cag gga aca tgc tgg gaa caa atg tac acc cca gga gga gaa      774
Leu Thr Gln Gly Thr Cys Trp Glu Gln Met Tyr Thr Pro Gly Gly Glu
        235                 240                 245 gtt aga aac gat gac att gat caa agt tta att att gct gcc cgg aac      822
Val Arg Asn Asp Asp Ile Asp Gln Ser Leu Ile Ile Ala Ala Arg Asn
250                 255                 260                 265 ata gtg aga aga gcg aca gta tca gca gat cca cta gca tcc ctg ctg      870
Ile Val Arg Arg Ala Thr Val Ser Ala Asp Pro Leu Ala Ser Leu Leu
                270                 275                 280 gaa atg tgc cac agt aca cag att ggt gga ata agg atg gta gac atc      918
Glu Met Cys His Ser Thr Gln Ile Gly Gly Ile Arg Met Val Asp Ile
                285                 290                 295 ctt aag cag aat cca aca gag gaa caa gct gtg gat ata tgc aaa gca      966
Leu Lys Gln Asn Pro Thr Glu Glu Gln Ala Val Asp Ile Cys Lys Ala
            300                 305                 310 gca atg ggg tta aga att agc tca tca ttc agc ttt ggt gga ttc acc     1014
Ala Met Gly Leu Arg Ile Ser Ser Ser Phe Ser Phe Gly Gly Phe Thr
        315                 320                 325 ttt aag aga aca agt gga tca tca gtc aag aga gaa gaa atg ctt         1062
Phe Lys Arg Thr Ser Gly Ser Ser Val Lys Arg Glu Glu Glu Met Leu
330                 335                 340                 345 acg ggc aac ctt caa aca ttg aaa ata aga gtg cat gaa ggc tat gaa     1110
Thr Gly Asn Leu Gln Thr Leu Lys Ile Arg Val His Glu Gly Tyr Glu
                350                 355                 360 gaa ttc aca atg gtc gga aga aga gca aca gcc att ctc aga aag gca     1158
Glu Phe Thr Met Val Gly Arg Arg Ala Thr Ala Ile Leu Arg Lys Ala
                365                 370                 375 acc aga aga ttg att caa ttg ata gta agt ggg aga gat gaa caa tca     1206
Thr Arg Arg Leu Ile Gln Leu Ile Val Ser Gly Arg Asp Glu Gln Ser
            380                 385                 390 att gct gaa gca ata att gta gcc atg gtg ttt tc                      1241
Ile Ala Glu Ala Ile Ile Val Ala Met Val Phe
        395                 400

<210> SEQ ID NO 17
<211> LENGTH: 404
<212> TYPE: PRT
<213> ORGANISM: Equine influenza virus H3N8

<400> SEQUENCE: 17
```

-continued

```
Met Glu Arg Ile Lys Glu Leu Arg Asp Leu Met Ser Gln Ser Arg Thr
 1               5                  10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val His Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
370                 375                 380

Ile Val Ser Gly Arg Asp Glu Gln Ser Ile Ala Glu Ala Ile Ile Val
385                 390                 395                 400

Ala Met Val Phe
```

<210> SEQ ID NO 18
<211> LENGTH: 1214
<212> TYPE: DNA
<213> ORGANISM: Equine influenza virus H3N8

<400> SEQUENCE: 18

```
atggagagaa taaaagaact gagagatcta atgtcacaat cccgcacccg cgagatacta      60
acaaaaacta ctgtggacca catggccata atcaagaaat acacatcagg aagacaagag     120
aagaaccccg cacttaggat gaagtggatg atggcaatga atacccaat tacagcagat      180
aagaggataa tggaaatgat tcctgagaga aatgaacagg gcaaacccct ttggagcaaa     240
acgaacgatg ctggctcaga ccgcgtaatg gtatcacctc tggcagtgac atggtggaat     300
aggaatggac caacaacgag cacaattcat tatccaaaag tccacaaaac ttattttgaa     360
aaagttgaaa gattaaaaca cggaaccttt ggccccgttc attttaggaa tcaagtcaag     420
ataagacgga gagttgatgt aaaccctggt cacgcggacc tcagtgccaa agaagcacaa     480
gatgtgatca tggaagttgt tttcccaaat gaagtgggag ccagaattct aacatcggaa     540
tcacaactaa caataaccaa agagaaaaaa gaagaacttc aggactgcaa aattgccccc     600
ttgatggtag catacatgct agaaagagag ttggtccgaa aaacaagatt cctcccagtg     660
gctggcggaa caagcagtgt atacattgaa gtgttgcatc tgactcaggg aacatgctgg     720
gaacaaatgt acacccccagg aggagaagtt agaaacgatg acattgatca agtttaatt      780
attgctgccc ggaacatagt gagaagagcg acagtatcag cagatccact agcatccctg     840
ctggaaatgt gccacagtac acagattggt ggaataagga tggtagacat ccttaagcag     900
aatccaacag aggaacaagc tgtggatata tgcaaagcag caatggggtt aagaattagc     960
tcatcattca gctttggtgg attcaccttt aagagaacaa gtggatcatc agtcaagaga    1020
gaagaagaaa tgcttacggg caaccttcaa acattgaaaa taagagtgca tgaaggctat    1080
gaagaattca atggtcgg aagaagagca acagccattc tcagaaaggc aaccagaaga    1140
ttgattcaat tgatagtaag tgggagagat gaacaatcaa ttgctgaagc aataattgta    1200
gccatggtgt tttc                                                      1214
```

<210> SEQ ID NO 19
<211> LENGTH: 1233
<212> TYPE: DNA
<213> ORGANISM: Equine influenza virus H3N8
<220> FEATURE:
<221> NAME/KEY: CDS
<222> LOCATION: (3)..(1196)
<223> OTHER INFORMATION:

<400> SEQUENCE: 19

```
ta gaa ttc aca atg gtc gga aga aga gca aca gcc att ctc aga aag       47
   Glu Phe Thr Met Val Gly Arg Arg Ala Thr Ala Ile Leu Arg Lys
   1               5                  10                  15 gca acc aga aga ttg att caa ttg ata gta agt ggg aga gat gaa caa       95
Ala Thr Arg Arg Leu Ile Gln Leu Ile Val Ser Gly Arg Asp Glu Gln
                20                  25                  30 tca att gct gaa gca ata att gta gcc atg gtg ttt tcg caa gaa gat      143
Ser Ile Ala Glu Ala Ile Ile Val Ala Met Val Phe Ser Gln Glu Asp
            35                  40                  45 tgc atg ata aaa gca gtt cga ggc gat ttg aac ttc gtt aat aga gca      191
Cys Met Ile Lys Ala Val Arg Gly Asp Leu Asn Phe Val Asn Arg Ala
        50                  55                  60 aat cag cgc ttg aac ccc atg cat caa ctc ttg agg cat ttc caa aaa      239
Asn Gln Arg Leu Asn Pro Met His Gln Leu Leu Arg His Phe Gln Lys
```

```
          65                   70                   75
gat gca aaa gtg ctt ttc cag aat tgg ggg att gaa ccc atc gac aat    287
Asp Ala Lys Val Leu Phe Gln Asn Trp Gly Ile Glu Pro Ile Asp Asn
 80              85                   90                   95 gtg atg gga atg att gga ata ttg cct gac atg acc cca agc acc gag    335
Val Met Gly Met Ile Gly Ile Leu Pro Asp Met Thr Pro Ser Thr Glu
                100                 105                 110 atg tca ttg aga gga gtg aga gtc agc aaa atg gga gtg gat gag tac    383
Met Ser Leu Arg Gly Val Arg Val Ser Lys Met Gly Val Asp Glu Tyr
            115                 120                 125 tcc agc act gag aga gtg gtg gtg agc att gac cgt ttt tta aga gtt    431
Ser Ser Thr Glu Arg Val Val Val Ser Ile Asp Arg Phe Leu Arg Val
        130                 135                 140 cgg gat caa agg gga aac ata cta ctg tcc cct gaa gag gtc agt gaa    479
Arg Asp Gln Arg Gly Asn Ile Leu Leu Ser Pro Glu Glu Val Ser Glu
    145                 150                 155 aca caa gga acg gaa aag ctg aca ata att tat tca tca tca atg atg    527
Thr Gln Gly Thr Glu Lys Leu Thr Ile Ile Tyr Ser Ser Ser Met Met
160                 165                 170                 175 tgg gag att aat ggt ccc gaa tca gtg ttg gtc aat act tat caa tgg    575
Trp Glu Ile Asn Gly Pro Glu Ser Val Leu Val Asn Thr Tyr Gln Trp
                180                 185                 190 atc atc agg aac tgg gaa att gtg aaa att caa tgg tca cag gat ccc    623
Ile Ile Arg Asn Trp Glu Ile Val Lys Ile Gln Trp Ser Gln Asp Pro
            195                 200                 205 aca atg tta tac aat aag ata gaa ttt gag cca ttc cag tcc ctg gtc    671
Thr Met Leu Tyr Asn Lys Ile Glu Phe Glu Pro Phe Gln Ser Leu Val
        210                 215                 220 cct agg gcc acc aga agc caa tac agc ggt ttc gta aga acc ctg ttt    719
Pro Arg Ala Thr Arg Ser Gln Tyr Ser Gly Phe Val Arg Thr Leu Phe
    225                 230                 235 cag caa atg cga gat gta ctt gga aca ttt gat act gct caa ata ata    767
Gln Gln Met Arg Asp Val Leu Gly Thr Phe Asp Thr Ala Gln Ile Ile
240                 245                 250                 255 aaa ctc ctc cct ttt gcc gct gct cct ccg gaa cag agt agg atg cag    815
Lys Leu Leu Pro Phe Ala Ala Ala Pro Pro Glu Gln Ser Arg Met Gln
                260                 265                 270 ttc tct tct ttg act gtt aat gta aga gga tcg gga atg agg ata ctt    863
Phe Ser Ser Leu Thr Val Asn Val Arg Gly Ser Gly Met Arg Ile Leu
            275                 280                 285 gta aga ggc aat tcc cca gtg ttc aac tac aat aaa gcc act aag agg    911
Val Arg Gly Asn Ser Pro Val Phe Asn Tyr Asn Lys Ala Thr Lys Arg
        290                 295                 300 ctc aca gtc ctc gga aag gat gca ggt gcg ctt act gaa gac cca gat    959
Leu Thr Val Leu Gly Lys Asp Ala Gly Ala Leu Thr Glu Asp Pro Asp
    305                 310                 315 gaa ggt acg gct gga gta gaa tct gct gtt cta aga ggg ttt ctc att   1007
Glu Gly Thr Ala Gly Val Glu Ser Ala Val Leu Arg Gly Phe Leu Ile
320                 325                 330                 335 tta ggt aaa gaa aac aag aga tat ggc cca gca cta agc atc aat gaa   1055
Leu Gly Lys Glu Asn Lys Arg Tyr Gly Pro Ala Leu Ser Ile Asn Glu
                340                 345                 350 ctg agc aaa ctt gca aaa ggg gag aaa gct aat gtg cta att ggg caa   1103
Leu Ser Lys Leu Ala Lys Gly Glu Lys Ala Asn Val Leu Ile Gly Gln
            355                 360                 365 ggg gac gtg gtg ttg gta atg aaa cgg aaa cgt gac tct agc ata ctt   1151
Gly Asp Val Val Leu Val Met Lys Arg Lys Arg Asp Ser Ser Ile Leu
        370                 375                 380 act gac agc cag aca gcg acc aaa agg att cgg atg gcc atc aat       1196
```

```
Thr Asp Ser Gln Thr Ala Thr Lys Arg Ile Arg Met Ala Ile Asn
    385                 390                 395 tagtgttgaa ttgtttaaaa acgaccttgt ttctact                         1233

<210> SEQ ID NO 20
<211> LENGTH: 398
<212> TYPE: PRT
<213> ORGANISM: Equine influenza virus H3N8

<400> SEQUENCE: 20

Glu Phe Thr Met Val Gly Arg Arg Ala Thr Ala Ile Leu Arg Lys Ala
1               5                   10                  15

Thr Arg Arg Leu Ile Gln Leu Ile Val Ser Gly Arg Asp Glu Gln Ser
            20                  25                  30

Ile Ala Glu Ala Ile Ile Val Ala Met Val Phe Ser Gln Glu Asp Cys
        35                  40                  45

Met Ile Lys Ala Val Arg Gly Asp Leu Asn Phe Val Asn Arg Ala Asn
    50                  55                  60

Gln Arg Leu Asn Pro Met His Gln Leu Leu Arg His Phe Gln Lys Asp
65                  70                  75                  80

Ala Lys Val Leu Phe Gln Asn Trp Gly Ile Glu Pro Ile Asp Asn Val
                85                  90                  95

Met Gly Met Ile Gly Ile Leu Pro Asp Met Thr Pro Ser Thr Glu Met
            100                 105                 110

Ser Leu Arg Gly Val Arg Val Ser Lys Met Gly Val Asp Glu Tyr Ser
        115                 120                 125

Ser Thr Glu Arg Val Val Val Ser Ile Asp Arg Phe Leu Arg Val Arg
    130                 135                 140

Asp Gln Arg Gly Asn Ile Leu Leu Ser Pro Glu Glu Val Ser Glu Thr
145                 150                 155                 160

Gln Gly Thr Glu Lys Leu Thr Ile Ile Tyr Ser Ser Ser Met Met Trp
                165                 170                 175

Glu Ile Asn Gly Pro Glu Ser Val Leu Val Asn Thr Tyr Gln Trp Ile
            180                 185                 190

Ile Arg Asn Trp Glu Ile Val Lys Ile Gln Trp Ser Gln Asp Pro Thr
        195                 200                 205

Met Leu Tyr Asn Lys Ile Glu Phe Glu Pro Phe Gln Ser Leu Val Pro
    210                 215                 220

Arg Ala Thr Arg Ser Gln Tyr Ser Gly Phe Val Arg Thr Leu Phe Gln
225                 230                 235                 240

Gln Met Arg Asp Val Leu Gly Thr Phe Asp Thr Ala Gln Ile Ile Lys
                245                 250                 255

Leu Leu Pro Phe Ala Ala Ala Pro Pro Glu Gln Ser Arg Met Gln Phe
            260                 265                 270

Ser Ser Leu Thr Val Asn Val Arg Gly Ser Gly Met Arg Ile Leu Val
        275                 280                 285

Arg Gly Asn Ser Pro Val Phe Asn Tyr Asn Lys Ala Thr Lys Arg Leu
    290                 295                 300

Thr Val Leu Gly Lys Asp Ala Gly Ala Leu Thr Glu Asp Pro Asp Glu
305                 310                 315                 320

Gly Thr Ala Gly Val Glu Ser Ala Val Leu Arg Gly Phe Leu Ile Leu
                325                 330                 335

Gly Lys Glu Asn Lys Arg Tyr Gly Pro Ala Leu Ser Ile Asn Glu Leu
            340                 345                 350
```

```
Ser Lys Leu Ala Lys Gly Glu Lys Ala Asn Val Leu Ile Gly Gln Gly
        355                 360                 365

Asp Val Val Leu Val Met Lys Arg Lys Arg Asp Ser Ser Ile Leu Thr
    370                 375                 380

Asp Ser Gln Thr Ala Thr Lys Arg Ile Arg Met Ala Ile Asn
385                 390                 395

<210> SEQ ID NO 21
<211> LENGTH: 1194
<212> TYPE: DNA
<213> ORGANISM: Equine influenza virus H3N8

<400> SEQUENCE: 21
gaattcacaa tggtcggaag aagagcaaca gccattctca gaaaggcaac cagaagattg      60
attcaattga tagtaagtgg gagagatgaa caatcaattg ctgaagcaat aattgtagcc     120
atggtgtttt cgcaagaaga ttgcatgata aaagcagttc gaggcgattt gaacttcgtt     180
aatagagcaa atcagcgctt gaaccccatg catcaactct tgaggcattt ccaaaaagat     240
gcaaaagtgc ttttccagaa ttgggggatt gaacccatcg acaatgtgat gggaatgatt     300
ggaatattgc ctgacatgac cccaagcacc gagatgtcat tgagaggagt gagagtcagc     360
aaaatgggag tggatgagta ctccagcact gagagagtgg tggtgagcat tgaccgtttt     420
ttaagagttc gggatcaaag gggaaacata ctactgtccc ctgaagaggt cagtgaaaca     480
caaggaacgg aaaagctgac aataatttat tcatcatcaa tgatgtggga gattaatggt     540
cccgaatcag tgttggtcaa tacttatcaa tggatcatca ggaactggga aattgtgaaa     600
attcaatggt cacaggatcc cacaatgtta caataagat agaatttga gccattccag     660 tccctggtcc ctagggccac cagaagccaa tacagcggtt tcgtaagaac cctgtttcag     720
caaatgcgag atgtacttgg aacatttgat actgctcaaa taataaaact cctcccttt     780 gccgctgctc ctccggaaca gagtaggatg cagttctctt ctttgactgt taatgtaaga     840
ggatcgggaa tgaggatact tgtaagaggc aattccccag tgttcaacta caataaagcc     900
actaagaggc tcacagtcct cggaaaggat gcaggtgcgc ttactgaaga cccagatgaa     960
ggtacggctg agtagaatc tgctgttcta agagggtttc tcatttagg taaagaaaac    1020 aagagatatg cccagcact aagcatcaat gaactgagca aacttgcaaa agggagaaa    1080 gctaatgtgc taattgggca aggggacgtg gtgttggtaa tgaaacggaa acgtgactct    1140
agcatactta ctgacagcca gacagcgacc aaaaggattc ggatggccat caat         1194

<210> SEQ ID NO 22
<211> LENGTH: 1232
<212> TYPE: DNA
<213> ORGANISM: Equine influenza virus H3N8

<400> SEQUENCE: 22
agaattcaca atggtcggaa gagagcaac agccattctc agaaaggcaa ccagaagatt      60
gattcaattg atagtaagtg ggagagatga acaatcaatt gctgaagcaa taattgtagc     120
catggtgttt tcgcaagaag attgcatgat aaaagcagtt cgaggcgatt tgaacttcgt     180
taatagagca atcagcgct tgaaccccat gcatcaactc ttgaggcatt tccaaaaaga     240
tgcaaaagtg cttttccaga attgggggat tgaacccatc gacaatgtga tgggaatgat     300
tggaatattg cctgacatga ccccaagcac cgagatgtca ttgagaggag tgagagtcag     360
caaaatggga gtggatgagt actccagcac tgagagagtg gtggtgagca ttgaccgttt     420
```

-continued

```
tttaagagtt cgggatcaaa ggggaaacat actactgtcc cctgaagagg tcagtgaaac      480
acaaggaacg gaaaagctga caataattta ttcatcatca atgatgtggg agattaatgg      540
tcccgaatca gtgttggtca atacttatca atggatcatc aggaactggg aaattgtgaa      600
aattcaatgg tcacaggatc ccacaatgtt atacaataag atagaatttg agccattcca      660
gtccctggtc cctagggcca ccagaagcca atacagcggt ttcgtaagaa ccctgtttca      720
gcaaatgcga gatgtacttg aacatttga tactgctcaa ataataaaac tcctcccttt       780
tgccgctgct cctccggaac agagtaggat gcagttctct tctttgactg ttaatgtaag      840
aggatcggga atgaggatac ttgtaagagg caattcccca gtgttcaact acaataaagc      900
cactaagagg ctcacagtcc tcggaaagga tgcaggtgcg cttactgaag acccagatga      960
aggtacggct ggagtagaat ctgctgttct aagagggttt ctcattttag gtaaagaaaa     1020
caagagatat ggcccagcac taagcatcaa tgaactgagc aaacttgcaa aaggggagaa     1080
agctaatgtg ctaattgggc aagggacgt ggtgttggta atgaaacgga aacgtgactc      1140
tagcatactt actgacagcc agacagcgac caaaaggatt cggatggcca tcaattagtg     1200
ttgaattgtt taaaaacgac cttgtttcta ct                                   1232
```

<210> SEQ ID NO 23
<211> LENGTH: 1232
<212> TYPE: DNA
<213> ORGANISM: Equine influenza virus H3N8
<220> FEATURE:
<221> NAME/KEY: CDS
<222> LOCATION: (2)..(1195)
<223> OTHER INFORMATION:

<400> SEQUENCE: 23

```
a gaa ttc aca atg gtc gga aga aga gca aca gcc att ctc aga aag gca      49
  Glu Phe Thr Met Val Gly Arg Arg Ala Thr Ala Ile Leu Arg Lys Ala
  1               5                  10                  15 acc aga aga ttg att caa ttg ata gta agt ggg aga gat gaa caa tca        97
Thr Arg Arg Leu Ile Gln Leu Ile Val Ser Gly Arg Asp Glu Gln Ser
             20                  25                  30 att gct gaa gca ata att gta gcc atg gtg ttt tcg caa gaa gat tgc       145
Ile Ala Glu Ala Ile Ile Val Ala Met Val Phe Ser Gln Glu Asp Cys
         35                  40                  45 atg ata caa gca gtt cga ggc gat ttg aac ttc gtt aat aga gca aat      193
Met Ile Gln Ala Val Arg Gly Asp Leu Asn Phe Val Asn Arg Ala Asn
     50                  55                  60 cag cgc ttg aac ccc atg cat caa ctc ttg agg cat ttc caa aaa gat      241
Gln Arg Leu Asn Pro Met His Gln Leu Leu Arg His Phe Gln Lys Asp
 65                  70                  75                  80 gca aaa gtg ctt ttc cag aat tgg ggg att gaa ccc atc gac aat gtg      289
Ala Lys Val Leu Phe Gln Asn Trp Gly Ile Glu Pro Ile Asp Asn Val
                 85                  90                  95 atg gga atg att gga ata ttg cct gac atg acc cca agc acc gag atg      337
Met Gly Met Ile Gly Ile Leu Pro Asp Met Thr Pro Ser Thr Glu Met
            100                 105                 110 tca ttg aga gga gtg aga gtc agc aaa atg gga gtg gat gag tac tcc      385
Ser Leu Arg Gly Val Arg Val Ser Lys Met Gly Val Asp Glu Tyr Ser
        115                 120                 125 agc act gag aga gtg gtg gtg agc att gac cgt ttt tta aga gtt cgg      433
Ser Thr Glu Arg Val Val Val Ser Ile Asp Arg Phe Leu Arg Val Arg
    130                 135                 140 gat caa agg gga aac ata cta ctg tcc cct gaa gag gtc agt gaa aca      481
Asp Gln Arg Gly Asn Ile Leu Leu Ser Pro Glu Glu Val Ser Glu Thr
145                 150                 155                 160
```

|  |  |
|---|---:|
| caa gga acg gaa aag ctg aca ata att tat tca tca tca atg atg tgg<br>Gln Gly Thr Glu Lys Leu Thr Ile Ile Tyr Ser Ser Ser Met Met Trp<br>                    165                    170                  175 | 529 |
| gag att aat ggt ccc gaa tca gtg ttg gtc aat act tat caa tgg atc<br>Glu Ile Asn Gly Pro Glu Ser Val Leu Val Asn Thr Tyr Gln Trp Ile<br>            180                    185                    190 | 577 |
| atc agg aac tgg gaa att gtg aaa att caa tgg tca cag gat ccc aca<br>Ile Arg Asn Trp Glu Ile Val Lys Ile Gln Trp Ser Gln Asp Pro Thr<br>195                    200                    205 | 625 |
| atg tta tac aat aag ata gaa ttt gag cca ttc cag tcc ctg gtc cct<br>Met Leu Tyr Asn Lys Ile Glu Phe Glu Pro Phe Gln Ser Leu Val Pro<br>            210                    215                    220 | 673 |
| agg gcc acc aga agc caa tac agc ggt ttc gta aga acc ctg ttt cag<br>Arg Ala Thr Arg Ser Gln Tyr Ser Gly Phe Val Arg Thr Leu Phe Gln<br>225                    230                    235                  240 | 721 |
| caa atg cga gat gta ctt gga aca ttt gat act gct caa ata ata aaa<br>Gln Met Arg Asp Val Leu Gly Thr Phe Asp Thr Ala Gln Ile Ile Lys<br>                    245                    250                    255 | 769 |
| ctc ctc cct ttt gcc gct gct cct ccg gaa cag agt agg atg cag ttc<br>Leu Leu Pro Phe Ala Ala Ala Pro Pro Glu Gln Ser Arg Met Gln Phe<br>            260                    265                    270 | 817 |
| tct tct ttg act gtt aat gta aga gga tcg gga atg agg ata ctt gta<br>Ser Ser Leu Thr Val Asn Val Arg Gly Ser Gly Met Arg Ile Leu Val<br>275                    280                    285 | 865 |
| aga ggc aat tcc cca gtg ttc aac tac aat aaa gcc act aag agg ctc<br>Arg Gly Asn Ser Pro Val Phe Asn Tyr Asn Lys Ala Thr Lys Arg Leu<br>            290                    295                    300 | 913 |
| aca gtc ctc gga aaa gat gca ggt gcg ctt act gaa gac cca gat gaa<br>Thr Val Leu Gly Lys Asp Ala Gly Ala Leu Thr Glu Asp Pro Asp Glu<br>305                    310                    315                  320 | 961 |
| ggt acg gct gga gta gaa tct gct gtt cta agg ggg ttt ctc att tta<br>Gly Thr Ala Gly Val Glu Ser Ala Val Leu Arg Gly Phe Leu Ile Leu<br>                    325                    330                  335 | 1009 |
| ggt aaa gaa aac aag aga tat ggc cca gca cta agc atc aat gaa ctg<br>Gly Lys Glu Asn Lys Arg Tyr Gly Pro Ala Leu Ser Ile Asn Glu Leu<br>            340                    345                    350 | 1057 |
| agc aaa ctt gca aaa ggg gag aaa gct aat gtg cta att ggg caa ggg<br>Ser Lys Leu Ala Lys Gly Glu Lys Ala Asn Val Leu Ile Gly Gln Gly<br>355                    360                    365 | 1105 |
| gac gtg gtg ttg gta atg aaa cgg aaa cgt gac tct agc ata ctt act<br>Asp Val Val Leu Val Met Lys Arg Lys Arg Asp Ser Ser Ile Leu Thr<br>            370                    375                    380 | 1153 |
| gac agc cag aca gcg acc aaa agg att cgg atg gcc atc aat<br>Asp Ser Gln Thr Ala Thr Lys Arg Ile Arg Met Ala Ile Asn<br>385                    390                    395 | 1195 |
| tagtgttgaa ttgtttaaaa acgaccttgt ttctact | 1232 |

```
<210> SEQ ID NO 24
<211> LENGTH: 398
<212> TYPE: PRT
<213> ORGANISM: Equine influenza virus H3N8

<400> SEQUENCE: 24
```

Glu Phe Thr Met Val Gly Arg Arg Ala Thr Ala Ile Leu Arg Lys Ala
1                  5                        10                      15

Thr Arg Arg Leu Ile Gln Leu Ile Val Ser Gly Arg Asp Glu Gln Ser
                  20                        25                        30

Ile Ala Glu Ala Ile Ile Val Ala Met Val Phe Ser Gln Glu Asp Cys
                  35                        40                        45

| | | | | | | | | | | | |
|---|---|---|---|---|---|---|---|---|---|---|---|
| Met | Ile | Gln | Ala | Val | Arg | Gly | Asp | Leu | Asn | Phe | Val | Asn | Arg | Ala | Asn |
| 50 | | | | | 55 | | | | | 60 | |

Met Ile Gln Ala Val Arg Gly Asp Leu Asn Phe Val Asn Arg Ala Asn
        50                  55                  60

Gln Arg Leu Asn Pro Met His Gln Leu Leu Arg His Phe Gln Lys Asp
 65                  70                  75                  80

Ala Lys Val Leu Phe Gln Asn Trp Gly Ile Glu Pro Ile Asp Asn Val
                 85                  90                  95

Met Gly Met Ile Gly Ile Leu Pro Asp Met Thr Pro Ser Thr Glu Met
               100                 105                 110

Ser Leu Arg Gly Val Arg Val Ser Lys Met Gly Val Asp Glu Tyr Ser
              115                 120                 125

Ser Thr Glu Arg Val Val Ser Ile Asp Arg Phe Leu Arg Val Arg
130                 135                 140

Asp Gln Arg Gly Asn Ile Leu Leu Ser Pro Glu Glu Val Ser Glu Thr
145                 150                 155                 160

Gln Gly Thr Glu Lys Leu Thr Ile Ile Tyr Ser Ser Met Met Trp
                165                 170                 175

Glu Ile Asn Gly Pro Glu Ser Val Leu Val Asn Thr Tyr Gln Trp Ile
              180                 185                 190

Ile Arg Asn Trp Glu Ile Val Lys Ile Gln Trp Ser Gln Asp Pro Thr
          195                 200                 205

Met Leu Tyr Asn Lys Ile Glu Phe Glu Pro Phe Gln Ser Leu Val Pro
      210                 215                 220

Arg Ala Thr Arg Ser Gln Tyr Ser Gly Phe Val Arg Thr Leu Phe Gln
225                 230                 235                 240

Gln Met Arg Asp Val Leu Gly Thr Phe Asp Thr Ala Gln Ile Ile Lys
                245                 250                 255

Leu Leu Pro Phe Ala Ala Pro Pro Glu Gln Ser Arg Met Gln Phe
              260                 265                 270

Ser Ser Leu Thr Val Asn Val Arg Gly Ser Gly Met Arg Ile Leu Val
          275                 280                 285

Arg Gly Asn Ser Pro Val Phe Asn Tyr Asn Lys Ala Thr Lys Arg Leu
      290                 295                 300

Thr Val Leu Gly Lys Asp Ala Gly Ala Leu Thr Glu Asp Pro Asp Glu
305                 310                 315                 320

Gly Thr Ala Gly Val Glu Ser Ala Val Leu Arg Gly Phe Leu Ile Leu
                325                 330                 335

Gly Lys Glu Asn Lys Arg Tyr Gly Pro Ala Leu Ser Ile Asn Glu Leu
              340                 345                 350

Ser Lys Leu Ala Lys Gly Glu Lys Ala Asn Val Leu Ile Gly Gln Gly
          355                 360                 365

Asp Val Val Leu Val Met Lys Arg Lys Arg Asp Ser Ser Ile Leu Thr
      370                 375                 380

Asp Ser Gln Thr Ala Thr Lys Arg Ile Arg Met Ala Ile Asn
385                 390                 395

<210> SEQ ID NO 25
<211> LENGTH: 1194
<212> TYPE: DNA
<213> ORGANISM: Equine influenza virus H3N8

<400> SEQUENCE: 25
gaattcacaa tggtcggaag aagagcaaca gccattctca gaaaggcaac cagaagattg      60
attcaattga tagtaagtgg gagagatgaa caatcaattg ctgaagcaat aattgtagcc     120

```
atggtgtttt cgcaagaaga ttgcatgata caagcagttc gaggcgattt gaacttcgtt      180
aatagagcaa atcagcgctt gaaccccatg catcaactct tgaggcattt ccaaaaagat      240
gcaaaagtgc ttttccagaa ttgggggatt gaacccatcg acaatgtgat gggaatgatt      300
ggaatattgc ctgacatgac cccaagcacc gagatgtcat tgagaggagt gagagtcagc      360
aaaatgggag tggatgagta ctccagcact gagagagtgg tggtgagcat tgaccgtttt      420
ttaagagttc gggatcaaag gggaaacata ctactgtccc ctgaagaggt cagtgaaaca      480
caaggaacgg aaaagctgac aataatttat tcatcatcaa tgatgtggga gattaatggt      540
cccgaatcag tgttggtcaa tacttatcaa tggatcatca ggaactggga aattgtgaaa      600
attcaatggt cacaggatcc cacaatgtta tacaataaga tagaatttga gccattccag      660
tccctggtcc ctagggccac cagaagccaa tacagcggtt tcgtaagaac cctgtttcag      720
caaatgcgag atgtacttgg aacatttgat actgctcaaa taataaaact cctccctttt      780
gccgctgctc ctccggaaca gagtaggatg cagttctctt ctttgactgt taatgtaaga      840
ggatcgggaa tgaggatact tgtaagaggc aattccccag tgttcaacta caataaagcc      900
actaagaggc tcacagtcct cggaaaagat gcaggtgcgc ttactgaaga cccagatgaa      960
ggtacggctg gagtagaatc tgctgttcta agagggtttc tcatttttagg taaagaaaac     1020 aagagatatg cccagcacct aagcatcaat gaactgagca aacttgcaaa aggggagaaa     1080
gctaatgtgc taattgggca aggggacgtg gtgttggtaa tgaaacggaa acgtgactct     1140
agcatactta ctgacagcca gacagcgacc aaaaggattc ggatggccat caat           1194

<210> SEQ ID NO 26
<211> LENGTH: 23
<212> TYPE: DNA
<213> ORGANISM: Artificial sequence
<220> FEATURE:
<223> OTHER INFORMATION: Synthetic Primer

<400> SEQUENCE: 26
agcaaaagca ggtagatatt gaa                                                23

<210> SEQ ID NO 27
<211> LENGTH: 24
<212> TYPE: DNA
<213> ORGANISM: Artificial sequence
<220> FEATURE:
<223> OTHER INFORMATION: Synthetic Primer

<400> SEQUENCE: 27
agtagaaaca aggtagtttt ttac                                               24

<210> SEQ ID NO 28
<211> LENGTH: 18
<212> TYPE: DNA
<213> ORGANISM: Artificial sequence
<220> FEATURE:
<223> OTHER INFORMATION: Synthetic Primer

<400> SEQUENCE: 28
caggaaacag ctatgacc                                                      18

<210> SEQ ID NO 29
<211> LENGTH: 20
<212> TYPE: DNA
<213> ORGANISM: Artificial sequence
<220> FEATURE:
<223> OTHER INFORMATION: Synthetic Primer
```

```
<400> SEQUENCE: 29
taatacgact cactataggg                                        20

<210> SEQ ID NO 30
<211> LENGTH: 18
<212> TYPE: DNA
<213> ORGANISM: Artificial sequence
<220> FEATURE:
<223> OTHER INFORMATION: Synthetic Primer

<400> SEQUENCE: 30
tggtgcacta gccagctg                                          18

<210> SEQ ID NO 31
<211> LENGTH: 18
<212> TYPE: DNA
<213> ORGANISM: Artificial sequence
<220> FEATURE:
<223> OTHER INFORMATION: Synthetic Primer

<400> SEQUENCE: 31
ttgcctgtac catctgcc                                          18

<210> SEQ ID NO 32
<211> LENGTH: 23
<212> TYPE: DNA
<213> ORGANISM: Artificial sequence
<220> FEATURE:
<223> OTHER INFORMATION: Synthetic Primer

<400> SEQUENCE: 32
agcaaaagca ggggatattt ctg                                    23

<210> SEQ ID NO 33
<211> LENGTH: 23
<212> TYPE: DNA
<213> ORGANISM: Artificial sequence
<220> FEATURE:
<223> OTHER INFORMATION: Synthetic Primer

<400> SEQUENCE: 33
agtagaaaca agggtgtttt taa                                    23

<210> SEQ ID NO 34
<211> LENGTH: 16
<212> TYPE: DNA
<213> ORGANISM: Artificial sequence
<220> FEATURE:
<223> OTHER INFORMATION: Synthetic Primer

<400> SEQUENCE: 34
gacatccctg actatg                                            16

<210> SEQ ID NO 35
<211> LENGTH: 16
<212> TYPE: DNA
<213> ORGANISM: Artificial sequence
<220> FEATURE:
<223> OTHER INFORMATION: Synthetic Primer

<400> SEQUENCE: 35
gcatctgtta agtcaa                                            16

<210> SEQ ID NO 36
```

```
<211> LENGTH: 25
<212> TYPE: DNA
<213> ORGANISM: Artificial sequence
<220> FEATURE:
<223> OTHER INFORMATION: Synthetic Primer

<400> SEQUENCE: 36
agcaaaagca ggtcaaatat attca                                   25

<210> SEQ ID NO 37
<211> LENGTH: 26
<212> TYPE: DNA
<213> ORGANISM: Artificial sequence
<220> FEATURE:
<223> OTHER INFORMATION: Synthetic Primer

<400> SEQUENCE: 37
gaaaacacca tggctacaat tattgc                                  26

<210> SEQ ID NO 38
<211> LENGTH: 27
<212> TYPE: DNA
<213> ORGANISM: Artificial sequence
<220> FEATURE:
<223> OTHER INFORMATION: Synthetic Primer

<400> SEQUENCE: 38
agaattcaca atggtcggaa gaagagc                                 27

<210> SEQ ID NO 39
<211> LENGTH: 27
<212> TYPE: DNA
<213> ORGANISM: Artificial sequence
<220> FEATURE:
<223> OTHER INFORMATION: Synthetic Primer

<400> SEQUENCE: 39
agtagaaaca aggtcgtttt taaacaa                                 27

<210> SEQ ID NO 40
<211> LENGTH: 19
<212> TYPE: DNA
<213> ORGANISM: Artificial sequence
<220> FEATURE:
<223> OTHER INFORMATION: Synthetic Primer

<400> SEQUENCE: 40
agccgtacct tcatctggg                                          19

<210> SEQ ID NO 41
<211> LENGTH: 19
<212> TYPE: DNA
<213> ORGANISM: Artificial sequence
<220> FEATURE:
<223> OTHER INFORMATION: Synthetic Primer

<400> SEQUENCE: 41
agcactgaga gagtggtgg                                          19

<210> SEQ ID NO 42
<211> LENGTH: 19
<212> TYPE: DNA
<213> ORGANISM: Artificial sequence
<220> FEATURE:
<223> OTHER INFORMATION: Synthetic Primer

<400> SEQUENCE: 42
```

```
gtaagaggca attccccag                                                    19

<210> SEQ ID NO 43
<211> LENGTH: 18
<212> TYPE: DNA
<213> ORGANISM: Artificial sequence
<220> FEATURE:
<223> OTHER INFORMATION: Synthetic Primer

<400> SEQUENCE: 43
cagcttttcc gttccttg                                                     18
```